(12) United States Patent
Bourgeois-Lugand et al.

(10) Patent No.: US 8,361,517 B2
(45) Date of Patent: Jan. 29, 2013

(54) COMPOSITION FOR REGULATING LIPID METABOLISM

(75) Inventors: Marie Francoise Yvonne Bourgeois-Lugand, Loqueffret (FR); Walter Wahli, Echichens (CH); Ilhem El Kochairi, Lausanne (CH); Sylvain Pradervand, Chavannes-Renens (CH); Giles Didier Parisot, Ollon (CH)

(73) Assignee: Actigenomics S.A., Epalinges (CH)

( * ) Notice: Subject to any disclaimer, the term of this patent is extended or adjusted under 35 U.S.C. 154(b) by 196 days.

(21) Appl. No.: 12/738,116

(22) PCT Filed: Oct. 16, 2008

(86) PCT No.: PCT/IB2008/002815
§ 371 (c)(1), (2), (4) Date: Apr. 15, 2010

(87) PCT Pub. No.: WO2009/050580
PCT Pub. Date: Apr. 23, 2009

(65) Prior Publication Data
US 2010/0215761 A1   Aug. 26, 2010

(30) Foreign Application Priority Data
Oct. 16, 2007   (EP) .................................... 07118598

(51) Int. Cl.
| | | |
|---|---|---|
| *A61K 36/00* | (2006.01) | |
| *A61K 36/63* | (2006.01) | |
| *A61K 36/03* | (2006.01) | |
| *A61K 35/12* | (2006.01) | |
| *A61K 35/60* | (2006.01) | |
| *A61K 36/87* | (2006.01) | |
| *A61K 36/06* | (2006.01) | |
| *A61K 36/8962* | (2006.01) | |

(52) U.S. Cl. ........ 424/725; 424/520; 424/523; 424/766; 424/195.15; 424/754

(58) Field of Classification Search ........................ None
See application file for complete search history.

(56) References Cited

FOREIGN PATENT DOCUMENTS

| | | |
|---|---|---|
| JP | 62 061925 A | 3/1987 |
| JP | 08 000219 A | 1/1996 |
| JP | 2001 010947 A | 1/2001 |
| JP | 2002 275088 A | 9/2002 |
| WO | 99 48386 A | 9/1999 |
| WO | 00 09141 A | 2/2000 |
| WO | 2005 095427 A | 10/2005 |

OTHER PUBLICATIONS

Kinsella, J.E., "Grapeseed Oil: A rich source of linoleic acid", Food Technology, Institute of Food Technologists, Chicago, IL, vol. 28, No. 5, Jan. 1, 1974, pp. 58-60.
Mie-Youn Choi et al., "The effects of hot water soluble polysaccharides from Lentinus edodes on lipid metabolism in the rats fed yellow butter", Journal of the Korean Society of Food Science and Nutrition, vol. 29, No. 2, 2000, pp. 294-299.
Morihara Naoaki et al., "Aged garlic extract ameliorates physical fatigue", Biological & Pharmaceutical Bulletin, vol. 29, No. 5, May 2006, pp. 962-966.
International Search Report for PCT/IB2008/002815, dated Mar. 10, 2009.
Written Opinion for PCT/IB2008/002815, dated Mar. 10, 2009.

*Primary Examiner* — Qiuwen Mi
(74) *Attorney, Agent, or Firm* — Hoffmann & Baron, LLP

(57) ABSTRACT

This invention concerns a composition for regulating lipid metabolism and methods that may be used in the food industry as well as in the nutraceutical and therapeutic fields. In particular, the invention involves food additives or supplements, a composition containing these and the use thereof, in particular for revitalizing a subject's metabolism, in particular, that of human beings.

20 Claims, 39 Drawing Sheets

Control

Composition according to the invention

Control

Composition according to the invention

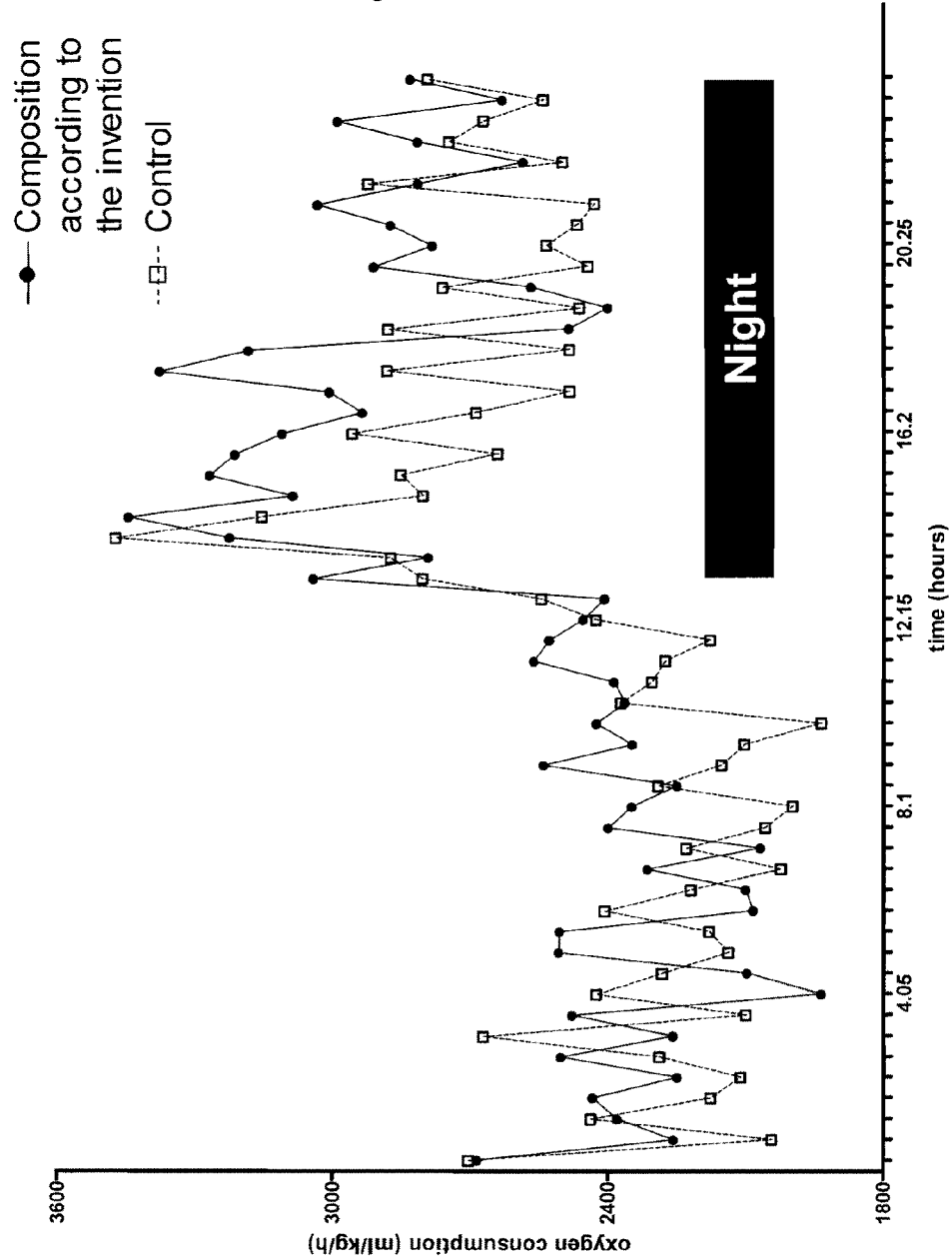

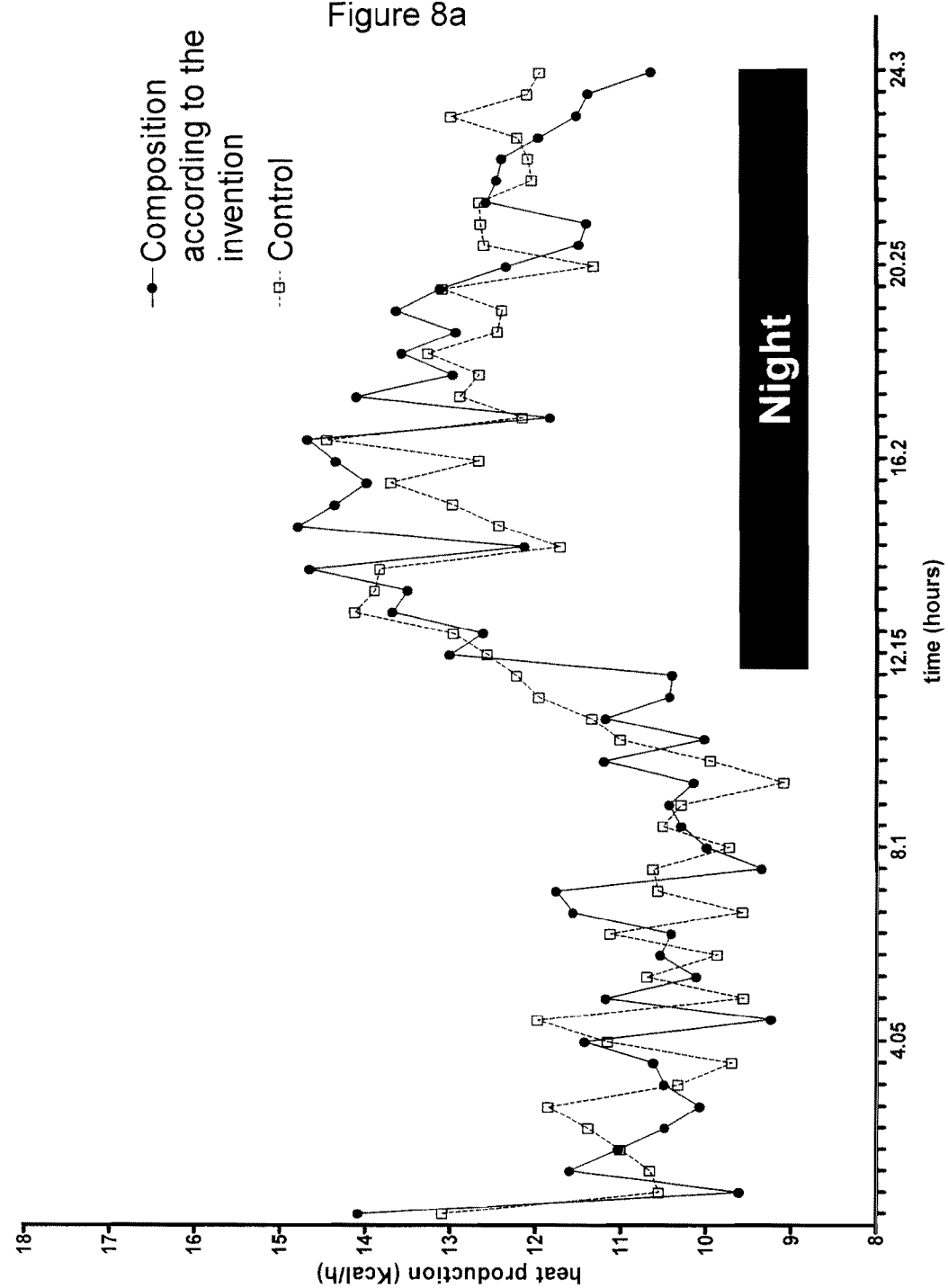

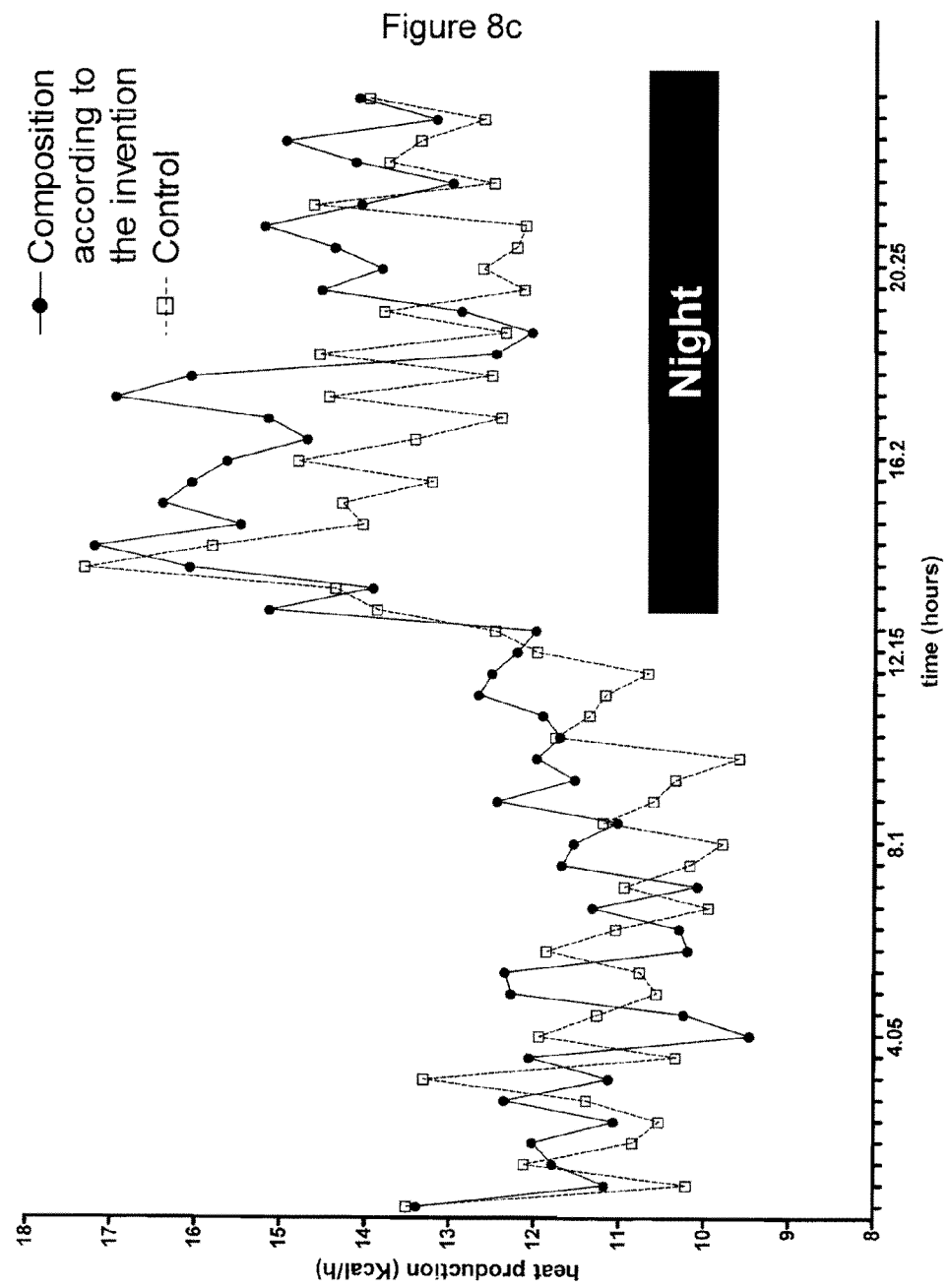

Figure 15

PPAR alpha target genes upregulated in muscle
(*enrichment by the composition according to the invention versus control)

Fatty acid uptake

| Gene | Value |
|---|---|
| CD36* | 3,49614854 |
| | 3,2040358 |
| | 3,92655389 |
| ABCA1 | 1,25607476 |
| | 2,95181319 |

Fatty acid mitochondrial oxidation

| Gene | Value |
|---|---|
| ACAA2* | 2,00745053 |
| ACADM | 1,67161308 |
| ACADVL | 1,5188451 |
| | 2,94931806 |
| | 2,42895757 |
| | 1,54951208 |
| ACAA2* | 2,50580403 |
| HADH | 1,27745581 |
| HMGCS1 | 2,84725028 |
| | 2,36925891 |
| HADHA | 2,52600452 |

Fatty acid peroxisomal oxidation

| Gene | Value |
|---|---|
| ABCD2* | 3,31015463 |
| ACOX1 | 1,48341923 |
| EHHADH | 2,83032541 |
| ACBD3 | 1,303356918 |
| ALDH2 | 2,16399101 |
| ACAA2* | 2,00745053 |
| CYP4A1 | 2,7877106 |
| SLC27A2 | 5,05235117 |
| ALDH3A2 | 2,318474 |
| ALDH1A1 | 1,62703052 |

COMPOSITION FOR REGULATING LIPID METABOLISM

CROSS-REFERENCE TO RELATED APPLICATIONS

This application is the National Stage of International Application No. PCT/IB2008/002815, filed Oct. 16, 2008, which claims the benefit of European Application No. 07118598.7, filed Oct. 16, 2007, the contents of which are incorporated by reference herein.

FIELD OF THE INVENTION

This invention concerns a composition for regulating lipid metabolism and methods that may be used in the food industry as well as in the nutraceutical and therapeutic fields. In particular, the invention involves food additives or supplements, a composition containing these and the use thereof, in particular for revitalizing a subject's metabolism, in particular, that of human beings.

DISCUSSION OF THE STATE OF THE ART

Nutrition plays a crucial role in maintaining the good health or the general well being of the subjects. In particular, nutrition makes it possible to strengthen the general state of health of a subject, by reducing tiredness, improving memory, by boosting certain functions necessary to the vitality of the body, specifically by stimulating both general metabolism and the metabolism of fuel (lipids, sugars, proteins).

FENOFIBRATE® (EP0295637 WARNER LAMBERT) is used to reduce blood levels of triglyceride and cholesterol, together with diet. It acts by activating the alpha Peroxisome Proliferator Activated Receptor (PPAR-alpha). This activation involves an increase in lipolysis and the removal of atherogenic particles rich in triglycerides (LDL and VLDL) from the plasma. All this leads to a reduction in the blood-levels of triglyceride and cholesterol. The following side effects caused by FENOFIBRATE® were observed: digestive disorders, muscle pains, elevation of blood transaminases, cephalgias (headaches), diarrhea, and skin allergies. FENOFIBRATE® is contra-indicated when severe hepatic or renal insufficiency or allergy is present.

Phytosterols are natural compounds present in plants, oleaginous plants and the oils extracted thereof, as well as in pine oil. Phytosterols used for reducing cholesterol levels are generally extracted from plant oils (soy, corn, sunflower, and rapeseed) and appear as a waxy substance with low solubility. These are combined with fatty-acids in order to achieve proper integration and better absorption into food (margarines, salad dressings, etc). Because of their close chemical structure, phytosterols block the absorption of cholesterol by occupying its absorption sites in the intestine. Although the chemical description of phytosterols goes back to 1922, it is not until the seventies that their beneficial action on cholesterol levels was seriously considered. Clinical trials carried out since the mid seventies show that phytosterols allow LDL cholesterol (Low Density Lipoprotein Cholesterol "also called bad cholesterol") levels to be reduced by 8% to 12%. Consuming food enriched with phytosterols or phytosterol supplements can reduce the blood levels of carotenoid (β-carotenoids, lycopene). This effect is attributable to the reduction in intestinal absorption of these substances. Phytosterols are contra-indicated in the cases of sitosterolemia and certain xanthomatoses. It has been proven that phytosterols are ineffective on triglycerides, and that their effectiveness on LDL/cholesterol is rather limited.

It is known that nutrients like trace elements, plants, essential elements (amino-acids) or vitamins can activate or inhibit certain bodily functions, or can have a purely energy-neutral effect. Micronutrition, consisting in providing one or more nutrients to the body in reduced amounts, has allowed a partial resolution of problems related to traditional nutrition during a weight loss regime. These reduced amounts allow nutrients to be directly assimilated in the final recipient which is the cell. Nutrition during a weight loss regime does not allow this. But more importantly, micronutrition has helped solve the problem of saturating absorption sites. Thus, micronutrition does not saturate the intestinal absorption sites.

DE 19930221 A1 (MARCINOWSKI PETER) (Jan. 11, 2001) discloses a type of food with improved nutritional value, which includes yeasts, vitamins, plant oils, in particular linseed oil, marine algae, and a mixture of minerals. The yeasts include trace metals and minerals, as well as B-complex vitamins.

Document DATABASE WPI Week 200316 Derwent Publications Ltd., London; YEAR 2003-160118 XP002477227 & JP 2002 291419 A (FANKERU KK) (Oct. 8, 2002) discloses an easy to prepare composition in the form of capsule, which includes an oil, vitamin B2, thiamin, vitamin B6, vitamin B12, folic acid, biotin, pantothenic acid, the vitamins P, D, E, F and K, carotenoids, metal-containing yeast, ascorbic acid, and nicotinamide. The oil used may be selected from perilla oil, peanut oil, wheat germ oil, olive oil, grapeseed oil, safflower oil, DHA, EPA, and evening primrose oil.

RU-C1-2 159 564 (ORLOVA RAISSA PETROVNA ET AL.) (Nov. 27, 2000) discloses a composition including yeast, plant oils, and a few active ingredients, which are sea kale, nuts and/or honey, which increases resistance to irradiation and has stimulative properties. The yeasts include trace metals and minerals, as well as B-complex vitamins.

Document DATABASE FSTA [Online] INTERNATIONAL FOOD INFORMATION SERVICE (IFIS), FRANKFURT-MAIN, DE; KINSELLA J. E: "Grapeseed oil: a rich source of linoleic acid" XP002477226 Database accession no. 74-4-07-n0351 discloses that grapeseed oil may be used as a functional ingredient in food to reduce blood levels of cholesterol.

WO 00/09141 A (WAKUNAGA OF AMERICA CO LTD ET AL.) (Feb. 24, 2000) discloses a composition including garlic extract, B6 and B12 vitamins, and folic acid for reducing homocystein blood levels. Thus, the risk of cardiovascular diseases such as myocardial infarctions is reduced. It is specifically disclosed that preparations containing garlic reduce blood levels of cholesterol.

US 2002/172729 A1 (KENTON KALEVI JOHN ET AL.) (Nov. 21, 2002) describes a pharmaceutical composition including ascorbic acid, vitamin E, magnesium, amino-acids, flavonoids, and lycopene as active ingredients for the prevention of cardiovascular diseases such as the atheromatous plaques, and some myocardial infarctions. Garlic powder may be present.

WO 2005/095427 A (TAKARA BIO INC ET AL) (Oct. 13, 2005) discloses a composition including a polysaccharide sulfate derived from algae of the *Fucus* type with a reduced molecular weight, for the prevention or treatment of thromboses.

DATABASE WPI Week 199610 Derwent Publications Ltd., London; YEAR 1996-091609 XP002256701-& JP 08 000219 A (NIPPON SYNTHETIC CHEM IND CO) (1996 Jan. 9) describes a composition to prevent cholesterol formation and cerebral thromboses, including a natural polysaccharide such as carrageenan, and fish oil such as sardine or tuna oil as active ingredients.

JP 2002 275088 A (NAGAOKA HITOSHI) (Sep. 25, 2002) discloses a composition including an extract of shiitake mycelium to inhibit artherosclerosis (Cortinellus shiitake fungus).

WO 99/48386 A (STUECKLER FRANZ) (1999 Sep. 30) discloses a food composition based on natural substances, which has a preventive effect on cardiovascular diseases. It contains lecithin, red vine and tocopheryl acetate extract, as well as salmon oil, shiitake extract, vitamins B-complex (folic acid, vitamins B1, B2, B6, B12, nicotinamide, pantothenol, biotin), garlic extract, and ascorbic acid. The matrix of the composition may be medicinal yeast or olive oil. It is revealed that (1) olive oil reduces the blood level of cholesterol because of its high oleic acid content; (2) garlic extract has a protective effect against artherosclerosis and the formation of atheromatous plaques; (3) B-complex vitamins reduce the blood levels of homocystein and thus arteriosclerosis; (4) shiitake extract reduces the formation of atheromatous plaques, reducing the blood level of cholesterol, and the risk of thromboses; (5) fish oils reduce the blood level of triglycerides and the aggregation of thrombocytes.

In spite of the solutions suggested by the prior art, there is no effective composition having no undesirable effects or side effects on the body, which at the same time acts to:
 reduce circulating lipids
 prevent atheromatous plaques
 prevent hepatic steatosis
 control weight; prevent obesity by stabilizing the body fat mass, with a limit on the size of adipocytes
 increase oxidative lipid catabolism and oxygen uptake
 and improve physical performance and endurance

BRIEF DESCRIPTION OF THE INVENTION

This invention proposes a response to the demand to create an innovative composition designed to regulate lipid metabolism in humans and animals. Among other things, the composition in accordance with the invention permits significant action on fat metabolism while providing particularly advantageous results at the same time for lowering total cholesterol (up to −18%), LDL-C (up to −20%), and triglycerides (up to −35%).

More in particular, this invention concerns a composition designed for regulating lipid metabolism in humans and animals. This composition comprises the combination of:
 7 µg to 700 µg (per 100 g/100 ml) of at least two plant oils selected from among rapeseed oil, olive oil, grapeseed oil, and evening primrose oil,
 10 µg to 1000 µg (per 100 g/100 ml) of positively charged minerals chosen from among sodium, magnesium, and calcium,
 10 µg to 1000 µg (per 100 g/100 ml) of metals chosen from between zinc and iron,
 7 µg to 700 µg (per 100 g/100 ml) of yeast or yeast extracts originating from the *Saccharomyces cerevisiae* genus, characterized in that said yeasts or yeast extracts are enriched with Selenium;
 7 µg to 700 µg (per 100 g/100 ml) of mushrooms or Shiitake mushroom extracts (mycelium)
 6 µg to 600 µg (per 100 g/100 ml) of at least two plant extracts from plants chosen from among samphire, garlic, and grapevine,
 8 µg to 800 µg (per 100 g/100 ml) of at least one vitamin chosen among vitamins A, B1, B9, C, E, F, and PP
 7 µg to 700 µg (per 100 g/100 ml) of animal oil and Copra oil (*Cocos nucifera*)
 6 µg to 600 µg (per 100 g/100 ml) of at least one alga chosen among *Palmaria palmata* (Dulse), *Chondrus crispus* (Carrageen), and *Fucus vesiculosus* (Bladder wrack), as well as a pharmaceutical and/or alimentary acceptable excipient.

Said excipient will advantageously supplement the volume so as to obtain 100 ml of the composition in accordance with the invention.

In the Examples hereafter, the composition in accordance with the invention was shown to produce unexpected synergistic effects, which are by far greater than those of the ingredients taken separately and which does not produce the surprising results linked to the composition as described.

The invention also concerns the use of a composition as defined for the preparation of a food additive.

Another object of the invention concerns a method to control lipid metabolism in a subject, including the administration, application, or ingestion of a composition as defined in the present application.

Another object of the invention concerns a method to decrease triglyceride levels in a subject, including the administration of a composition as defined in this invention.

Another object of the invention concerns a method to decrease cholesterol levels in a subject, including the administration of a composition in accordance with the invention.

The use of said composition to prepare a drug or nutritional product designed to regulate the metabolism of lipids in humans and animals is also one of the objects of this invention.

In particular, regulating the metabolism of lipids consists of maintaining and/or regenerating the human or animal body by rebalancing and restimulating the general functions of said metabolism including:
stimulation of lipid consumption by the body and/or
reduction in plasma cholesterol and/or triglyceride levels, The medicament or nutritional product in accordance with the invention may be used for treatment or prevention of metabolic syndrome, the formation of the atheromatous plaques, the hepatic steatosis and/or cardiovascular diseases.

Other unexpected advantages of the composition in accordance with the invention will become apparent upon reading the detailed description and examples of embodiments of the invention.

BRIEF DESCRIPTION OF THE FIGURES

FIG. 7f: Oxygen uptake at 9 months in APOEko male mice (treatment begun at 10 weeks of age)

FIG. 8a: Heat production at 3 months in APOEko male mice (treatment begun at 10 weeks of age)

FIG. 8c: Heat production at 9 months in APOEko male mice (treatment begun at 10 weeks of age)

FIG. 15: Genes controlled by PPAR alpha and overexpressed in muscles in OB/OB mice after one month of treatment

DETAILED DESCRIPTION OF THE INVENTION

Figure 1:
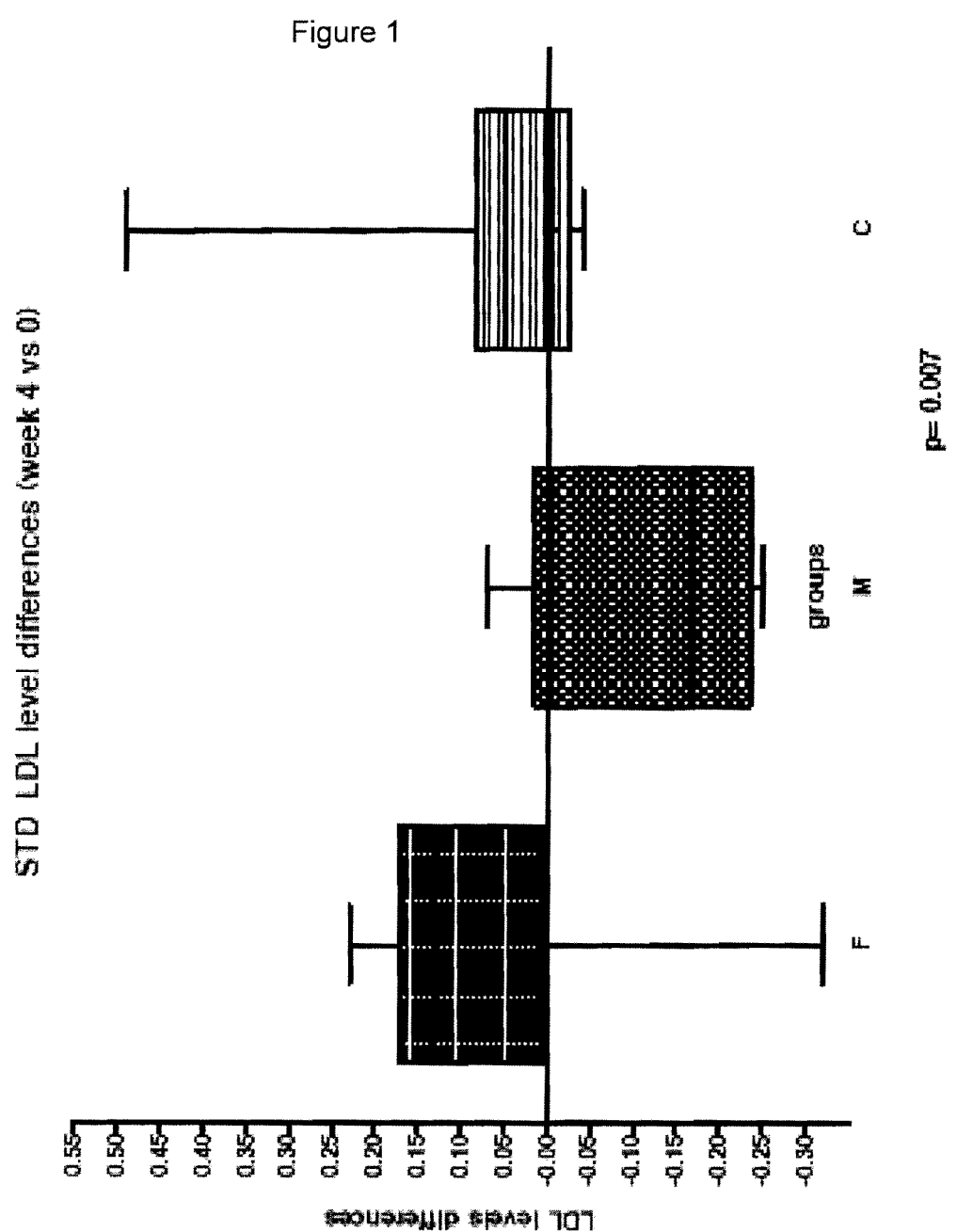
FIG. 1: Development of plasma LDL levels in ob/ob mice

This invention concerns the implementation of a composition usable as an additive or a food or nutritional supplement, and/or as a nutraceutical and/or therapeutic supplement, displaying properties which are particularly advantageous on the metabolism of lipids.

The composition of the invention is usable in the field of nutrition, in humans or in animals, and include preventive care.

Surprisingly, the composition in accordance with the invention makes it possible to cause a simultaneous and substantial reduction in total cholesterol (up to −18%) and in triglycerides (up to −35%) in humans, and an average reduction in LDL levels (up to −20%). The composition of the invention thus has the advantage of acting upon cholesterol and triglycerides at the same time, and without any identified side effects. These properties confer to the composition of the invention some especially advantageous applications in the field of revitalization in the metabolism of lipids, for example in subjects affected or likely to be affected by metabolic syndrome or other disorders related to dysregulation of lipid metabolism.

Additionally, the studies performed show that the effect of the composition of the invention results from a mechanism of action that is advantageous and different from existing medicaments or preparations. Indeed, the action on lipid metabolism regulation comes from a positive action (stimulating or revitalizing) on the cholesterol consumption, rather than from an inhibitory action on cholesterol synthesis or adsorption. This action on cholesterol consumption is exerted on the level of skeletal muscles in particular.

Moreover, the data obtained show that the action of the composition of the invention mobilizes fewer metabolic or genetic pathways than the available medicaments such as the fibrates. Thus, it is obtained by modulating the expression of a restricted number of genes, in comparison with medicaments used to date.

The preparation of the invention presents a particular composition and an important biological action, mediated by a particularly advantageous mechanism.

The first object of this invention is to provide a composition designed to regulate the metabolism of lipids in humans and animals. This composition comprises the combination of:

7 µg to 700 µg (per 100 g/100 ml) of at least two plant oils selected from among rapeseed oil, olive oil, grapeseed oil, and evening primrose oil, 10 µg to 1000 µg (per 100 g/100 ml) of positively charged minerals chosen from among sodium, magnesium, and calcium, 10 µg to 1000 µg (per 100 g/100 ml) of metals chosen from between zinc and iron, 7 µg to 700 µg (per 100 g/100 ml) of yeast or yeast extracts originating from the *Saccharomyces cerevisiae* genus, characterized in that said yeasts or yeast extracts are enriched with Selenium;

7 µg to 700 µg (per 100 g/100 ml) of mushrooms or Shiitake mushroom extracts (mycelium)

6 µg to 600 µg (per 100 g/100 ml) of at least two plant extracts from plants chosen from among samphire, garlic, and grapevine, 8 µg to 800 µg (per 100 g/100 ml) of at least one vitamin chosen among vitamins A, B1, B9, C, E, F, and PP 7 µg to 700 µg (per 100 g/100 ml) of animal oil and Copra oil (*Cocos nucifera*)

6 µg to 600 µg (per 100 g/100 ml) of at least one alga chosen among *Palmaria palmata* (Dulse), *Chondrus crispus* (Carrageen), and *Fucus vesiculosus* (Bladder wrack), as well as a pharmaceutically and/or nutritionally acceptable excipient.

Preferably the composition in accordance with the invention comprises cold water fish oil (Oleum Pisci mare fresca) as well as animal oil.

According to a preferred embodiment, the composition in accordance with the invention contains at least two vitamins chosen from among vitamins A, B1, B9, C, E, F, and PP.

More in particular, the composition of the invention preferably comprises

7 µg to 700 µg (per 100 g/100 ml) of rapeseed oil, olive oil, grapeseed oil, and evening primrose oil, 10 µg to 1000 µg (per 100 g/100 ml) of sodium, magnesium, and calcium, 10 µg to 1000 µg (per 100 g/100 ml) of zinc and iron, 7 µg to 700 µg (per 100 g/100 ml) of *Saccharomyces cerevisiae* yeast or yeast extracts, enriched with Selenium, 7 µg to 700 µg (per 100 g/100 ml) of mycelium or Shiitake mycelium extracts, 6 µg to 600 µg (per 100 g/100 ml) of samphire, garlic, and grapevine, 8 µg to 800 µg (per 100 g/100 ml) of vitamins A, B1, B9, C, E, F, and PP 7 µg to 700 µg (per 100 g/100 ml) of cold water fish oil and Copra oil, 6 µg to 600 µg (per 100 g/100 ml) of *Palmaria palmata* (Dulse), *Chondrus crispus* (Carrageen), and *Fucus vesiculosus* (Bladder wrack), Preferably, the composition of the invention shall include excipients or additives, for example: water, oil, lactose-saccharose or lactose-starch fructo-oligosaccharides, sorbitol, dicalcium phosphate.

Among the excipients used in foods (as food additives): dyes, preservatives (potassium sorbate, sodium benzoate), flavors, antioxidants (carotenoids, vitamins C and E, flavonoids), emulsifiers (lecithin, mono and di-glycerides of fatty-acids), stabilizing and gelling agents (lecithin, potassium lactate, agar i, carrageenans, sodium alginate), flavor enhancers (glutamic acid salts, sodium inosinate), acidifiers (citric acid, sodium malate), anti-caking agents (magnesium stearate, silicon dioxide), sweeteners (sorbitol, sodium saccharin).

The composition of the invention may be packaged in different ways, and in particular as a food supplement or additive designed to be added to all kinds of food bases and/or drinks in solid, liquid, gel form, in strips, pastes, powders, gums, etc. It may be packaged in any suitable type of support, like bottles, boxes, blister packs, flasks, phials, etc. It is typically designed for oral administration.

Additionally, the composition of the invention may be used as a food supplement or additive, in combination with other products, drinks, condiments, etc. For example, the composition in accordance with the invention may be incorporated into food bases and/or drinks, such as margarines, oils, powdered milk, dairy products (dessert creams, yogurts, etc), cereal bars, drinks (mineral water, fruit juices, etc), salts, condiments, sauces, etc The applicants attempted to develop a composition, usable as a nutritional active ingredient or food supplement or additive, as a nutraceutical and/or medicament, in order to improve the condition of subjects. More in particular, the applicants sought to develop a composition having a detoxifying and antioxidant action, to act on the assimilation of circulating cholesterol and its removal, to act on increasing the turnover of lipids, to act as a stimulant for basal metabolism regulating the burning of fuel and the vitality of cells and the body, and/or to act in the beneficial transformation of polyunsaturated fatty-acids, for example on their anti-inflammatory effect.

This research was targeted in particular on perfecting a composition which presents properties to act on:

detoxifying function: stimulation and regulation of hepatic cells, the gall bladder, and the small intestine. This function is the first preventative and regulatory action on lipid metabolism. It allows the evacuation of toxins, elimination of wastes coming from food, from cellular activity, the destruction of micro-organisms, from the drug use, from fat metabolism, and from pollution of the environment.

defense against free radicals acts to reduce oxidation of LDL and to neutralize active derivatives of oxygen increase of permeability of the cell membranes basal metabolism regulating one part of the burning of fuel and cellular vitality regulation of lipid metabolism This research led to the selection of different types of ingredients, and to develop and test different possible combinations of these ingredients, and to retain a composition such as defined above, including:

plant oils, minerals, metals (trace elements), yeast or yeast extracts, mushrooms or mushroom extracts, marine algae or their extracts, vegetable extracts (plants), and vitamins.

Trace elements are the elements of Mendeleev's table, metals or metalloids found within the body.

Plants or plant extracts are usually plants having a phytotherapeutic action also called simple. These are plants the effects of which are scientifically recognized or known by tradition.

Vitamins may be any substance fulfilling a vitamin function for the body.

Plant oils preferably include at least two oils chosen from among rapeseed oil, olive oil, grapeseed oil, and evening primrose oil. Advantageously, the composition should include at least three plant oils, more preferentially it includes rapeseed oil, olive oil, grapeseed oil, and evening primrose oil.

98% of rapeseed oil (Oleum *Brassica napus oleifera*) is made up by fatty acid triesters; the remaining 2% is rich in sterols and tocopherols (which is vitamin E). It is an oil rich in alpha-linoleic acid, omega-3 poly-unsaturated fatty-acids, omega-6 mono-unsaturated fatty-acids (with an interesting Omega 3:6 ratio of 1:2.5); and only 6 to 8% of saturated fatty-acids.

Olive oil (Oleum *Olea europea*) is an oil rich in oleic acid: mono-unsaturated fatty acids (>75%), Omega 6 (8%); olive oil contains vitamins A, E and K. The ratio of vitamin E/PUFA (Poly Unsaturated Fatty Acids) is the highest of all oils.

Grapeseed oil (*Vitis* Oleum *vinifera*) is an oil with balanced linoleic acid (alpha-linoleic and beta-linoleic), oleic, palmitic and stearic acids. More than 70% of Omega-6. Strongly unsaturated: the ratio of poly-unsaturated/saturated>5.

Evening primrose oil (Oleum *Oenothera biennis*) is an Omega-6 oil balanced in linoleic acid, gamma-linoleic acid, and oleic and stearic acids.

In one particular embodiment, the composition includes rapeseed oil, olive oil, grapeseed oil, and evening primrose oil.

Preferably, the minerals include one or more positively charged minerals, preferably chosen from among sodium, magnesium, and calcium.

Sodium allows acid-base regulation and cellular metabolism of the body.

It plays a determining role in cellular depolarization which is at the root of impulse excitability and conduction (in particular the neuromuscular and cardiac impulses), in maintaining acid-base balance, osmotic pressure, and in the balance between the body's liquid and ionic exchanges.

Magnesium is essential to the balance of the ionic channels. It acts as enzymatic cofactor and modulates the NA+ and K+ transport systems in all tissues; it is the physiological regulator of Calcium in the balance of cellular exchange. Magnesium plays a role in establishing the different intracellular organelles: It establishes ribosomes that produce proteins, maintaining the production of energy by the mitochondria because they are essential to the synthesis of ATP molecules. This production of energy is the basis for all cell life mechanisms and the overall vitality of the body. Magnesium is essential to the synthesis of proteins fundamental to cellular construction (certain amino-acids, DNA and RNA).

Calcium is involved in many enzymatic reactions. It allows the transmission of information at the cellular level as a second messenger that induces the transmission of the nerve impulse, muscle contraction (by forming actinomyosin), stimulation of secreting cells (hormones, such as insulin), and the release of neurotransmitters.

In one particular embodiment, the composition includes sodium, magnesium, and calcium.

Preferably the metals should include one or more metals chosen either zinc or iron.

Zinc intervenes in the activity of almost 200 enzymes (in particular in enzymatic systems like oxidoreductases, alcohol dehydrogenase, cytochrome reductase, and SOD or Superoxidismutase). Enzymes that are linked to Zinc are significantly important in metabolic processes: glycolysis, pentose pathway, neoglucogenesis, lipid and fatty acid metabolism.

Zinc is a metal activator for the majority of the coenzymes necessary for energy metabolism.

Zinc plays a very important role in acid-base balance (carbonic anhydrase), for inflammation, cellular differentiation, and in the endogenous defense against free radicals.

Zinc is a hormonal cofactor (growth hormone, thyroid, adrenal cortex) and is essential to the transcription of the DNA chain (RNA-polymerase).

Zinc stabilizes cellular membranes and when coupled with thiol groups they thus prevent their reaction with iron, thus avoiding production of very unstable H2O2 free radicals. In particular, it intervenes in the metabolism of vitamin A (mobilization at the level of the liver, formation of retinol).

It stabilizes the protein structures and plays a role in gene expression.

As a component of the cytochromes, iron is essential to the detoxication and the production of thyroid hormones. It belongs to protein active sites (known as "iron proteins") which play an important role in the body: hemoglobin, myoglobin, and cytochromes.

In one particular embodiment, the composition includes zinc and iron

The yeast or yeast extracts are preferably yeasts of the *Saccharomyces* genus, or are extracts of these yeasts (for example, membrane, vesicle, protein preparations, etc. ... ). They are in particular yeasts (or extracts) of the genus *Saccharomyces cerevisiae*. In one particular embodiment, (extracts of) yeasts enriched with Selenium are used, which has antioxidant properties.

For example, other yeasts of the Saccharomyces genus may also be used as those which are used in:
  the agricultural and food industry *saccharomyces boulardii*
  alcoholic fermentation:
    *saccharomyces cerevisiae* ("high fermentation" for wine, beer)
    *saccharomyces uvarum* ("low fermentation" for Lager-type beers)
    *schizosaccharomyces pombe* (African beer)
    *aspergillus* (sake)
  or also *torulaspora delbrueckii* and *candida stellata* (initially present in must): an increase in esters and a reduction in the formation of volatile acid Plant extracts preferably including one or more plant extracts. More preferably, the composition includes, as a plant extract, at least two plant extracts selected from among samphire, garlic, and grapevine. Advantageously, the composition includes samphire, garlic, and grapevine.

The term plant "extracts" indicates, within the meaning of this invention, any preparation obtained from the entire or part of the plant in question. They may be ground, filtered, from seeds, leaves, stems, bark, etc, or combinations. The extract can be prepared by traditional techniques. Typically, the extract includes plant cells, which may be intact or not.

Samphire (*Crithmum maritimum*) is very rich in minerals: zinc, iron, magnesium, copper, and manganese, in vitamins A, E, B1, and B2. It has a detoxifying action.

Garlic (*Allium sativum*) is rich in vitamin C, zinc, manganese, and has a cholesterol-lowering action. Garlic is characterized by the presence of original sulfur substances (allyl trisulphide, ajoene E) with beneficial effects on blood fluidity (reduces platelet aggregation) and blood cholesterol level (reduces the synthesis of triglycerides): of interest at the cardiovascular level.

Grapes or grapevines (*Vitis vinifera*) is very rich in vitamins A and B and minerals: manganese, potassium, calcium. Grapes drain the gall bladder and the liver. It is very rich in substances that fight free radicals.

The composition in accordance with the invention includes at least one alga or an extract of alga chosen from among *Palmaria palmata* (Dulse), *Chondrus crispus* (Carrageen) and *Fucus vesiculosus* (Bladder wrack).

Dulse (*Palmaria palmata*) is very rich in provitamin A, good for hormonal control, and is rich in vitamin C, for fighting free radicals. Rich in essential amino-acids.

Bladder wrack (*Fucus vesiculosus*) is rich in fucosterol: a sterol which presents properties for lowering lipids like beta-sitosterol plant sterols. It is also very rich in iodine and iron.

Carrageen (Irish moss—*Chondrus Crispus*) is rich in fatty-acids and is well balanced between omega-3 and omega-6 fatty-acids, as well being rich in unsaturated fatty-acids allowing the assimilation of cholesterol. It is also rich in amino-acids and trace elements (especially Iodine, Zinc, and Iron); contains all the vitamins.

In one particular embodiment, the composition includes extracts of *Palmaria palmata* (Dulse), *Chondrus crispus* (Carragaeen), and *Fucus vesiculosus* (Bladder wrack).

The composition in accordance with the invention includes at least one mushroom or Shiitake mushroom (mycelium) extract. The Shiitake mycelium (*Lentinus edodes*) is very rich in amino-acids, trace elements, and vitamins. It presents cholesterol-lowering and pro-immunizing properties.

In a preferred way, the vitamins include one or more vitamins chosen from among the vitamins A, B1, B9, C, E, F, and PP.

In a preferred embodiment, the composition includes at least two different vitamins, more preferentially at least three, four, five or six different vitamins, chosen from among the vitamins indicated above.

Vitamin A (retinol) is esterified inside the intestinal cell, incorporated to chylomicrons, excreted in the lymph, and enters general circulation through the lymphatic channel. Vitamin A stabilizes cell membranes, biosynthesis and regulation of steroid hormones. The synthesis of certain proteins is also dependant on vitamin A.

Vitamin B1 (thiamin) provides sterols and fatty-acids to the cell in NADPH2 acid, which is of paramount importance for the synthesis of lipids. It is one of the essential links for neolipidogenesis.

Vitamin B9 (folic acid) plays an important role in the metabolism of serine which is transformed into Acetyl-coenzyme A.

Vitamin C (ascorbic acid) plays an important biochemical role at the initial stages of lipid metabolism, in association with various hydroxylases. In the presence of ascorbic acid, the microsomal cytochrome P450-dependent hydroxylases act as a catalyst in the transformation of cholesterol into biliary acids.

Vitamin E (alpha-tocopherol) accompanies chylomicrons within the lymphatic channels until reaching general circulation. In plasma, alpha-tocopherol is linked to several lipoprotein categories: to LDL which contains between 40 and 60% of tocopherols and to HDL which contains 34%. Its level is strongly related to that of the total lipids and cholesterol. It has an antioxidant effect: buffering free radicals. It takes part in the formation and structure of membrane phospholipids, and has a stabilizing effect on cell membranes.

Vitamin F (linoleic acid) is an essential unsaturated fatty-acid for the synthesis and protection of lipids.

Vitamin PP (niacin) presents a cholesterol-lowering effect (by stimulating lipase protein or inhibiting lipolysis mediated by cyclic AMP in adipose tissue). It is also a crucial agent in cell energy metabolism through its intervention in all redox phenomena of the body.

In one particular embodiment, the composition includes vitamin A, vitamin B1, vitamin B9, vitamin C, vitamin E, vitamin F, and vitamin PP.

Additionally in a preferred embodiment, the composition of the invention also includes animal oil, in particular fish oil, in particular a cold water fish oil (Oleum pisci mare fresca). This oil is rich in Omega 3 fatty-acid. Omega 3 fatty acids reduce the blood level of triglycerides by decreasing liver synthesis of triglycerides, by reducing VLDL in the blood and their high triglyceride content, which makes faster metabolism possible. Omega-3s allow good membrane fluidity.

In addition, in one particularly preferred embodiment, the composition of the invention also includes (*Cocos nucifera*). Copra is rich in fatty-acid and represents an intestinal regulator.

One object of the invention thus concerns a composition including rapeseed oil, olive oil, grapeseed oil, evening primrose oil, cold water fish oil, Copra, sodium, magnesium, calcium, zinc, iron, an (extract from) yeast(s) *Saccharomyces cerevisiae*, preferably enriched with selenium, plant extracts from samphire, garlic, *Palmaria palmata* (Dulse), *Chondrus crispus* (Carragaeen), *Fucus vesiculosus* (Bladder wrack), Shiitake (mycelium) and grapevine, vitamin A, vitamin B1, vitamin B9, vitamin C, vitamin E, vitamin F, and vitamin PP.

Depending on the family of ingredients, the preferred quantities are determined for:

plant oils (rapeseed oil, olive oil, grapeseed oil, evening primrose oil): 28 µg to 284 g/100 g or 100 ml trace elements: minerals (sodium, magnesium, calcium) and metals (zinc and iron): 40 µg to 400 µg/100 g or 100 ml

*Saccharomyces cerevisiae* yeasts or yeast extracts, preferably enriched with selenium: 28 µg to 280 µg/100 g or 100 ml mushrooms or mushroom extracts (Shiitake mycelium): 28 µg to 280 µg/100 g or 100 ml marine algal or their extracts (*Palmaria palmata* (Dulse), *Chondrus crispus* (Carrageen), and *Fucus vesiculosus* (Bladder wrack). 24 µg to 240 µg/100 g or 100 ml cold water fish oil and Copra: 28 µg to 280 µg/100 g or 100 ml plant extracts (samphire, garlic, and grapevine): 28 µg to 280 µg/100 g or 100 ml vitamins (A, B1, B9, C, E, F and PP): 32 µg to 320 µg/100 g or 100 ml For example, the composition in accordance with the invention may be advantageously prepared following the method of preparation describes in point A of the experimental part, or by any other methodology or technique known or developed by professionals in the field.

The invention may be implemented in any mammal, in particular in humans, adults, the elderly or in children. The composition of the invention has no known side effects and may be administered using various methods, which will depend on the subject. It can be taken as a single treatment or together with another nutritional or medical treatment.

Preferably, the daily amount of the composition to be administered, ingested or applied to an individual will ideally range from between 4 and 40 µg. Of course this amount may be subject to variations depending on the individual, her/his age, sex, health condition, etc. It is up to health professionals, dieticians and other specialists to adjust this amount according to the individual parameters taken into account.

The invention also concerns the use of a composition as defined for the preparation of a food or nutritional supplement or also a food additive.

By "food or nutritional supplement" it is understood to be in line with European directive 2002/46/CE of Jun. 10, 2002 (supplemented by Regulation CE 1925/2006 of Dec. 20, 2006) "foodstuffs, the purpose of which is to supplement the normal diet and which are concentrated sources of nutrients or other substances with a nutritional or physiological effect, alone or in combination, marketed in dose form, specifically in the form of capsules, pastilles, tablets, pills, and other similar forms as well as sachets of powder, ampoules of liquids, bottles that dispense drops, and other similar forms of liquids and powders designed to be taken in measured small unitary quantities".

This includes in particular, but not exclusively, vitamins and minerals, amino-acids, essential fatty-acids, fibers, various plants and plant extracts.

As indicated previously, the composition in accordance with the invention presents advantageous properties for regulating lipid metabolism.

One object of the invention in particular, concerns a method to control the lipid metabolism in subjects, including the administration, application, or ingestion of a composition as defined in this invention.

Thus the composition in accordance with the invention may be used to prepare a medicament or nutritional product designed to regulate lipid metabolism in humans and animals.

In particular, regulation of lipid metabolism consists of maintaining and/or regenerating the human or animal body by rebalancing and restimulating the general functions of said metabolism including:
stimulation of lipid consumption by the body and/or
reduction in plasma cholesterol and/or triglyceride levels,
and thus, the composition in accordance with the invention favors a return to health standards.

The medicament or nutritional product in accordance with the invention is also designed for treating or preventing metabolic syndrome, the formation of atheromatous plaques, hepatic steatosis, and/or cardiovascular diseases. The composition of the invention is especially effective in revitalizing lipid metabolism, and is thus particularly useful for patients affected by metabolic syndrome or who present a risk of developing metabolic syndrome. The term "metabolic syndrome" indicates a set of metabolic disturbances which strongly predisposes a patient to the development of cardiovascular diseases, including atherosclerosis and cerebral vascular accidents (CVA). Metabolic syndrome indicates a series of problems linked to poor body metabolism, and including certain disturbances characterized by abdominal obesity, an increase in triglycerides and/or cholesterol and/or arterial hypertension.

More in particular and according to a preferred embodiment of the invention, metabolic syndrome includes diseases related to weight control such as obesity, dieting, or stabilization of body mass.

One object of this invention is also the ability to stimulate the lipid consumption by the body by favoring an increase in oxidative metabolism and oxygen uptake. In particular, the composition as defined in this invention favors proper use of lipids by muscles.

Another object of this invention is an improvement in the endurance of a subject by administration or ingestion of the medicament or nutritional product in accordance with the invention. It was proven in the examples below that the medicament or nutritional product in accordance with the invention appreciably increases muscular motricity by improving muscle trophicity and contractility.

Surprisingly, the medicament or nutritional product in accordance with the invention contributes significantly to lowering plasma cholesterol and/or triglycerides levels (see examples).

Thus the invention concerns the use of the composition as defined for maintaining, and regenerating the body by rebalancing and restimulating the general function of lipid metabolism.

Additionally, the medicament or nutritional product in accordance with the invention unexpectedly allows a decrease in intestinal absorption of food lipids.

The composition in accordance with the invention may also be useful for animal or human nutrition.

Advantageously the composition in accordance with the invention may also be used in cosmetics, and in particular in skin care and revitalization.

According to the purpose of the composition, its final formulation may be adjusted by professionals in the field while following the disclosures found in this invention.

Thus, to foster a detoxifying action, certain ingredients of plant origin, like garlic and/or grapevine may be given preference in the composition, which improve bladder function as well as mushrooms such as the Shiitake mycelium, which have properties that detoxify liver cells, and also vitamin B1, which reinforces the Krebs cycle.

Vitamins A, E, C and the grapevine rich in OPCs (antioxidant Oligomeric Procyanidins) have anti free-radicals and anti-oxidant properties acting at all levels of oxidation. *Palmaria palmata, Chondrus crispus* and *Fucus vesiculosus* are rich in anti free-radicals and antioxidant pigments.

Detoxication and anti free-radicals allow the body to decrease the level of oxidized LDL and their elimination, to neutralize the active derivatives of oxygen.

To foster an increase in the permeability of cell membranes, preference is given to the presence of:
trace elements: calcium, sodium, magnesium, which allow an increase in assimilation and better elimination of cholesterol by regulating ionic channels; and/or
rapeseed, grapeseed, and cold water fish oils, the polyunsaturated fatty-acids (PUFA) of which contribute to the increase in membrane fluidity of the cell facilitating intra- and extra-cellular cholesterol exchanges In order to foster action on basal metabolism controlling a part of burning fuel and cellular vitality, the presence of the following components is given preference:
elements for basic cellular vitality: sodium, magnesium, calcium, iron,
*Palmaria palmata* and *Fucus vesiculosus* algas rich in trace elements: iodine contributes to regulating cellular fuel combustion
and vitamins A and PP.

To foster an action on the transformation of poly-unsaturated fatty-acids, the presence of the following components is given preference:
an oil vector component, which contains mono-unsaturated and poly-unsaturated fatty-acids which keep a good balance in the Omega-3/Omega-6 composition: olive oil, evening primrose oil, grapeseed oil, rapeseed oil;
zinc, iron and yeasts enriched with selenium, to stimulate elongases and desaturases.

As described above, the composition in accordance with the invention activates the consumption of lipids by the muscles and guarantees better muscle tone and better general energy. It also supports the increase in basal metabolism and weight control.

The invention is described in more detail through the examples below. Other aspects and advantages of this invention will become apparent upon reading these examples, which must be regarded as illustrative and nonrestrictive.

EXAMPLES

A) Manufacturing Process

The manufacturing process is modeled on the structure of the formula of the composition in accordance with the invention the architecture of which is the expression of a nutritional strategy which targets bringing the nutrients necessary or useful to the subsystems contributing directly or indirectly to the lipid metabolism.

Four principal subsystems constitute the base upon which the formulation and the ingredients of which it is made are listed. A formulation corresponds to each of these subsystems (or modules) which is made up as such and then combined with the other modules representing these subsystems.

1—Breakdown of Nutritional Strategy: 4 Modules $1^{st}$ module:
  detoxifying function: stimulation and regulation of hepatic cells, the gall bladder, and the small intestine. This function is the first preventive action and metabolic regulation of lipids and fighting free radicals by acting on the reduction of LDL oxidation $2^{nd}$ module:
  increase in permeability of the cell membranes $3^{rd}$ module:
  basal metabolism controlling one part of fuel combustion and cellular vitality $4^{th}$ module:
  regulation of lipid metabolism 2—Composition with Respect to Each of the Elements and Justification of the Presence of the Ingredients:

$1^{st}$ module: detoxification function and fighting free radicals:
  contributing at the level of plants, algae, and mushrooms: garlic, grapevine; shiitake mycelium; algae
  contributing to the vitamin plan: vitamins A, B1, C, E Garlic and Shiitake mycelium present detoxication properties for liver cells; as well as grapevine which improves bladder function, and vitamin B1 which reinforces the Krebs cycle.

Vitamins A, E, C and grapevine rich in OPCs have properties that fight free radicals and anti-oxidant properties that work at all levels of oxidation. Marine algae (*Palmaria palmata, Chondrus crispus,* and *Fucus vesiculosus*) are rich in pigments that fight free radicals and anti-oxidant pigments.

Detoxication and defense against free radicals allow the body to decrease the level of oxidized LDL, and to allow their elimination.

—$2^{nd}$ module: permeability of cell membranes:
    contributing to the vitamin plan: calcium, sodium, magnesium
    contributing to the vegetable or animal oil plan: rapeseed, grapeseed, copra and cold water fish oils Trace elements (calcium, sodium, magnesium) allow an increase in assimilation and better elimination of cholesterol by regulating ionic channels.

Oils (rapeseed, grapeseed, and cold water fish oils): PUFAs contribute to the increase in cell membrane fluidity facilitating intra- and extracellular exchanges of cholesterol.

$3^{rd}$ module: basal metabolism:
    contributing to the vitamin plan: calcium, sodium, magnesium, iron
    contributing to the algae plan: marine algae (*Palmaria* and *Fucus*)
    contributing to the vitamin plan: vitamins A, PP Calcium, sodium, magnesium, iron are elements of basic cellular vitality. Marine algae (*Palmaria palmata, Fucus vesiculosus*) are rich in trace elements (especially iodine) which contribute to the regulation of cellular combustion, as well as vitamins A and PP.

$4^{th}$ module: lipid metabolism:
    contributing to the vitamin plan: zinc, iron
    contributing to the vegetable oils and yeasts plan: olive, evening primrose, grapeseed, and rapeseed oils; enriched yeasts Oil vector components (olive, evening primrose, grapeseed, rapeseed oils) contain mono-unsaturated and poly-unsaturated fatty-acids that maintain a good balance in the composition of omega-3/omega-6.

Zinc, iron and yeasts enriched with selenium contribute to the stimulation of elongases and desaturases.

Support and Methods of Handling the Ingredients:

Ingredients are used in the dry form (powder, mineral salts, etc.) or in the liquid form (hydro-alcoholic or aqueous) in the following categories: minerals, plant extracts and similar (mushrooms, algae), vitamins.

Depending on the galenical form chosen, in terms of their liposolubility or hydrosolubility, the substances are processed in an oil/water or water/oil emulsion.

For dry forms, the different solutions corresponding to each module are impregnated on the medium in successive layers.

For the oily form, a 10% mix of 4 oils (rapeseed, olive, grapeseed, evening primrose oils) is used as a base to integrate the nutrients which make up the product.

Each element (trace elements, plants or similar, vitamins) is prepared separately.

The ingredient solution is prepared according to a process of successive addition of each ingredient while making sure the solution is homogenized at each stage. Between each new addition, the solution is submitted to dynamization.

Each module defined at the time of the nutritional strategy is thus constituted. They are then added one after another in accordance with the same method in order to arrive at the final solution.

Individual Properties of the Ingredients:

Oleum *Brassica Napus Oleifera*—Rapeseed Oil

98% constituted by fatty-acid triesters; the remaining 2% are rich in sterols and tocopherols (which is vitamin E).

98% constituted by fatty-acid triesters; 98% constituted of fatty-acid triesters; 98% constituted of fatty-acid triesters; It is 98% constituted by fatty-acid triesters. Rich in alpha-linoleic acid, poly-unsaturated omega-3 fatty-acids, in mono-unsaturated omega-6 fatty-acids (with an interesting ratio of omega-3:6 of 1:2.5); and only 6 to 8% of saturated fatty-acids.

Oleum Olea Europea—Olive Oil

Rich in oleic acid: mono-unsaturated fatty acids (>75%), Omega 6 (8%); olive oil contains vitamins A, E and K. The ratio of vitamin E/PUFA (Poly Unsaturated Fatty Acids) is the highest of all oils.

Oleum *Vitis vinifera*—Grapeseed Oil Linoleic acid balanced (alpha-linoleic and beta-linoleic), in oleic, palmitic and stearic acids. More than 70% Omega-6. Strongly unsaturated: the ratio of poly-unsaturated/saturated>5.

Oleum *Oenothera Biennis*—Evening Primrose Oil

Omega-6 balanced in linoleic acid, gamma-linoleic acid; in oleic and stearic acids.

Oleum Pisci Mare Fresca—Cold Water Fish Oil

Rich in Omega 3 fatty-acid. Omega 3 fatty acids reduce the triglyceride blood level by decreasing liver synthesis of triglycerides, by reducing VLDL in the blood and their high triglyceride content, which makes faster metabolism possible.

Omega-3s allow good membrane fluidity.

Natrum—Sodium

Sodium allows acid-base regulation and cellular metabolism in the body.

Sodium plays a deciding role in cellular depolarization which is at the origin of excitability and impulse conduction (in particular neuromuscular and cardiac), in the maintenance of acid-base balance, of osmotic pressure, in the balance of liquid and ionic exchanges in the body.

Magnesium—Magnesium

Magnesium is essential to the balance of the ionic channels. It acts as an enzymatic cofactor and modulates NA+ and K+ transport systems in all tissues; it is the physiological regulator of Calcium in the balance of cellular exchange.

Magnesium plays a role in establishing the different intracellular organelles. It establishes ribosomes that produce proteins, maintaining the production of energy by the mitochondria because they are essential to the synthesis of ATP molecules. This production of energy is the basis for all cell life mechanisms and the overall vitality of the body.

Magnesium is essential to the synthesis of proteins fundamental to cellular construction (certain amino-acids, DNA and RNA).

Calcarea—Calcium

Calcium is involved in many enzymatic reactions.

Calcium allows the transmission of information at the cellular level as a second messenger that induces the transmission of the nerve impulse, muscular contraction (by forming actinomyosin), stimulation of secreting cells (hormones like insulin), and the release of neurotransmitters.

The balance of calcium and magnesium in the intra- and extracellular liquids is essential to a good ion distribution.

Zincum-Zinc

Zinc intervenes in the activity of almost 200 enzymes (in particular in enzymatic systems like oxidoreductases, alcohol dehydrogenase, cytochrome reductase and SOD). Enzymes that are linked to Zinc are of significant importance in metabolic processes: glycolysis, pentose pathway, neoglucogenesis, lipid and fatty acid metabolism.

Zinc is a metal activator for the majority of the coenzymes necessary for energy metabolism.

Zinc plays a very important role in acid-base balance (carbonic anhydrase), in cellular differentiation, in the endogenous defense against free radicals.

Zinc is a hormonal cofactor (growth hormone, thyroid, adrenal cortex) and is essential to the transcription of the DNA chain (RNA-polymerase).

Zinc stabilizes cellular membranes and when coupled with thiol groups they thus prevent their reaction with iron, thus avoiding production of very unstable $H_2O_2$ free radicals. It intervenes particularly in the metabolism of Vitamin A (mobilization at the level of the liver, formation of retinol).

Ferrum-Iron

Component of the cytochromes, iron is essential to the detoxication, it is essential to the production of thyroid hormones.

Iron is an essential trace element, stored in the body in the form of ferritin and hemosiderin in the bone marrow, liver and spleen.

Iron plays a paramount role in the constitution of elements essential to life. It belongs to protein active sites (known as "iron proteins") which play an important role in the body: hemoglobin, myoglobin, and cytochromes.

*Saccharomyces Cerevisiae*-Yeasts (Enriched with Selenium)

The selenium active site of glutathion peroxidase has antioxidant properties.

*Cocos Nucifera*—Copra

Rich in fatty-acid. Intestinal regulator.

*Crithmum Maritimum*—Samphire

Very rich in minerals: zinc, iron, magnesium, copper, and manganese, in vitamins A, E, B1, and B2. Has a detoxifying action.

*Allium Sativum*—Garlic

Rich in vitamin C, zinc, and manganese: cholesterol-lowering action.

Garlic is characterized by the presence of original sulfur substances (allyl trisulphide, ajoene E) with beneficial effects on blood fluidity (reduces platelet aggregation) and blood cholesterol level (reduces the synthesis of triglycerides): of interest at the cardiovascular level.

*Palmaria Palmata*—Dulse

Very rich in provitamin A, good for hormonal control, and is rich in vitamin C, for fighting free radicals. Rich in essential amino-acids.

*Fucus Vesiculosus*—Bladder Wrack

Rich in fucosterol: a sterol which presents properties for lowering lipids like beta-sitosterol plant sterols.

It contains:
  trace elements: very rich in iodine and iron; selenium, manganese, copper, chromium, and zinc
  Vitamins: C, B1, B2, B6, B12
  active ingredients: alginates, phenolic compounds.

*Chondrus Crispus*—Carrageen (Irish Moss)

Rich in fatty-acids and balanced between omega-3 and omega-6, as well as unsaturated fatty-acids allowing the assimilation of cholesterol.

Rich in amino-acids, trace elements (particularly Iodine, Zinc and Iron); contains all the vitamins.

*Lentinus Edodes*—Shiitake (Mycelium)

Mycelium shiitake is very rich in amino-acids, trace elements and vitamins. It presents cholesterol-lowering and pro-immunizing properties.

*Vitis Vinifera*—Grapeseed (Grapevine)

Grapes are very rich in vitamins A, C, and the B group, as well as in mineral salts: manganese, potassium, calcium. Grapes drain the gall bladder and the liver. It is very rich in substances that fight free radicals.

Vitamin A (Retinol):

Retinol is esterified inside the intestinal cell, incorporated in chylomicrons, excreted in the lymph and joins the general circulation through the lymphatic channel. Vitamin A stabilizes cell membranes, biosynthesis and regulation of steroid hormones. The synthesis of certain proteins is dependent on vitamin A.

Vitamin B1 (Thiamin):

Vitamin B1 provides the cell in NADPH2 acid which is of paramount importance in the synthesis of lipids, sterols and fatty-acids. It is one of the essential links for neolipidogenesis.

Vitamin B9 (Folic Acid):

Vitamin B9 plays an important role in the metabolism of serine which is transformed into Acetyl-coenzyme A Vitamin C (Ascorbic Acid):

Vitamin C plays an important biochemical role at the initial stages of the lipid metabolism, in association with various hydroxylases. These microsomal cytochrome P 450-dependent hydroxylases act as a catalyst in the transformation of cholesterol into biliary acids.

Vitamin E (α-Tocopherol):

Alpha-tocopherol accompanies chylomicrons within the lymphatic channels until reaching general circulation In plasma, alpha-tocopherol is linked to several lipoprotein categories: to LDL which contains between 40 and 60% of tocopherols and to HDL which contains 34%. Its level is closely correlated with those of total lipids and cholesterol It has an antioxidant effect: buffering free radicals. It contributes to the formation and structure of membrane phospholipids, and has a stabilizing effect on cell membranes.

Vitamin F (Linoleic Acid):

Linoleic acid is an unsaturated fatty-acid essential for the synthesis and protection of lipids.

Vitamin PP/B3 (Niacin):

Nicotinic acid has a lipid-lowering effect (by stimulating the protein lipase or inhibiting lipolysis mediated by cyclic AMP in adipose tissue).

It is also a crucial agent in cell energy metabolism through its intervention in all redox phenomena in the body.

However, in the examples shown below, the composition in accordance with the invention was shown to produce unexpected synergistic effects, which are by far greater than those of the ingredients taken separately and which do not produce results sufficient to respond to the problem posed by the invention.

B) Preparation of the Composition in Accordance with the Invention

Example 1

In Liquid Form

A composition made up of the following ingredients was prepared in liquid form (drinks, spray . . . ):

For 100 g/100 ml of this composition in accordance with the invention comprises:
- from 7 µg to 700 µg of rapeseed oil, olive oil, grapeseed oil, evening primrose oil,
- from 10 µg to 1000 µg of sodium, magnesium, and calcium,
- from 10 µg to 1000 µg of zinc and iron,
- from 7 µg to 700 µg of yeasts or *Saccharomyces cerevisiae* yeast extracts, enriched with Selenium,
- from 7 µg to 700 µg of Shiitake (mycelium) [SIC],
- from 7 µg to 7 to 600 µg of Dulse (*Palmaria palmata*), Bladder wrack (*Fucus vesiculosus*), and Carrageen (*Chondrus crispus*),
- from 7 µg to 700 µg of samphire, from 6 µg to 600 µg of garlic and grapevine,
- from 8 µg to 800 µg of vitamins A, B1, B9, C, E, F, and PP and from 7 µg to 700 µg of cold water fish oil and Copra oil.

| Combined micronutrients | Per daily suggested dose | | | Per 100 ml | |
|---|---|---|---|---|---|
| Natrum | 0.05 | µg | 5 µg | 10 µg | 1000 µg |
| Magnesium | 0.05 | µg | 5 µg | 10 µg | 1000 µg |
| Calcarea | 0.05 | µg | 5 µg | 10 µg | 1000 µg |
| Zincum | 0.05 | µg | 5 µg | 10 µg | 1000 µg |
| Ferrum | 0.05 | µg | 5 µg | 10 µg | 1000 µg |
| *Saccharomyces cerevisiae* | 0.035 | µg | 3.5 µg | 7 µg | 700 µg |
| Oleum *Brassica napus oleifera* | 0.035 | µg | 3.5 µg | 7 µg | 700 µg |
| Oleum *Olea europea* | 0.035 | µg | 3.5 µg | 7 µg | 700 µg |
| Oleum *Vitis vinifera* | 0.035 | µg | 3.5 µg | 7 µg | 700 µg |
| Oleum *Oenothera biennis* | 0.035 | µg | 3.5 µg | 7 µg | 700 µg |
| Oleum pisci mare fresca | 0.035 | µg | 3.5 µg | 7 µg | 700 µg |
| *Cocos nucifera* | 0.035 | µg | 3.5 µg | 7 µg | 700 µg |
| *Vitis vinifera* | 0.03 | µg | 3 µg | 6 µg | 600 µg |
| *Allium sativum* | 0.03 | µg | 3 µg | 6 µg | 600 µg |
| *Crithmum maritimum* | 0.035 | µg | 3.5 µg | 7 µg | 700 µg |
| *Fucus vesiculosus* | 0.03 | µg | 3 µg | 6 µg | 600 µg |
| *Palmaria palmata* | 0.03 | µg | 3 µg | 6 µg | 600 µg |
| *Chondrus crispus* | 0.03 | µg | 3 µg | 6 µg | 600 µg |
| *Lentinus edodes* | 0.035 | µg | 3.5 µg | 7 µg | 700 µg |
| Retinol | 0.04 | µg | 4 µg | 8 µg | 800 µg |
| Thiamine | 0.04 | µg | 4 µg | 8 µg | 800 µg |
| Folic Acid | 0.04 | µg | 4 µg | 8 µg | 800 µg |
| Ascorbic Acid | 0.04 | µg | 4 µg | 8 µg | 800 µg |
| Tocopherol | 0.04 | µg | 4 µg | 8 µg | 800 µg |
| Linoleic Acid | 0.04 | µg | 4 µg | 8 µg | 800 µg |
| Nicotinamide | 0.04 | µg | 4 µg | 8 µg | 800 µg |
| Total | 1 µg | | 100 µg | 0.2 mg | 20 mg |

Galenical Medium (Water): QSP 100 ml

Example 2

In Oil Form

A composition made of the ingredients mentioned in Example 1 was prepared in oil form or as a fatty material as follows:

| Combined micronutrients | Per daily suggested dose | | | Per 100 ml | |
|---|---|---|---|---|---|
| Natrum | 0.05 | µg | 5 µg | 10 µg | 1000 µg |
| Magnesium | 0.05 | µg | 5 µg | 10 µg | 1000 µg |
| Calcarea | 0.05 | µg | 5 µg | 10 µg | 1000 µg |
| Zincum | 0.05 | µg | 5 µg | 10 µg | 1000 µg |
| Ferrum | 0.05 | µg | 5 µg | 10 µg | 1000 µg |
| *Saccharomyces cerevisiae* | 0.035 | µg | 3.5 µg | 7 µg | 700 µg |
| Oleum *Brassica napus oleifera* | 0.035 | µg | 3.5 µg | 7 µg | 700 µg |
| Oleum *Olea europea* | 0.035 | µg | 3.5 µg | 7 µg | 700 µg |
| Oleum *Vitis vinifera* | 0.035 | µg | 3.5 µg | 7 µg | 700 µg |
| Oleum *Oenothera biennis* | 0.035 | µg | 3.5 µg | 7 µg | 700 µg |
| Oleum pisci mare fresca | 0.035 | µg | 3.5 µg | 7 µg | 700 µg |
| *Cocos nucifera* | 0.035 | µg | 3.5 µg | 7 µg | 700 µg |
| *Vitis vinifera* | 0.03 | µg | 3 µg | 6 µg | 600 µg |
| *Allium sativum* | 0.03 | µg | 3 µg | 6 µg | 600 µg |
| *Crithmum maritimum* | 0.035 | µg | 3.5 µg | 7 µg | 700 µg |
| *Fucus vesiculosus* | 0.03 | µg | 3 µg | 6 µg | 600 µg |
| *Palmaria palmata* | 0.03 | µg | 3 µg | 6 µg | 600 µg |
| *Chondrus crispus* | 0.03 | µg | 3 µg | 6 µg | 600 µg |
| *Lentinus edodes* | 0.035 | µg | 3.5 µg | 7 µg | 700 µg |
| Retinol | 0.04 | µg | 4 µg | 8 µg | 800 µg |
| Thiamine | 0.04 | µg | 4 µg | 8 µg | 800 µg |
| Folic Acid | 0.04 | µg | 4 µg | 8 µg | 800 µg |
| Ascorbic Acid | 0.04 | µg | 4 µg | 8 µg | 800 µg |
| Tocopherol | 0.04 | µg | 4 µg | 8 µg | 800 µg |
| Linoleic Acid | 0.04 | µg | 4 µg | 8 µg | 800 µg |
| Nicotinamide | 0.04 | µg | 4 µg | 8 µg | 800 µg |
| Total | 1 µg | | 100 µg | 0.2 mg | 20 mg |

Galenical oil medium (including 10% of the oil mixture: rapeseed, olive, evening primrose, grapeseed oil): QSP 100 ml

Example 3

In Capsule Form

A composition made of the ingredients mentioned in Example 1 is prepared in the form of capsules or also designed in the dry form (tablets, capsules . . . ):

| Combined micronutrients | Per daily suggested dose | | | Per 100 g | |
|---|---|---|---|---|---|
| Natrum | 0.05 | µg | 5 µg | 10 µg | 1000 µg |
| Magnesium | 0.05 | µg | 5 µg | 10 µg | 1000 µg |
| Calcarea | 0.05 | µg | 5 µg | 10 µg | 1000 µg |
| Zincum | 0.05 | µg | 5 µg | 10 µg | 1000 µg |
| Ferrum | 0.05 | µg | 5 µg | 10 µg | 1000 µg |
| *Saccharomyces cerevisiae* | 0.035 | µg | 3.5 µg | 7 µg | 700 µg |
| Oleum *Brassica napus oleifera* | 0.035 | µg | 3.5 µg | 7 µg | 700 µg |
| Oleum *Olea europea* | 0.035 | µg | 3.5 µg | 7 µg | 700 µg |
| Oleum *Vitis vinifera* | 0.035 | µg | 3.5 µg | 7 µg | 700 µg |
| Oleum *Oenothera biennis* | 0.035 | µg | 3.5 µg | 7 µg | 700 µg |
| Oleum pisci mare fresca | 0.035 | µg | 3.5 µg | 7 µg | 700 µg |
| *Cocos nucifera* | 0.035 | µg | 3.5 µg | 7 µg | 700 µg |
| *Vitis vinifera* | 0.03 | µg | 3 µg | 6 µg | 600 µg |
| *Allium sativum* | 0.03 | µg | 3 µg | 6 µg | 600 µg |
| *Crithmum maritimum* | 0.035 | µg | 3.5 µg | 7 µg | 700 µg |
| *Fucus vesiculosus* | 0.03 | µg | 3 µg | 6 µg | 600 µg |
| *Palmaria palmata* | 0.03 | µg | 3 µg | 6 µg | 600 µg |

-continued

| Combined micronutrients | Per daily suggested dose | | Per 100 g | |
|---|---|---|---|---|
| Chondrus crispus | 0.03 μg | 3 μg | 6 μg | 600 μg |
| Lentinus edodes | 0.035 μg | 3.5 μg | 7 μg | 700 μg |
| Retinol | 0.04 μg | 4 μg | 8 μg | 800 μg |
| Thiamine | 0.04 μg | 4 μg | 8 μg | 800 μg |
| Folic Acid | 0.04 μg | 4 μg | 8 μg | 800 μg |
| Ascorbic Acid | 0.04 μg | 4 μg | 8 μg | 800 μg |
| Tocopherol | 0.04 μg | 4 μg | 8 μg | 800 μg |
| Linoleic Acid | 0.04 μg | 4 μg | 8 μg | 800 μg |
| Nicotinamide | 0.04 μg | 4 μg | 8 μg | 800 μg |
| Total | 1 μg | 100 μg | 0.2 mg | 20 mg |

Galenical medium (saccharose-lactose, saccharose-starch, fructo-oligosaccharides, sorbitol, etc.): QSP 100 g C) Study in Animals

Example 4

Demonstration of the Role of the Composition in Accordance with the Invention in Lowering Plasma LDL Levels FIG. 1 is a graph showing the differences in plasma levels of LDL (in mmolL$^{-1}$) in mice which do not express the leptin gene (indicated below as mouse ob/ob), submitted to a standard diet during 4 weeks, and divided into three groups: fenofibrate administered by gavage (F), composition in accordance with the invention incorporated into the diet (M), control (C). The p value represents the statistical degree of significance, as in FIG. 2.

In these genetically obese mice, which are 8 weeks old and at this age are already presenting mixed hyperlipidemia, the composition in accordance with the invention causes a significant decrease (p=0.007) in LDL-cholesterol as compared to control, whereas Fenofibrate was ineffective in reducing plasma LDL to this level.

Example 5

Figure 2:
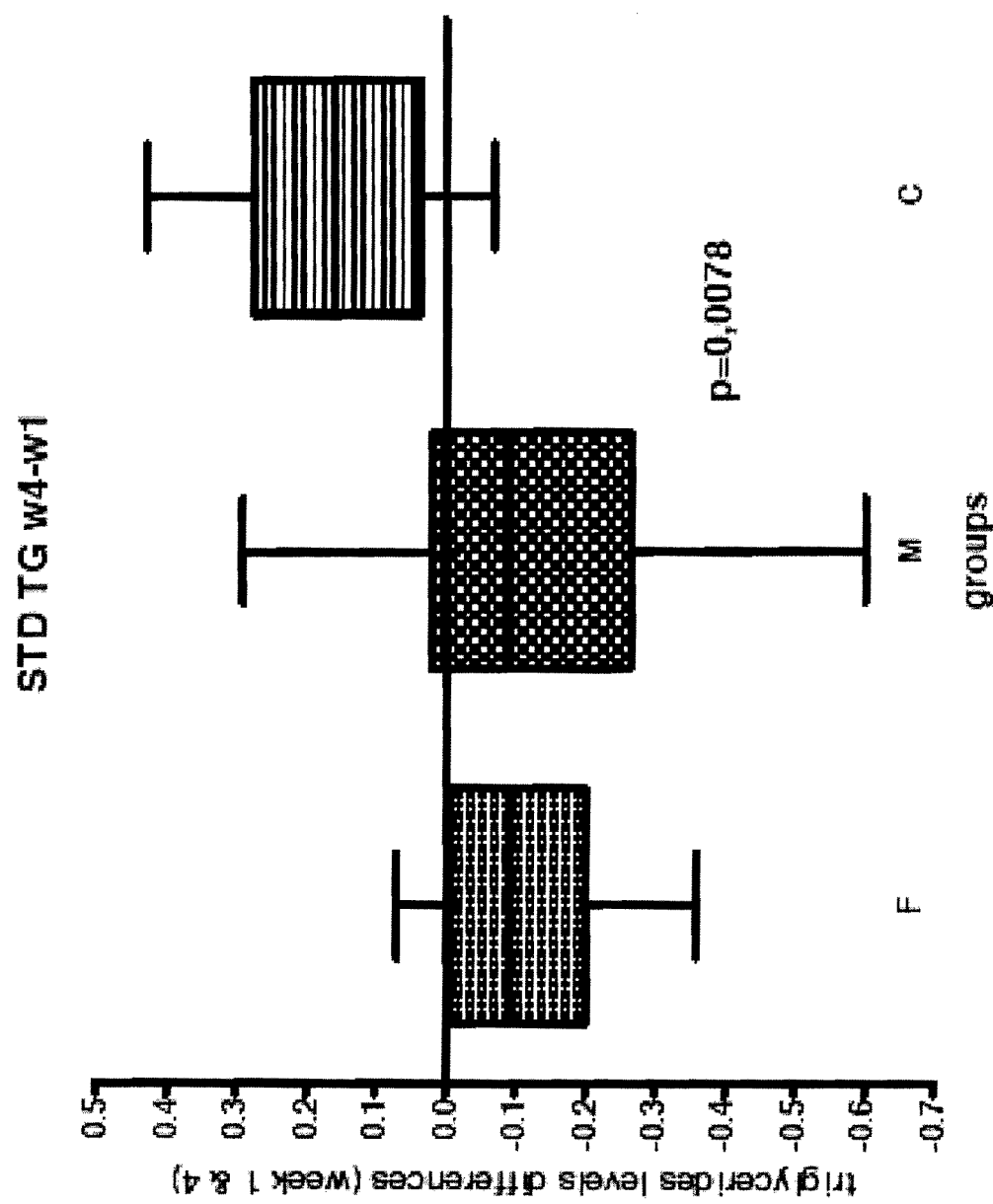
FIG. 2: Development of plasma LDL levels in ob/ob mice

Demonstration of the Role of the Composition in Accordance with the Invention in Lowering Plasma Triglyceride Levels FIG. 2 is a graph representing the differences in plasma triglyceride levels (in mmolL-1) of these same ob/ob mice submitted to a standard diet during 4 weeks, and divided into three groups as mentioned above.

The decrease in plasma triglyceride levels (TG) in the group receiving the composition in accordance with the invention (micronutrition) was identical to that of the mice having ingested the Fenofibrate (active medicament targeting triglycerides). The difference between the group treated with the composition in accordance with the invention and the control group is statistically significant (p=0.0078),

Example 6

Figure 3:
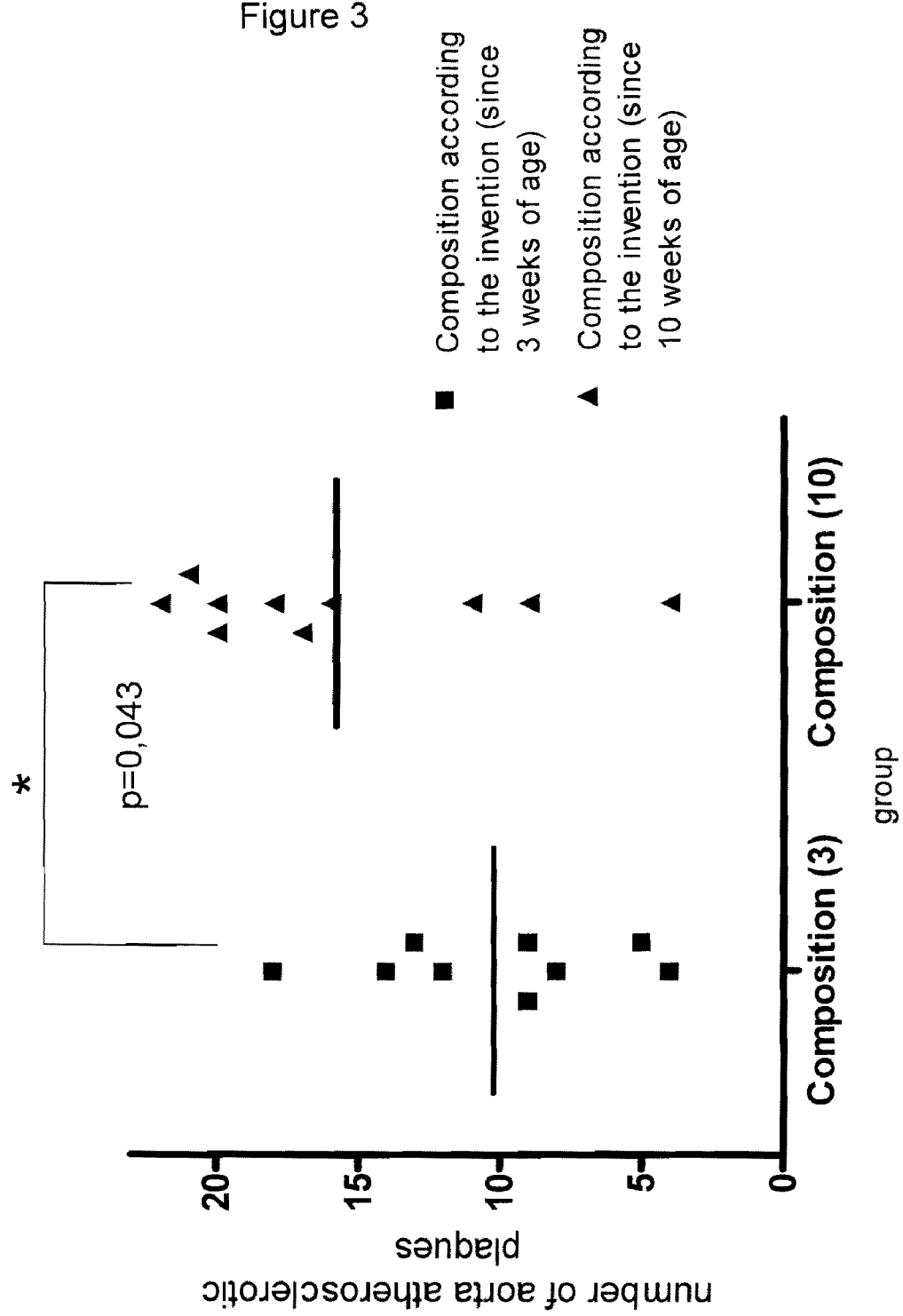
FIG. 3: Number of aortic atheromatous plaques in male APOE ko mice (at 12 months of age)

Demonstration of the Role of the Composition in Accordance with the Invention in the Prevention of the Formation of Atheromatous Plaques FIG. 3 shows the number of aortic atheromatous plaques in 12-month old APOE knock-out (ko) mice, treated beginning at 3 weeks of age versus those being treated beginning at 10 weeks of age.

These APOE ko mice, which lack the apo-lipoprotein E gene, spontaneously develop atheromatous plaques and thus constitute a good animal model for studying human atherosclerosis, and especially for testing the effectiveness of a treatment to prevent depositing of fat on vascular walls. These vascular atheromas block the arteries and are thus at the origin of cardiovascular diseases, including myocardial infarction when the coronary arteries of the heart are blocked. The formation of atheromatous plaques is a long process which progresses throughout life and starts at a very young age (atherosclerosis striae may appear as early as age 10 in humans).

The results of the experiment shown in FIG. 1 has the purpose of verifying whether the composition in accordance with the invention is able to reduce the formation of atheromatous plaques when it is administered at an early age. Two groups of APOE ko male mice, of the same age, received the composition in accordance with the invention added to food beginning at 3 weeks of age (immediately after weaning) for the first group, and beginning at 10 weeks of age (adulthood) for the second group. The two groups of mice always received the same amount of food containing the composition in accordance with the invention, and were sacrificed at age of 12 months. Once dissected, the aortas of mice treated beginning at 3 weeks of age contained a lower number of plaques than those found in the aortas of mice treated later (beginning at 10 weeks of age). Because this difference is statistically significant, we can thus affirm the effectiveness of the composition in accordance with the invention in the prevention of atherosclerosis. (The statistical threshold of significance is assumed for a value of p<0.05),

Example 7

Figure 4:
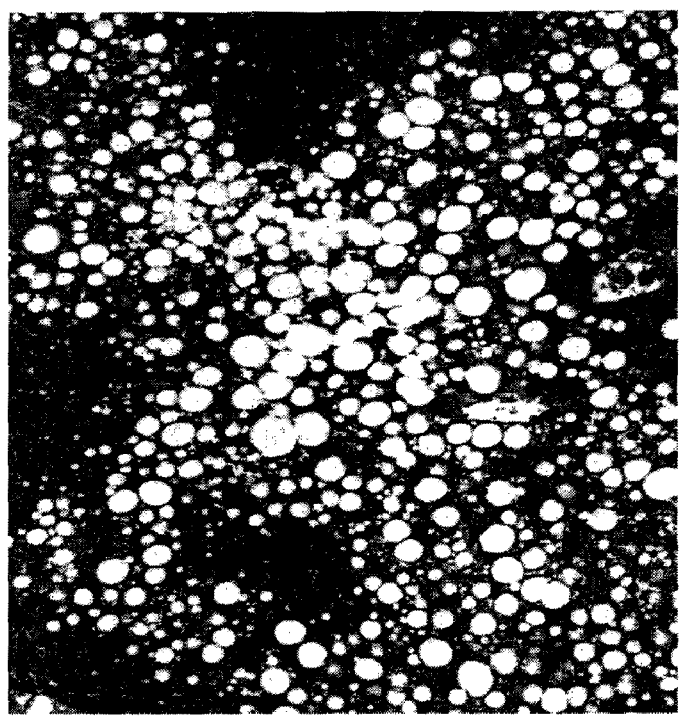
FIG. 4: Hepatic steatosis (paraffin-embedded liver tissue, HE, 10× magnification)
Figure 4:

Demonstration of the Role of the Composition in Accordance with the Invention in Preventing Hepatic Steatosis FIG. 4 shows the histological aspect of the liver of LDLr ko male mice after 10 months treatment with the composition in accordance with the invention versus the control (placebo/excipient).

The LDLr ko mice lack the LDL cholesterol receptor gene, and tend to accumulate fats at the liver level. Fat liver or hepatic steatosis can develop into cirrhosis which can develop further complications producing hepatic insufficiency (loss of physiological functions of the liver, requiring a liver transplant at the final stage) and/or develop into malignant liver cancer. Being able to prevent hepatic steatosis is thus of a great interest with regards to public health.

The purpose of the experiment whose result is represented by FIG. 4 is to check if the continuous administration of the composition in accordance with the invention can prevent in the long run the accumulation of fat in the liver, and the development of hepatic steatosis.

Two groups of LDLr ko male mice received beginning at 9 weeks of age, either the composition in accordance with the invention added to food for the first group, or the placebo also added to food for the second group. The two groups of mice always received the same amount of food and were sacrificed after 10 months of treatment. Once dissected, the livers of the treated mice did not contain any fat deposits and its histological aspect was completely normal, whereas the livers of the mice that received the placebo accumulated lipids in the form of vacuoles riddled with hepatic parenchyma. Given this obvious difference in the histological aspect, we can thus confirm the effectiveness of the composition in accordance with the invention in the prevention of hepatic steatosis.

Example 8

Figure 5:
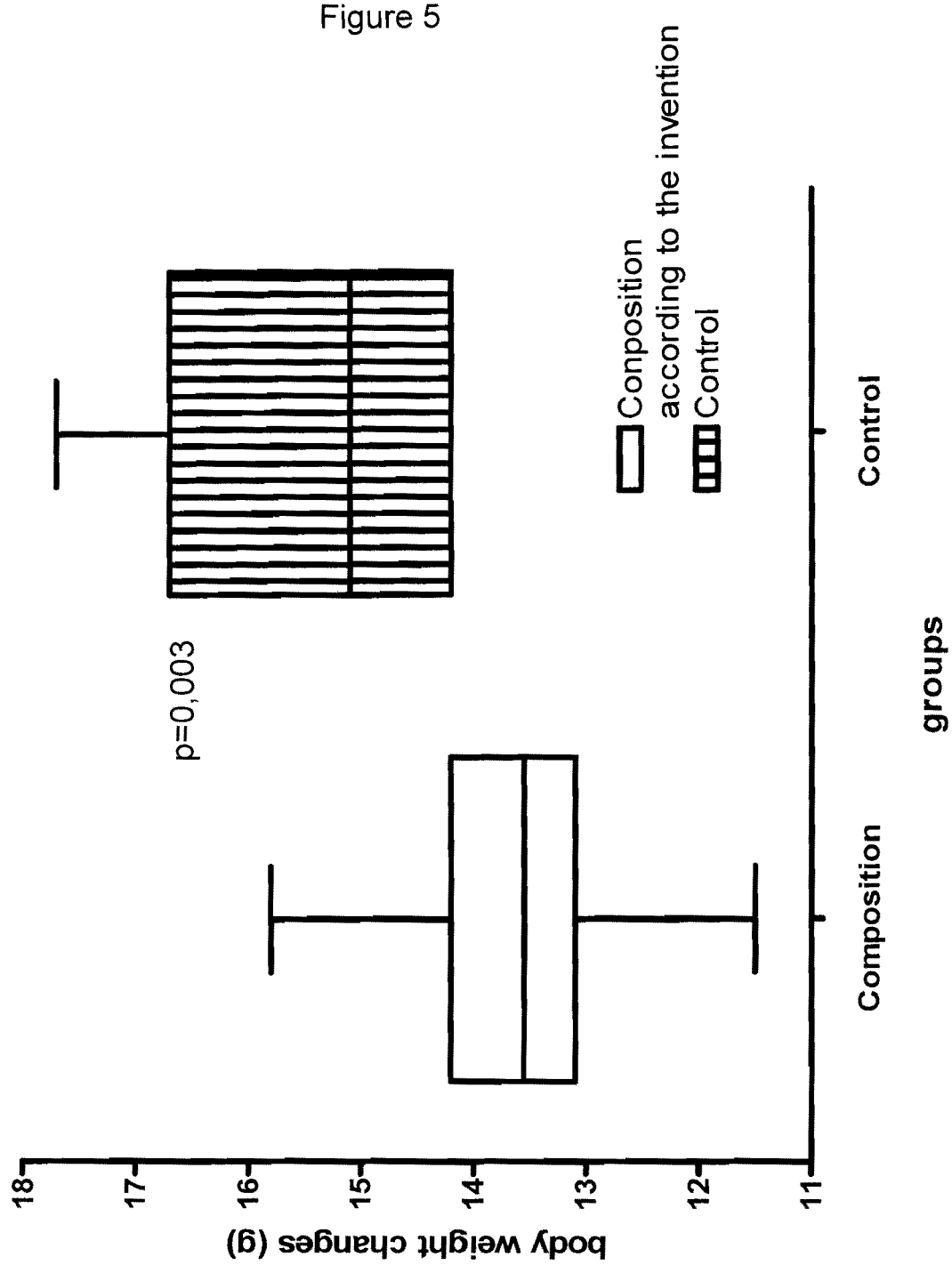
FIG. 5: Weight gain in OB/OB male mice receiving a diet rich in fats (week 4 vs. week 0)

Demonstration of the Role of the Composition in Accordance with the Invention in Prevention of Obesity by Limiting Weight Gain FIG. 5 shows weight gain in 4 weeks of OB/OB male mice receiving a diet enriched to contain 35% fat (the standard diet used for the preceding and following experiments contains 4.5% fat) and containing the composition in accordance with the invention versus the placebo.

OB/OB mice carry a spontaneous mutation of the leptin gene which controls appetite and induces satiety. These mice produce a non-functional mutated leptin gene are thus permanently incapable of satisfying and nourishing themselves. This eating behavioral disorder is at the root of an ever increasing tendency towards obesity and makes these mice a good model for study of the effectiveness of treatments targeting the control of body weight.

Given the extent of the progress towards obesity in the world, and its major complications for public health on the cardiovascular, respiratory, hepato-biliary, osteo-joint, reproductive, and psychosocial level, a treatment that is capable of controlling weight gain even with a fat-rich diet is of considerable medical interest.

The purpose of the experiment the result of which is shown in FIG. 3 is to verify whether adding the composition in accordance with the invention to a fat-rich diet can limit the weight gain induced by this diet.

Beginning at 9 weeks of age, two groups of OB/OB male mice received either the composition in accordance with the invention added to food for the first group, or the placebo also added to food for the second group. The two groups of mice always received the same amount of food, and were weighed before and after 1 month of treatment. The difference in weight between week 4 and week 0 showed a lower weight gain in the treated mice versus the control. Since this difference is statistically significant, we can thus confirm the effectiveness of the composition in accordance with the invention in the prevention of obesity by limiting weight gain and by controlling body weight.

Example 9

Demonstration of the Role of the Composition in Accordance with the Invention in Prevention of Obesity by Stabilizing Body Mass FIG. 6 is multiple and illustrates the limitation in weight gain in LDLr ko and APOE ko mice, as well as the stabilization of the body mass with a limitation in the size of adipocytes (fat cells) induced by the composition in accordance with the invention versus control.

The limitation in weight gain explained in Example 8 was confirmed in the long term for two other mouse strains LDLr KB (FIG. 6a) and the APOE KB (FIG. 6b) mentioned above, and allows us to confirm the effectiveness of the composition in accordance with the invention in the prevention of obesity. Nevertheless, it was important to verify that the limitation of weight gain does indeed take place through the stabilization of fat tissue.

Thus, the purpose of the experiments the results of which are shown in FIGS. 6c, 6d, 6e, and 6f is to document the effect of the composition in accordance with the invention on the body mass.

Figure 6A:
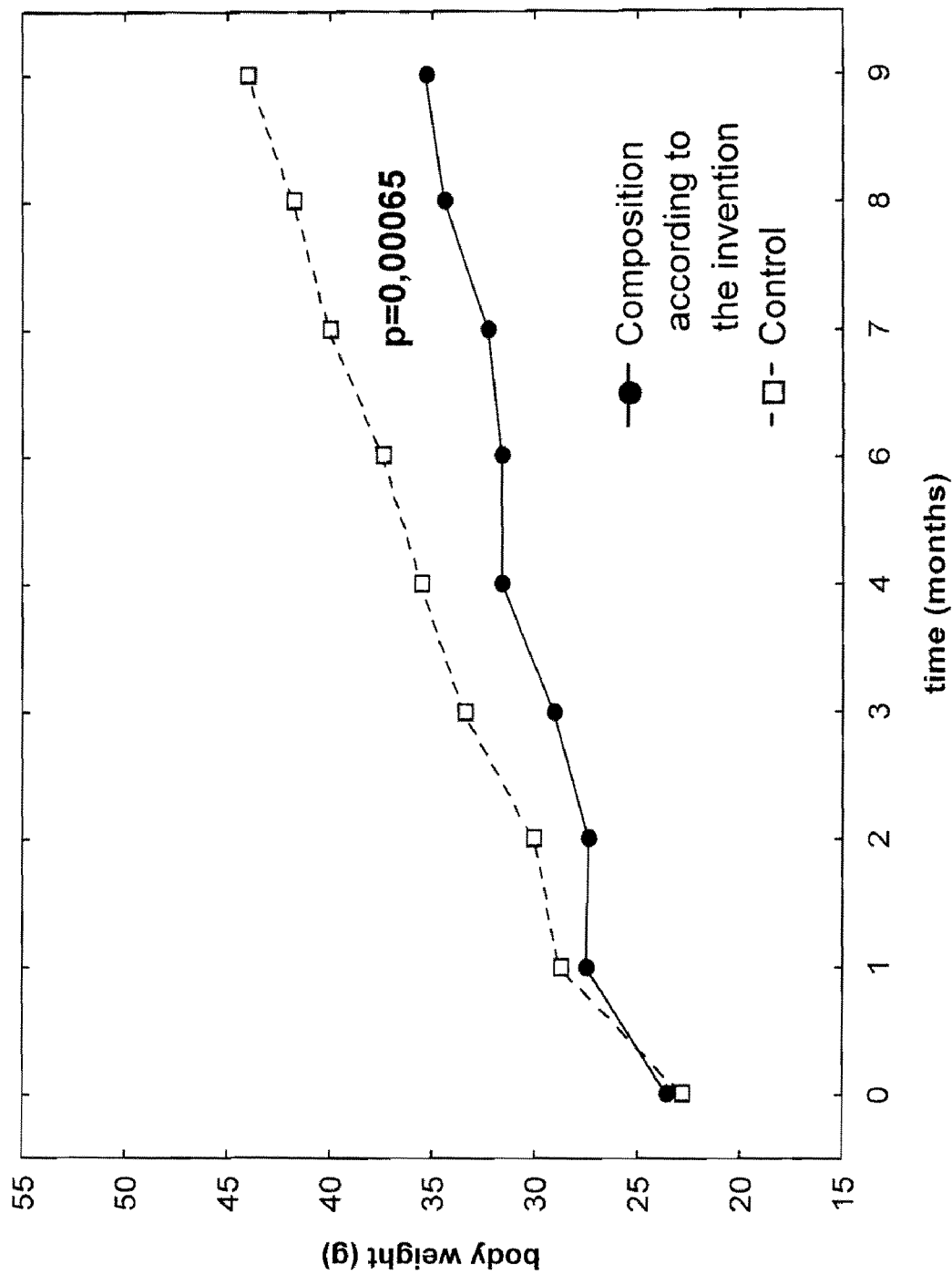
FIG. 6a: Weight development in LDLr (ko) male mice
Figure 6B:
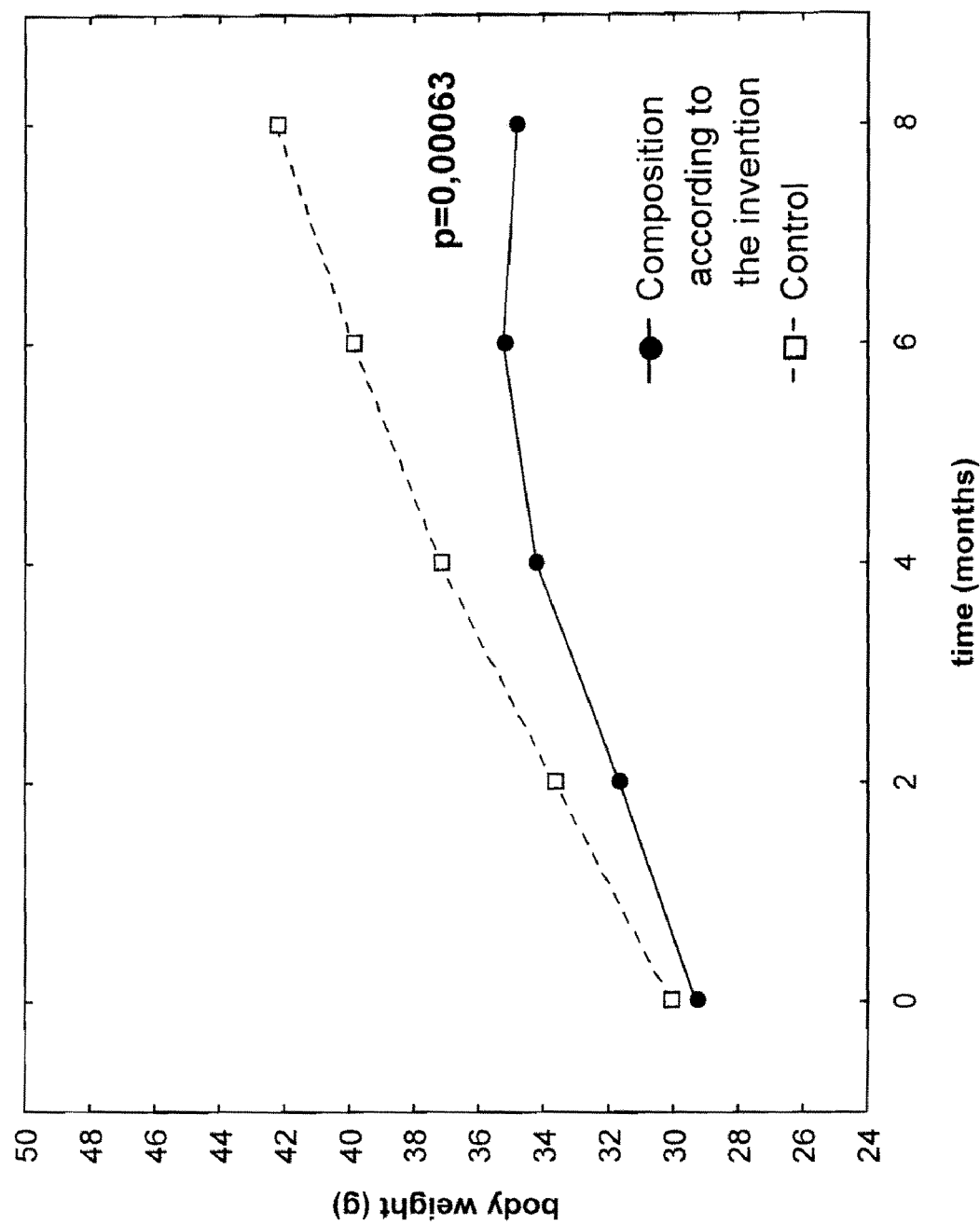
FIG. 6b: Weight development in APOEko male mice (treatment begun at 10 weeks of age)
Figure 6C:
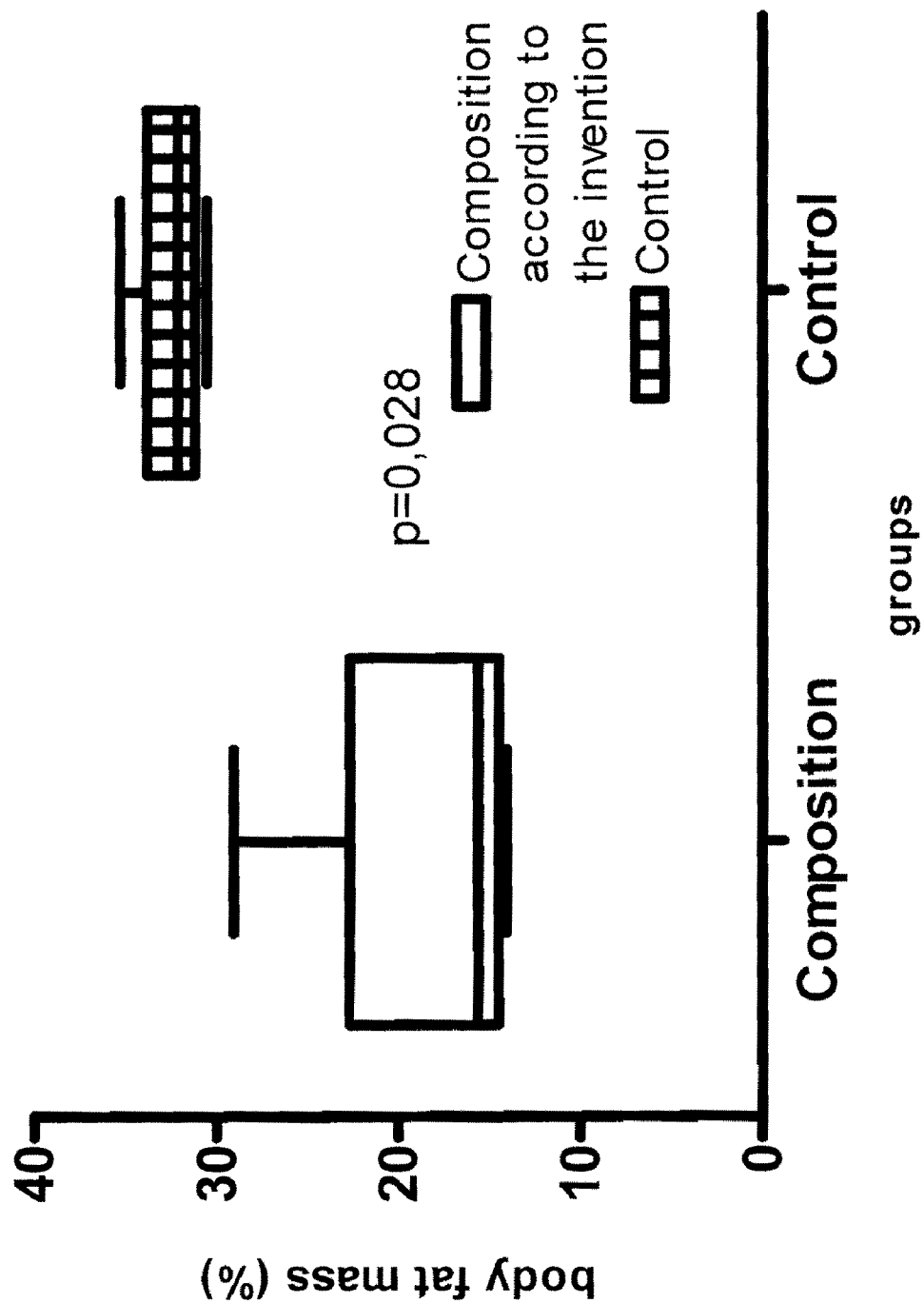
FIG. 6c: Percentage of fatty mass in LDLr (ko) male mice
Figure 6D:
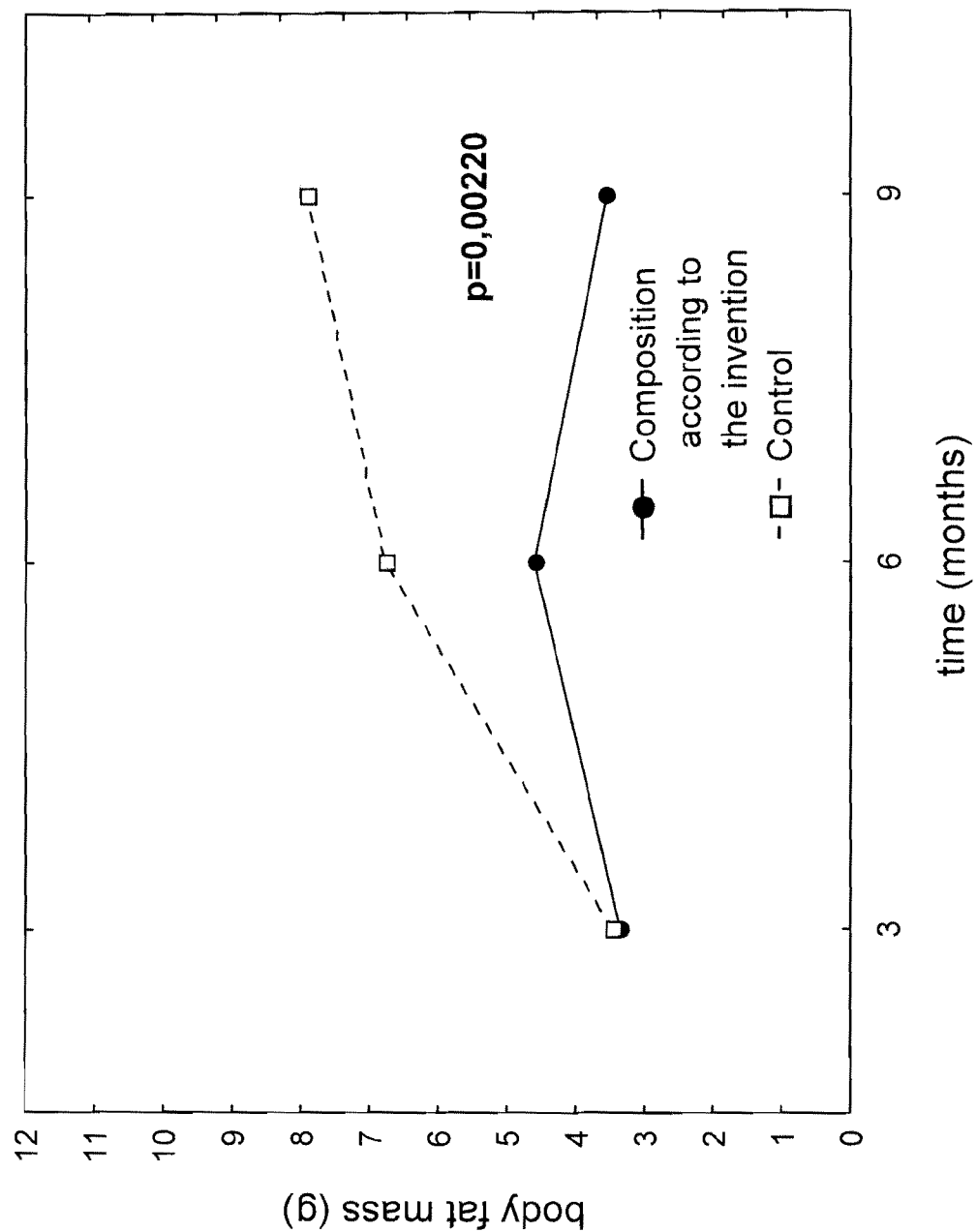
FIG. 6d: Development of fatty mass in APOEko male mice (treatment begun at 10 weeks of age)
Figure 6E:
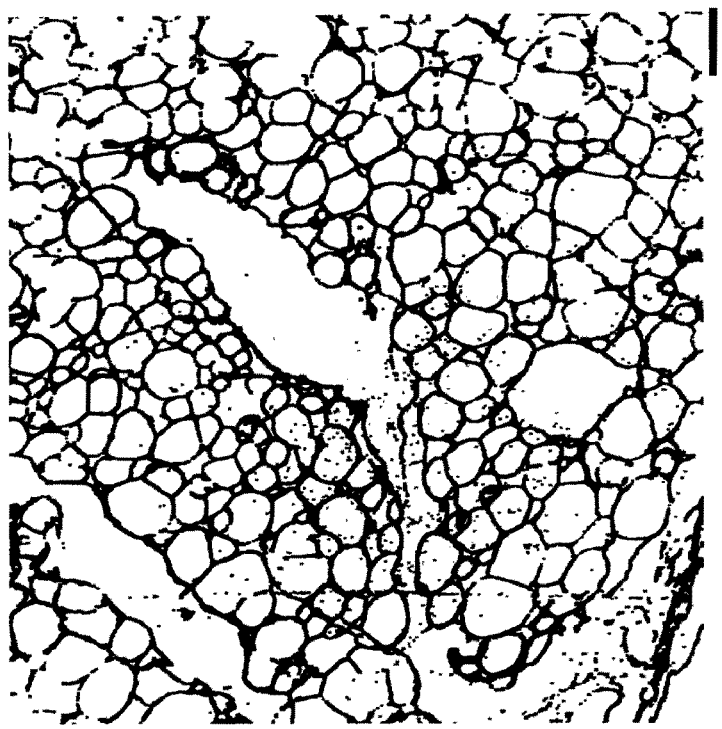
FIG. 6e: Epididymal white adipose tissue in LDLr ko male mice (paraffin-embedded tissue, HE, 5× magnification)
Figure 6E:
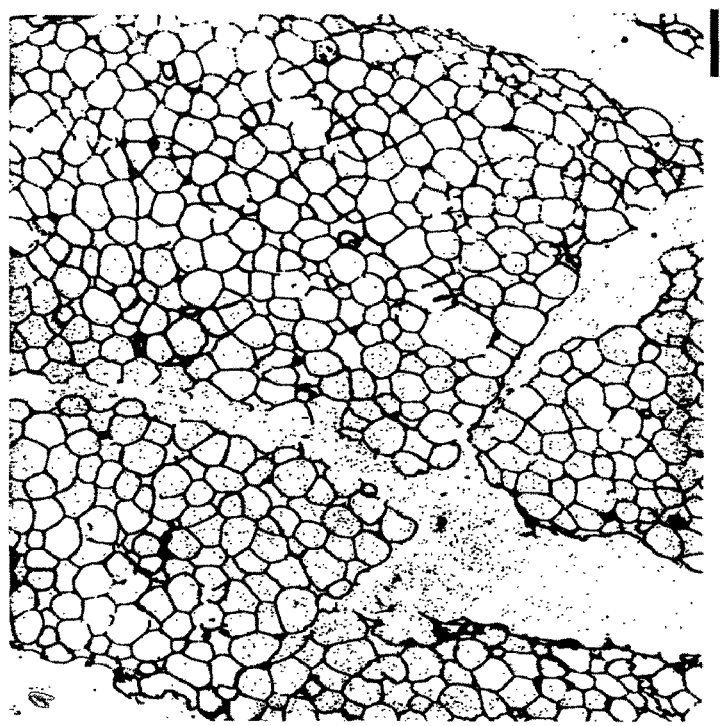
Figure 6F:
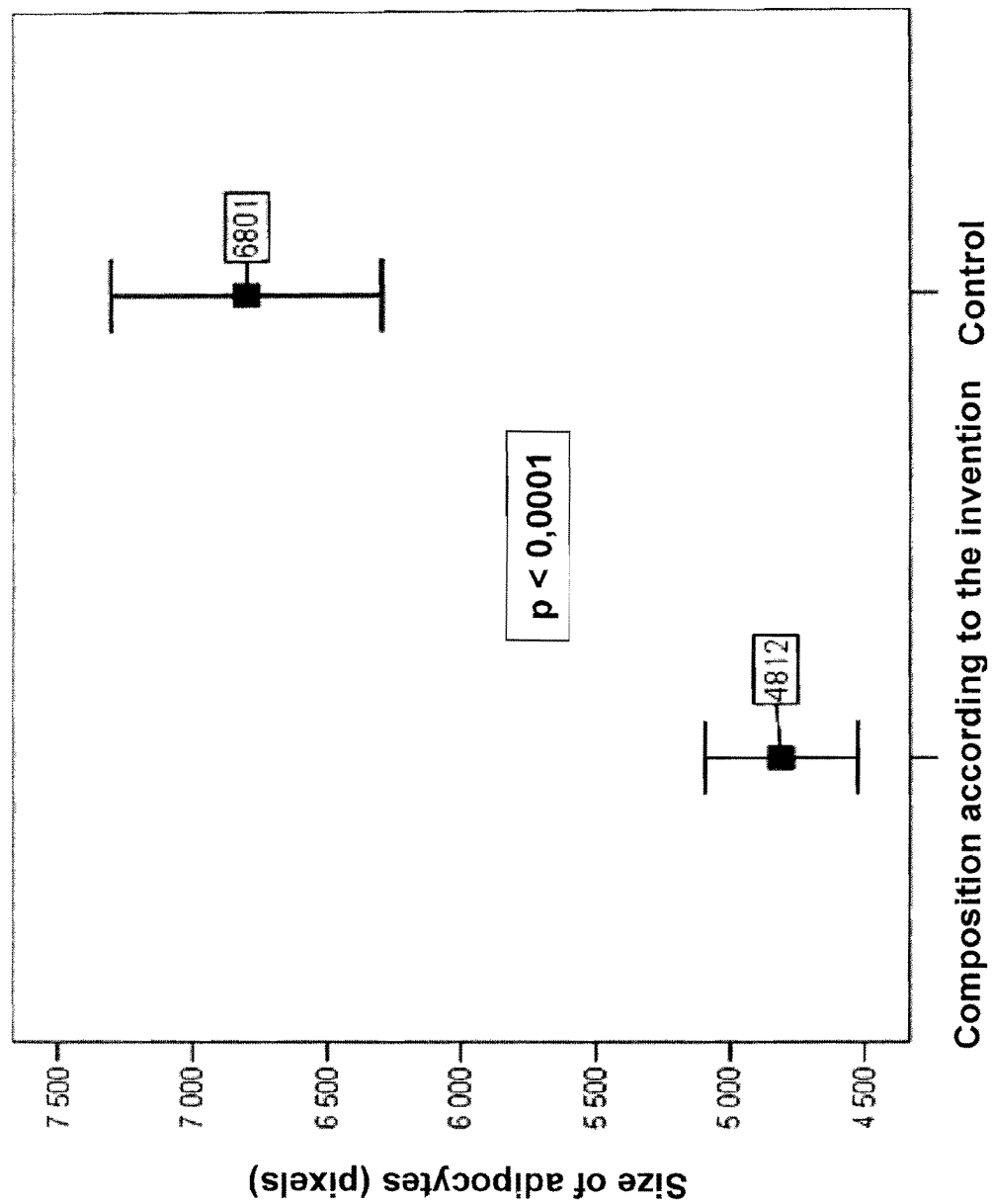
FIG. 6f: Average size of adipocytes in LDLr ko male mice

Two groups of LDLrko male mice received beginning at 2 months of age, either the composition in accordance with the invention added to the food for the first group, or the placebo also added to the food for the second group. Idem for the experiment with APOE ko male mice. The two experimental groups for each mouse strain always received the same quantity of food and were scanned in EchoMRI after 10 months of treatment in the LDLr ko mice, and after 3, 6 and 9 months of treatment in APOE ko mice. FIG. 6c shows that body mass in LDLr ko mice in the treated group is lower than in the control group at the end of the treatment. Moreover, FIG. 6d shows an unquestionable effect of the composition in accordance with the invention on the evolution of fat mass in the long term. Indeed, in FIG. 6d it is easy to verify that the body mass remains stable in treated APOE ko mice, while it increases in the untreated mice (control). Since these differences are statistically significant, we can thus confirm the effectiveness of the composition in accordance with the invention in the prevention of obesity by stabilizing body mass. FIGS. 6e and 6f also support this effect by showing smaller fat cells (constituting the fat mass) at the histological level, and thus containing less fat, in LDLr ko treated mice versus the control (FIG. 6e). FIG. 6f shows that the average size of fat cells in the LDLr ko treated mice is much lower than that of the cells of the untreated group (control). The difference is here is also statistically significant, and allows us to confirm that the composition in accordance with the invention stabilizes the fat mass by limiting the accumulation of fat in fat cells.

Example 10

Demonstration of the Role of the Composition in Accordance with the Invention in the Increase in Oxygen Uptake FIG. 7 is multiple, and illustrates the increase in oxygen uptake in OB/OB mice (FIGS. 7a, b and c), APOE ko (FIGS. 7d, e, f, and g) and LDLr ko (FIG. 7h) induced by the composition in accordance with the invention versus the control.

The use of lipids by the body as an energy substrate involves their oxidation, and thus oxygen uptake. According to the observations in Example 6 that shows a limitation of fat storage by the composition in accordance with the invention, FIG. 7 shows that this composition increases oxygen uptake used for lipid oxidation, which instead of being stored, are thus eliminated.

Figure 7A:
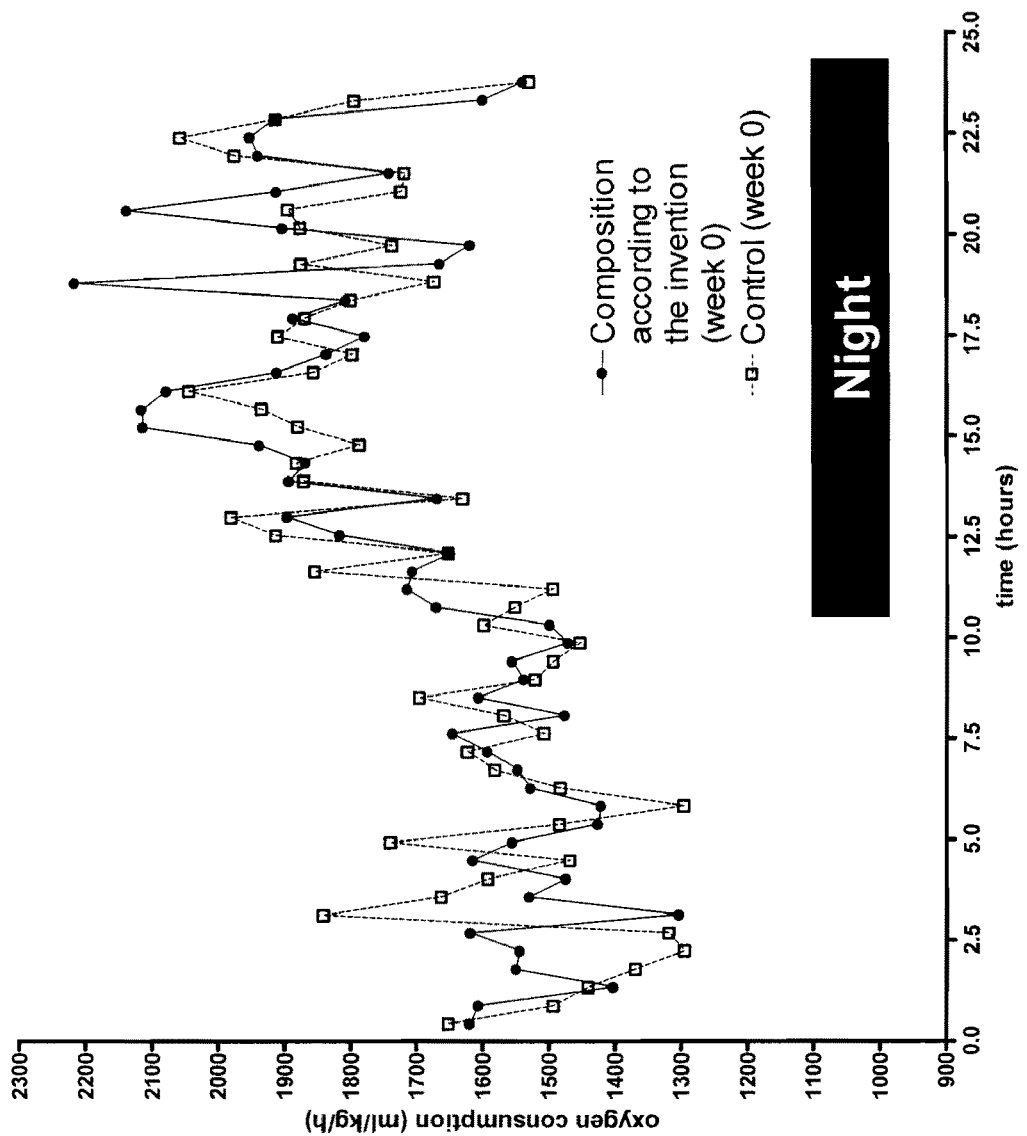
FIG. 7a: Oxygen uptake curve in OB/OB male mice (week 0)
Figure 7B:
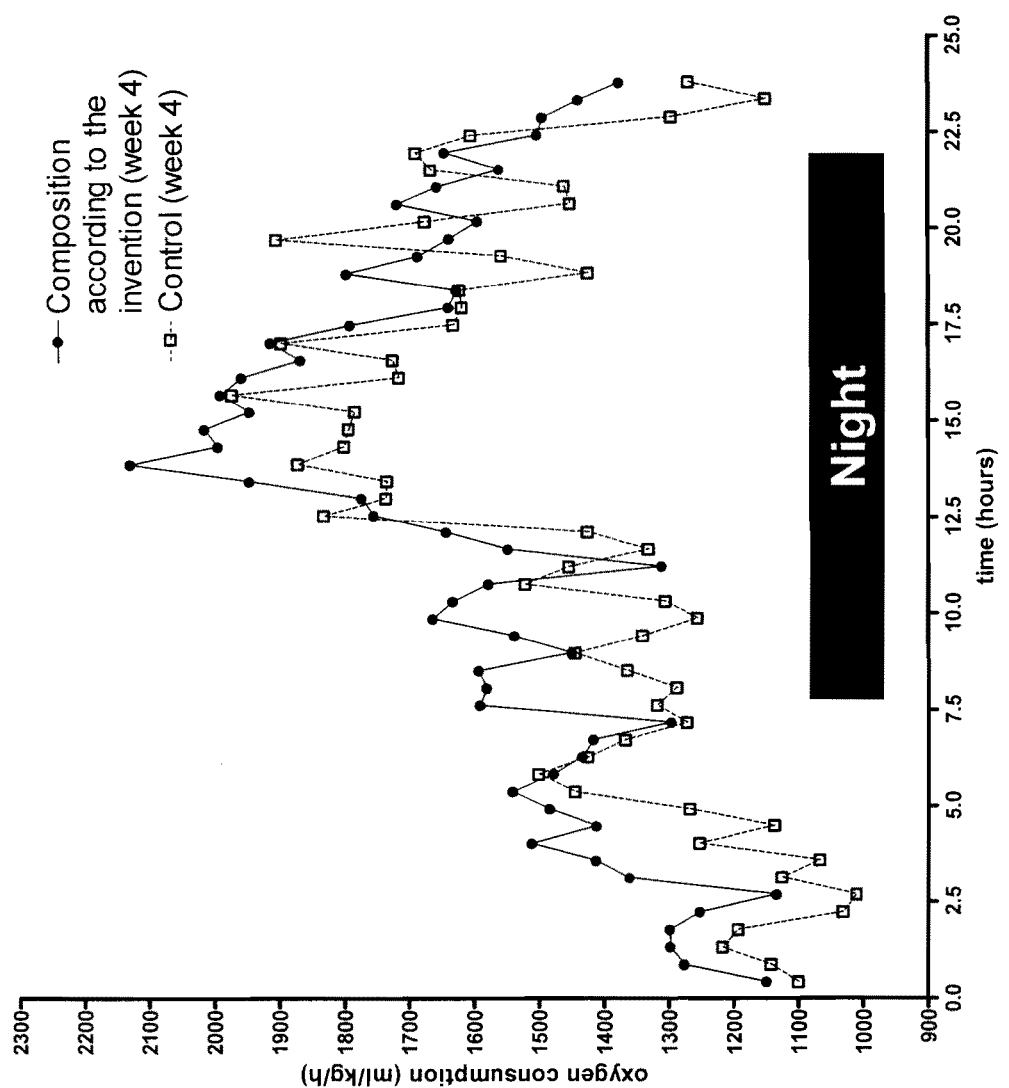
FIG. 7b: Oxygen uptake curve in OB/OB male mice (week 4)
Figure 7C:
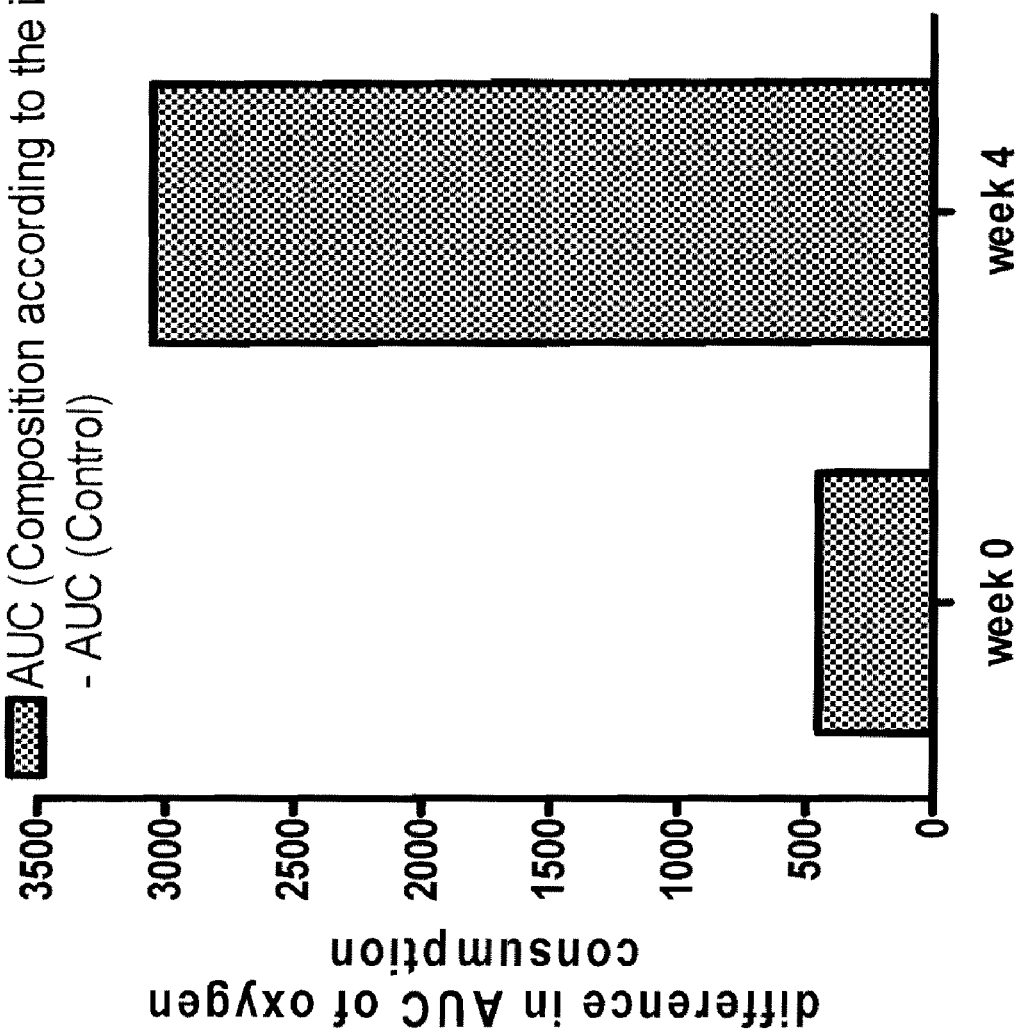
FIG. 7c: Difference of area under the curve (AUC) of oxygen uptake in OB/OB male mice

Two groups of OB/OB male mice received beginning at 2 months of age, either the composition in accordance with the invention added to food for the first group, or the placebo also added to food for the second group. Idem for the experiment with LDLrko and APOE ko male mice. The two experimental groups for each mouse strain always received the same amount of food, and remained in a calorimetric cage before and after 1 month of treatment for OB/OB mice, after 5 months of treatment for LDLr ko mice, and after 3, 6, and 9 months of treatment for APOE ko mice. FIG. 7a shows oxygen uptake curves recorded during the 24-hour stay of mice in the individual calorimetric cages, especially equipped to measure this parameter. The curves represented on this figure were recorded before beginning treatment with the composition in accordance with the invention. As shown in FIG. 5a, the oxygen uptake curves of the two experimental groups before treatment overlap. After 1 month of treatment, the oxygen uptake curve of the group treated with the composition in accordance with the invention rises in comparison to the curve from the control group, as shown in FIG. 7b, and thus reveals an increase in oxygen uptake induced by the composition in accordance with the invention. This observation is very well illustrated in FIG. 7c which shows the surface difference under the curve of oxygen uptake of the treated group and that of the control group at week 0 (before treatment) and week 4 (after 1 month of treatment). The surface difference under the curve between the treated and control group was thus multiplied by 6 in favor of an upward move to the top of the curve of the treated group compared to that of the control group.

This increase in oxygen uptake induced by the composition in accordance with the invention was confirmed for the two other APOE ko and LDLr ko mouse strains.

Figure 7D:
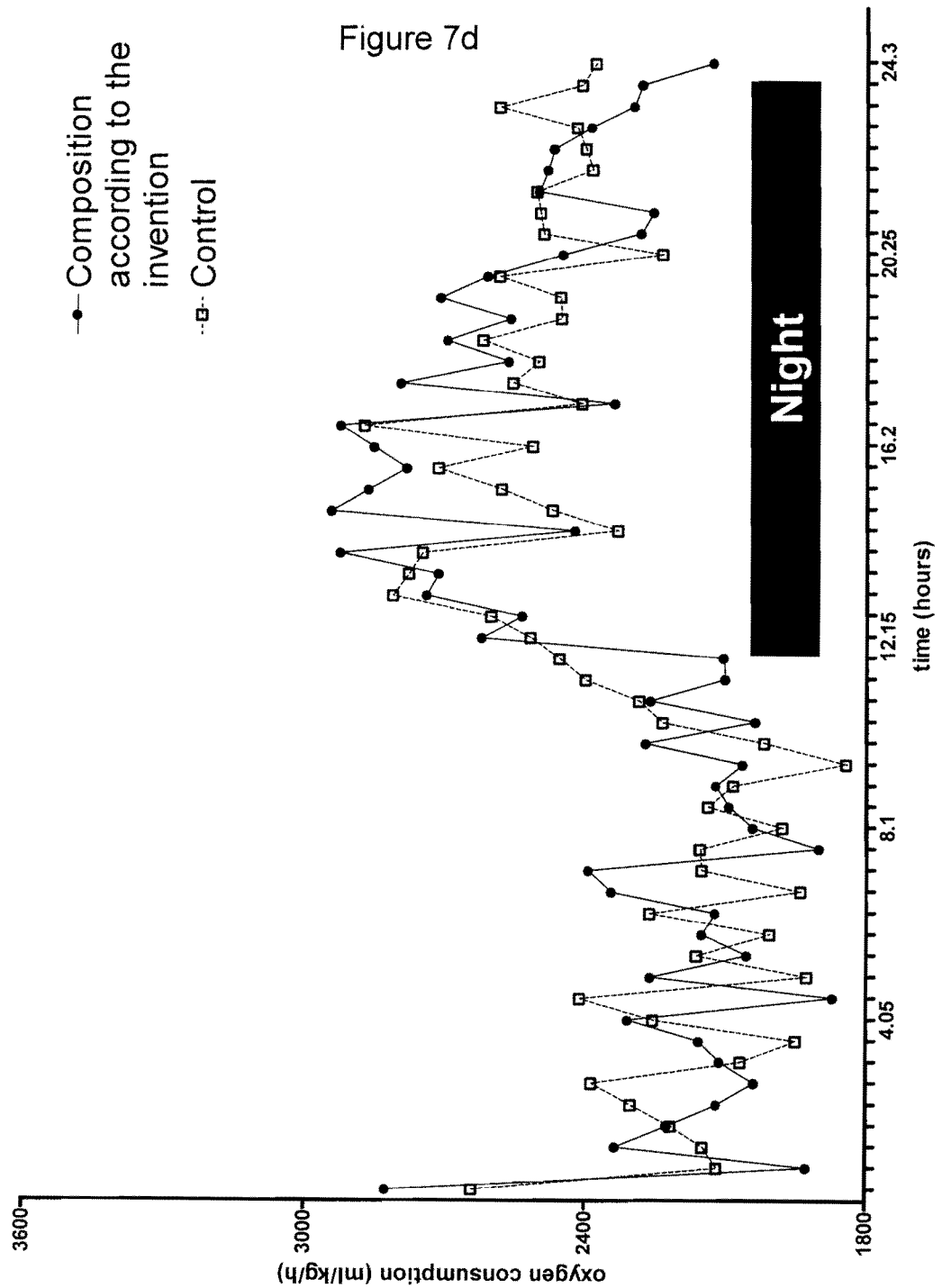
FIG. 7d: Oxygen uptake at 3 months in APOEko male mice (treatment begun at 10 weeks of age)
Figure 7E:
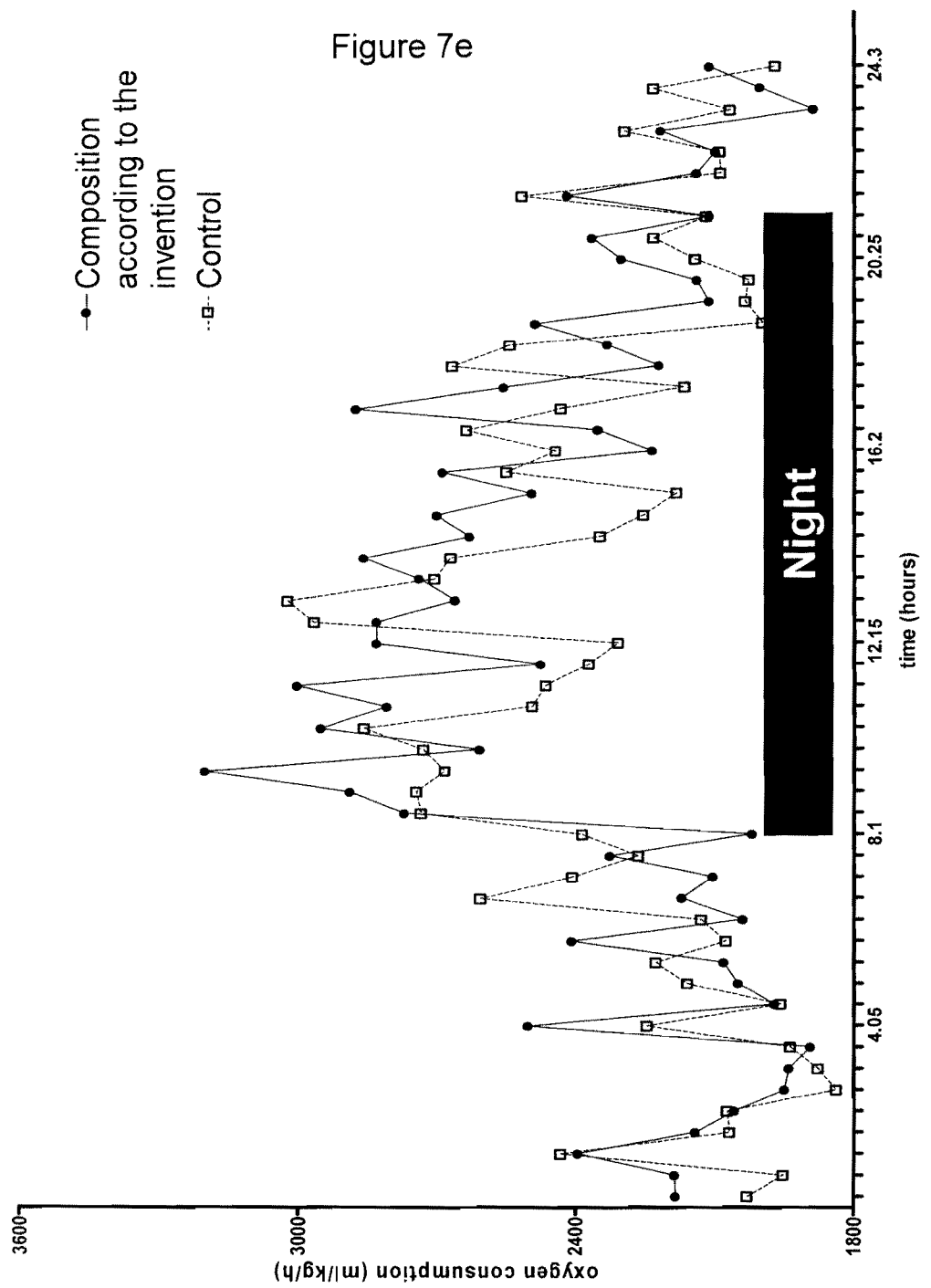
FIG. 7e: Oxygen uptake at 6 months in APOEko male mice (treatment begun at 10 weeks of age)
Figure 7G:
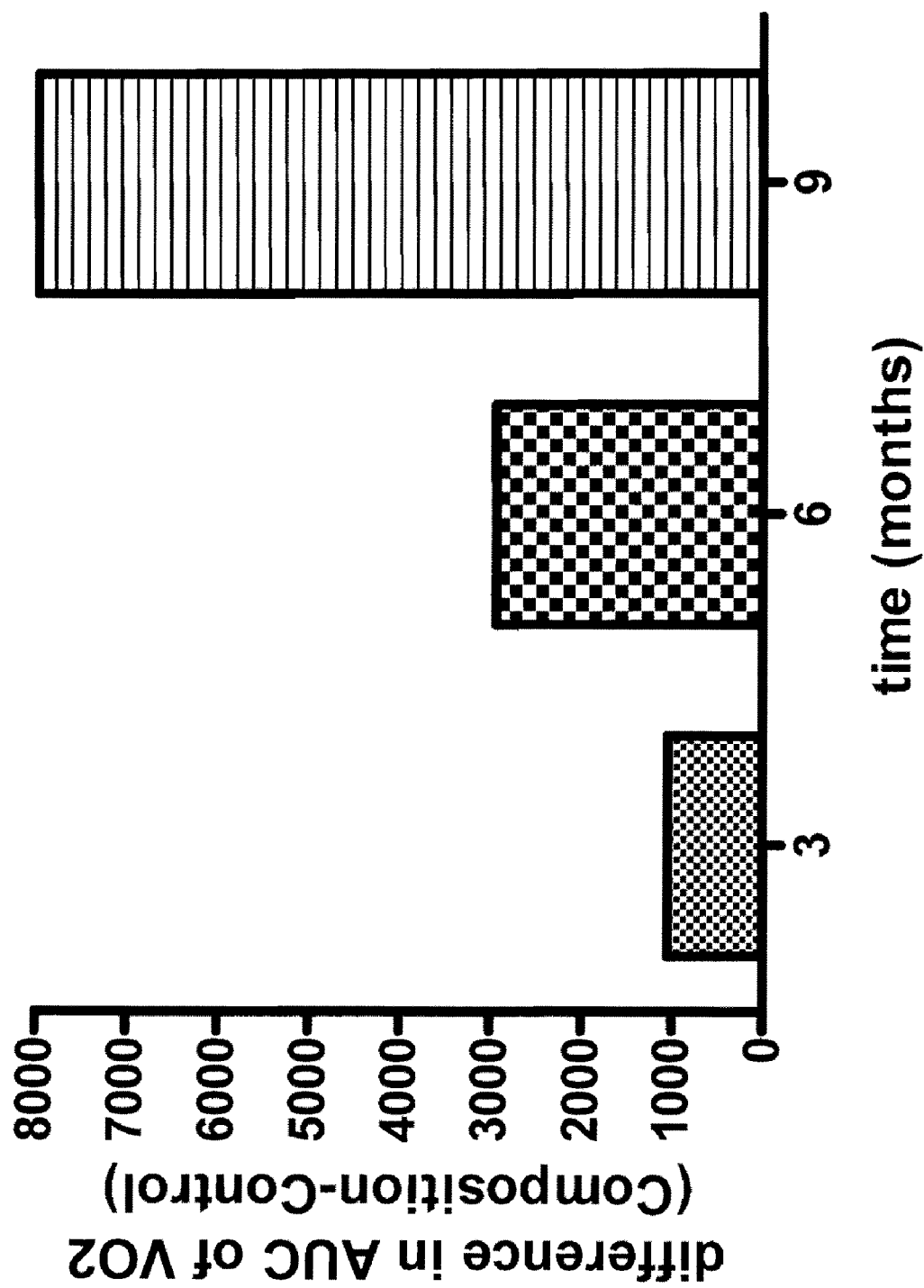
FIG. 7g: Difference of area under the curve (AUC) of oxygen uptake in APOE ko male mice (treatment begun at 10 weeks of age)
Figure 7H:
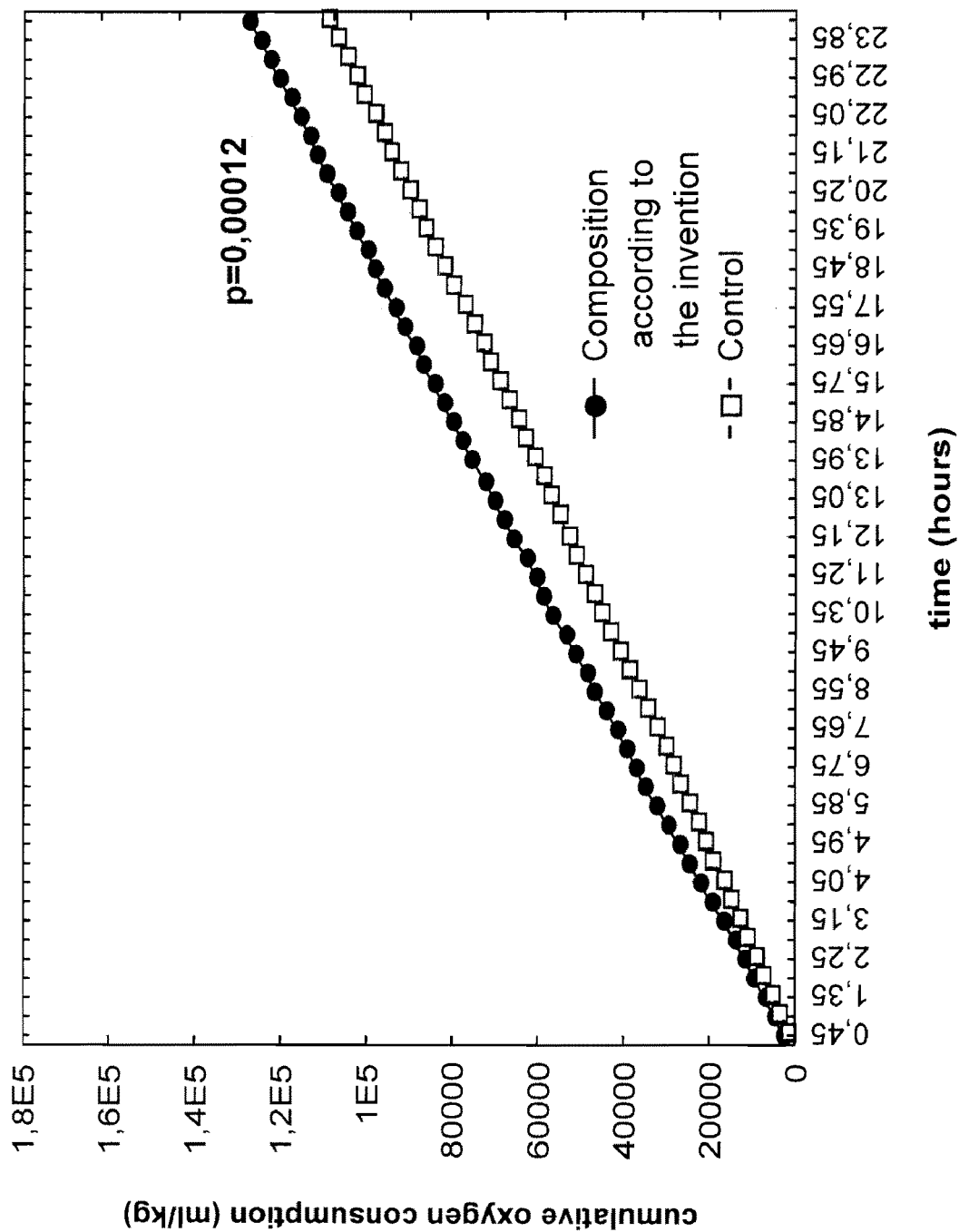
FIG. 7h: Cumulative oxygen uptake in LDLr ko male mice

In the same way that FIGS. 7a and b, FIGS. 7d, e, and f represent the curves of oxygen uptake of the APOE ko mice groups constituting the control group and the group treated with the composition in accordance with the invention after 3 months (FIG. 5d), 6 months (FIGS. 5e), and 9 months (FIG. 7O of treatment. In these Figures, a progressive and constant upward shift may be seen in the oxygen uptake curve of the treated group compared to that of the control group, throughout these months of treatment. Like FIG. 7c, FIG. 7g effectively shows this shift systematically widening the gap between the surface under the oxygen uptake curve of the treated group and that of the control group which is thus multiplied by 3, between the 3rd and 6th month, then by 8 by the 9th month. Lastly, FIG. 7h shows that for LDLr ko mice, the composition in accordance with the invention also increases their oxygen uptake. Indeed, this Figure shows the curves of cumulative consumption of oxygen during 24 hours of the treated and control mice groups. The curve of the treated group indicates that the oxygen uptake of this group is higher than that of the control group control. Since this difference is statistically significant, we can thus affirm that the composition in accordance with the invention increases oxygen consumption in the body.

Example 11

Figure 8B:
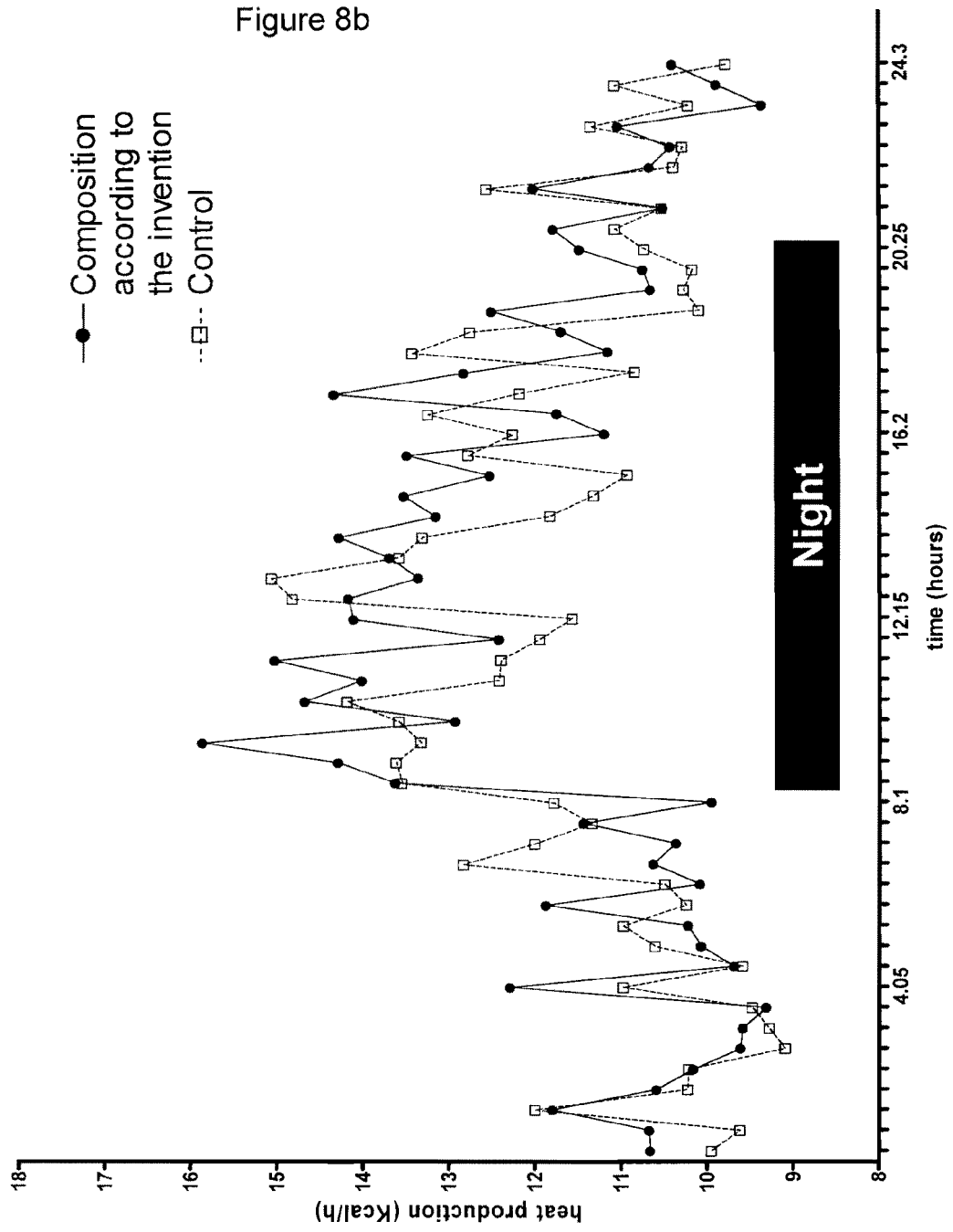
FIG. 8b: Heat production at 6 months in APOEko male mice (treatment begun at 10 weeks of age)
Figure 8D:
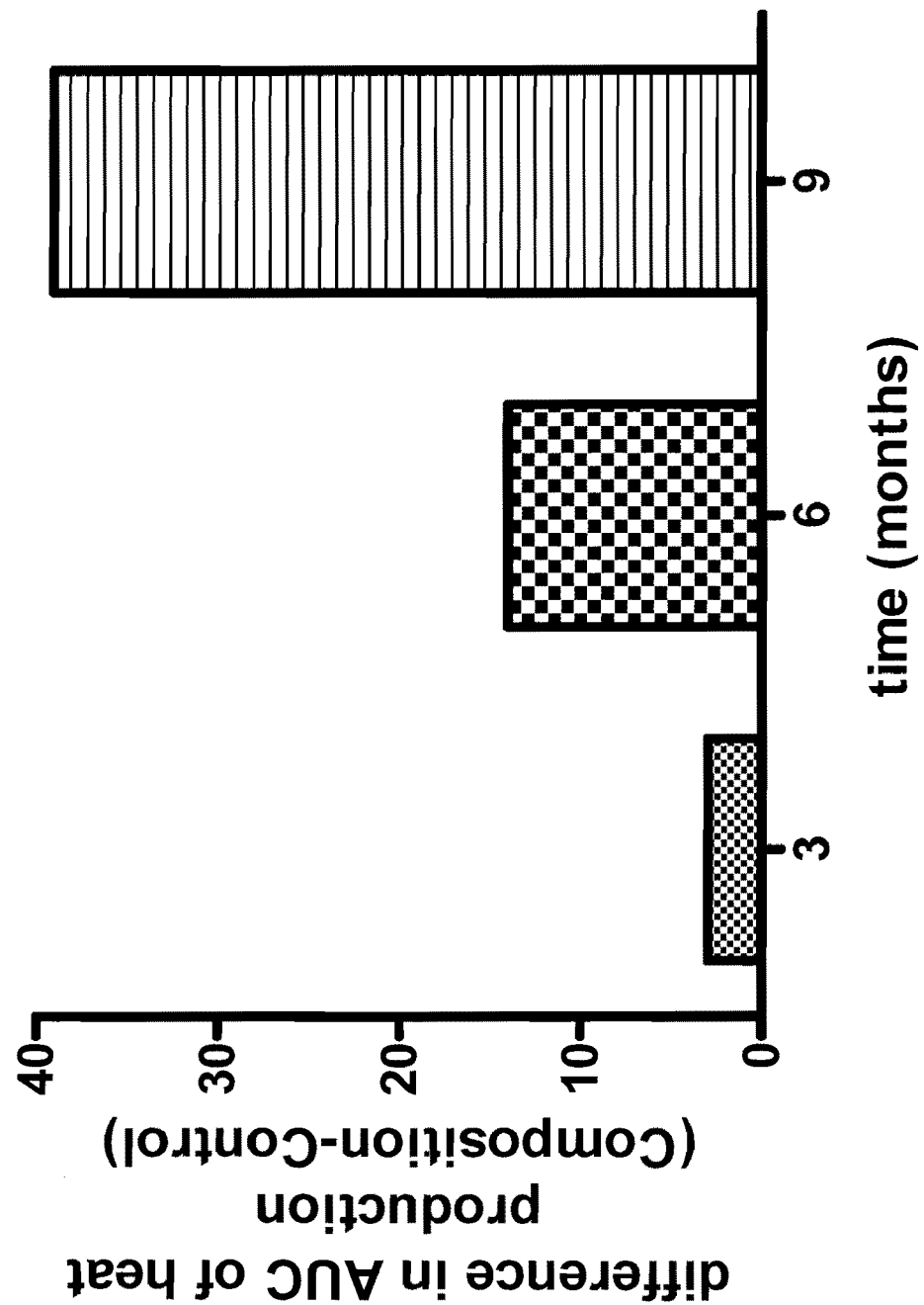
FIG. 8d: Difference of area under the curve (AUC) of heat production in APOE ko male mice (treatment begun at 10 weeks of age)
Figure 8E:
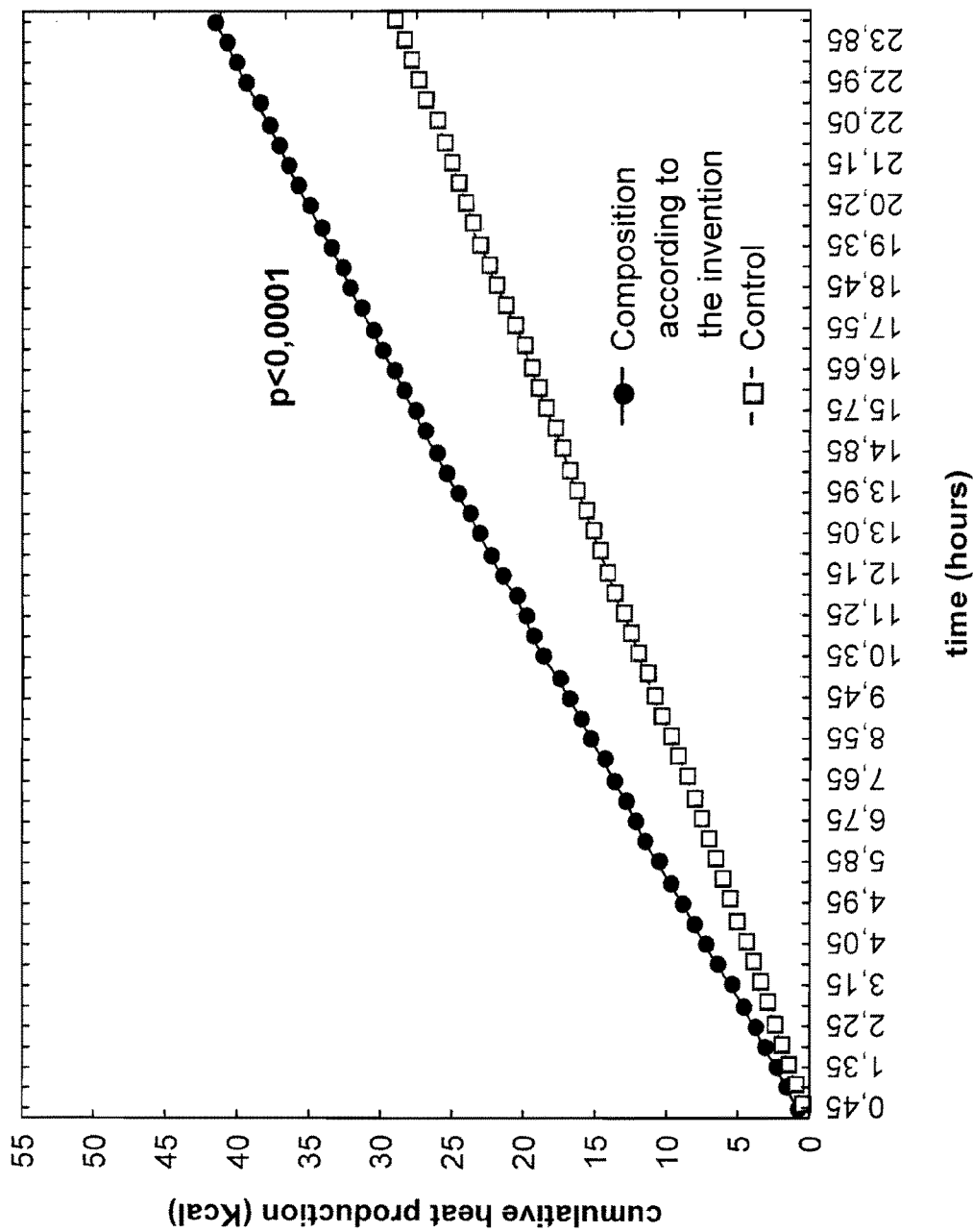
FIG. 8e: Cumulative heat production in LDLr ko male mice

Demonstration of the Role of the Composition in Accordance with the Invention in the Increase of Oxidative Metabolism FIG. 8 is multiple and illustrates the increase in heat production by APOE ko (FIGS. 8a, b, c, and d) and LDLr ko (FIG. 8e) mice induced by the composition in accordance with the invention versus the control group.

The increase in oxidative metabolism is reflected by the joint increase in oxygen uptake and heat production. Thus, by increasing these two parameters, the composition in accordance with the invention obviously increases oxidative metabolism in the body.

Indeed, the kilocalories values produced which were obtained at the same time and in the same animals as the measurements of the consumed oxygen volume, the interpretation of FIGS. 8 a, b, c, and d can be modeled on that of FIGS. 8 d, e, f, and g which show a progressive and constant upward shift of the heat production curve of the treated group compared to that of the control group, throughout the 9 months of treatment. Like FIG. 7g, FIG. 8d effectively shows that this shift systematically widens the gap between the surface under the heat production curve of the treated group and that of the control group which is thus multiplied by more than 4, between the 3rd and 6th month, then by 13 by the 9th month.

In the same way, FIG. 8e shows that for LDLr ko mice, the composition in accordance with the invention also increases their heat production. Indeed, this figure represents the cumulative heat production curves during 24 hours of mice of the treated and control groups. The curve of the treated group indicates that the heat production of this group is higher than that of the control group control. Since this difference is statistically significant, we can thus affirm that the composition in accordance with the invention increases the oxidative metabolism by jointly increasing heat production and oxygen consumption of the body (Example 7).

Example 12

Figure 9A:
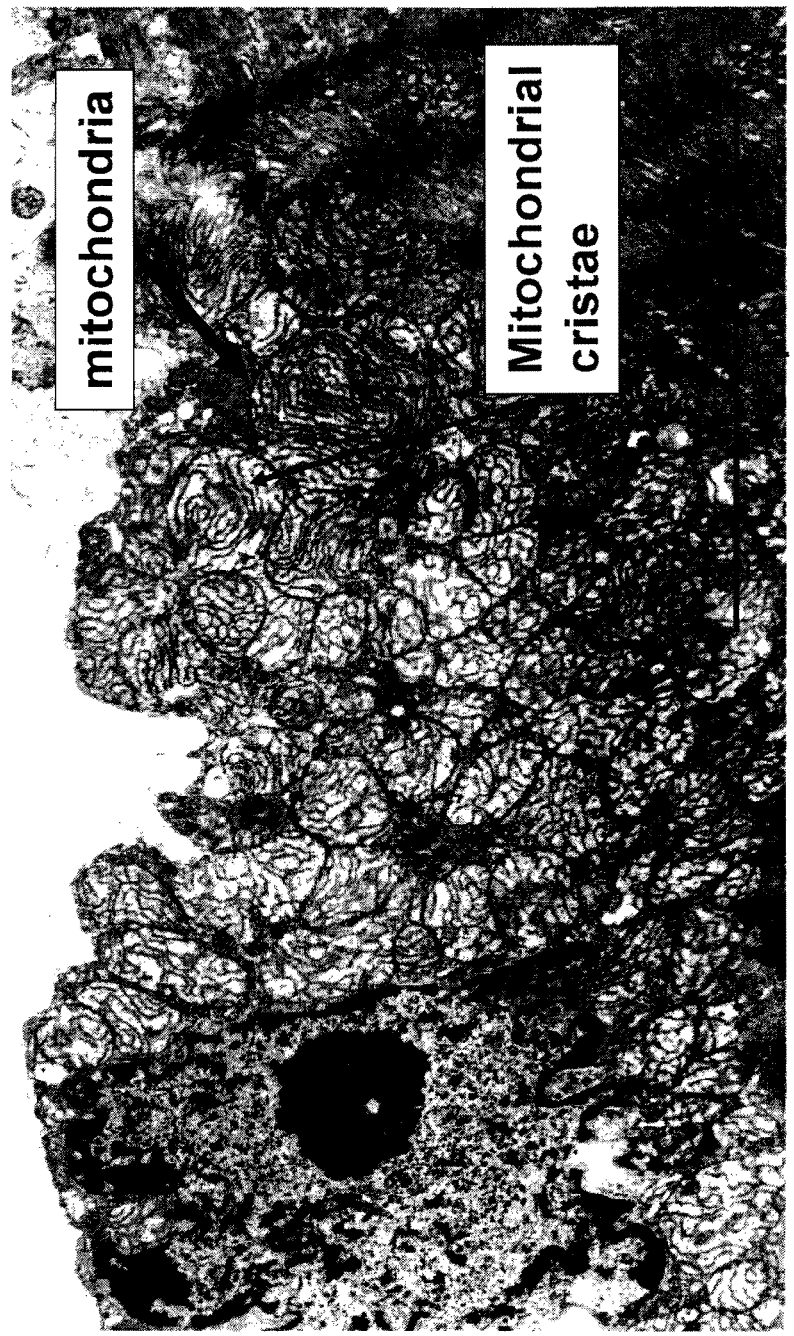
FIG. 9: Density of mitochondrial crests in oxidative muscles in OB/OB mice after 4 weeks of treatment with the composition in accordance with the invention versus the control.
Figure 9B:
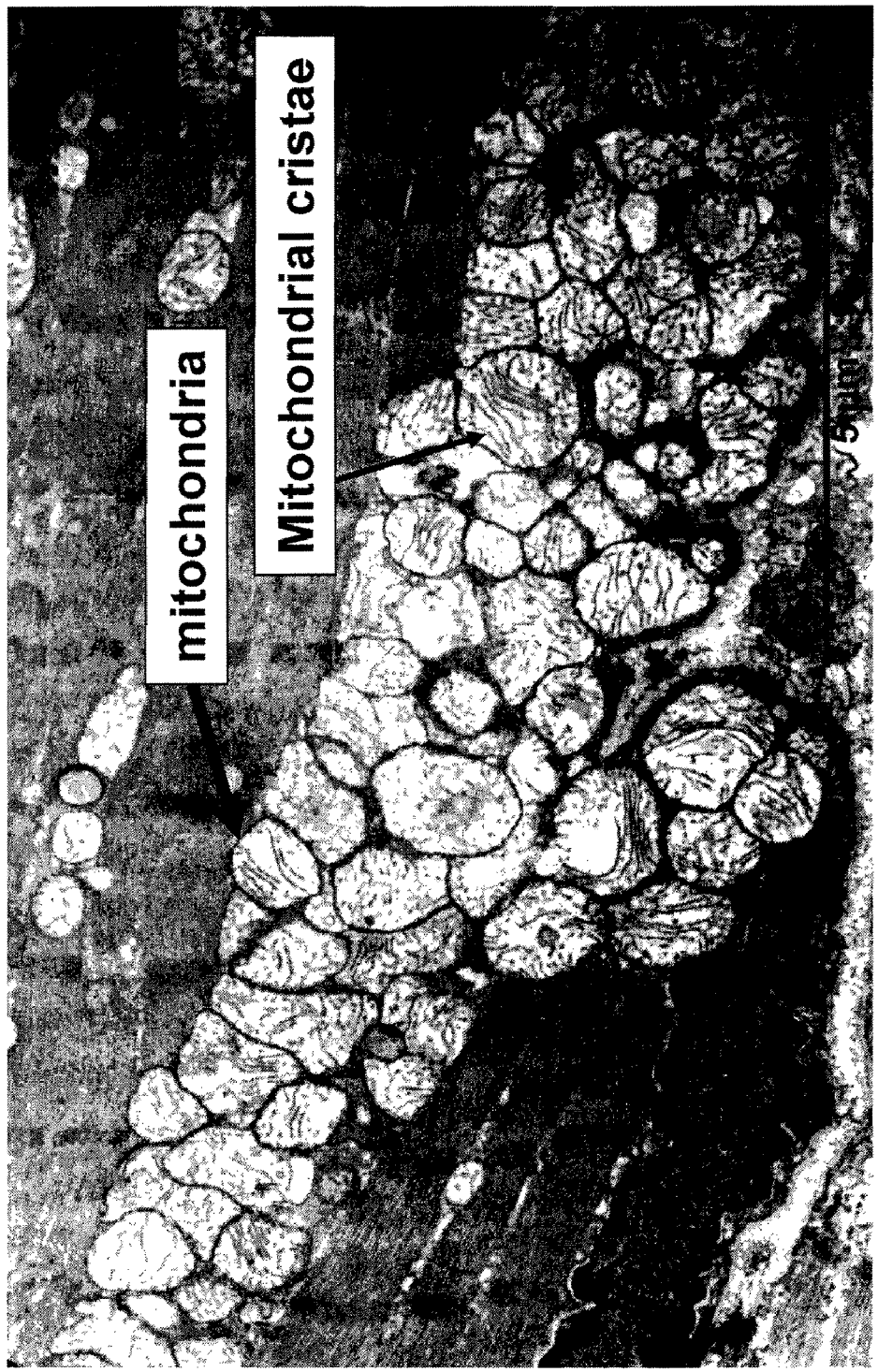

Demonstration of the Role of the Composition in Accordance with the Invention in the Increase in Biogenesis of Mitochondrial Peaks which are the Seat of Oxidative Metabolism FIG. 9 shows a increase in density of the mitochondrial peaks in OB/OB mice induced after 1 month of treatment by the composition in accordance with the invention versus the control.

Beginning at 2 months of age, two groups of OB/OB male mice received either the composition in accordance with the invention added to food for the first group, or the placebo also added to food for the second group. The two experimental groups always received the same quantity of food and were dissected after 1 month of treatment in order to take the soleus, which is an oxidative muscle, at the level of the mice's back legs, and to analyze its ultra structure under the electron microscope.

Mitochondria are the energy production units which equip the majority of cells in the body, and the oxidation of lipids takes place at the level of the mitochondrial peaks. The density increase of these peaks in the treated (FIG. 9a) versus control (FIG. 9b) group enables us to affirm that the composition in accordance with the invention increases the oxidation of lipids and thus their consumption by the body.

Example 13

Figure 10:
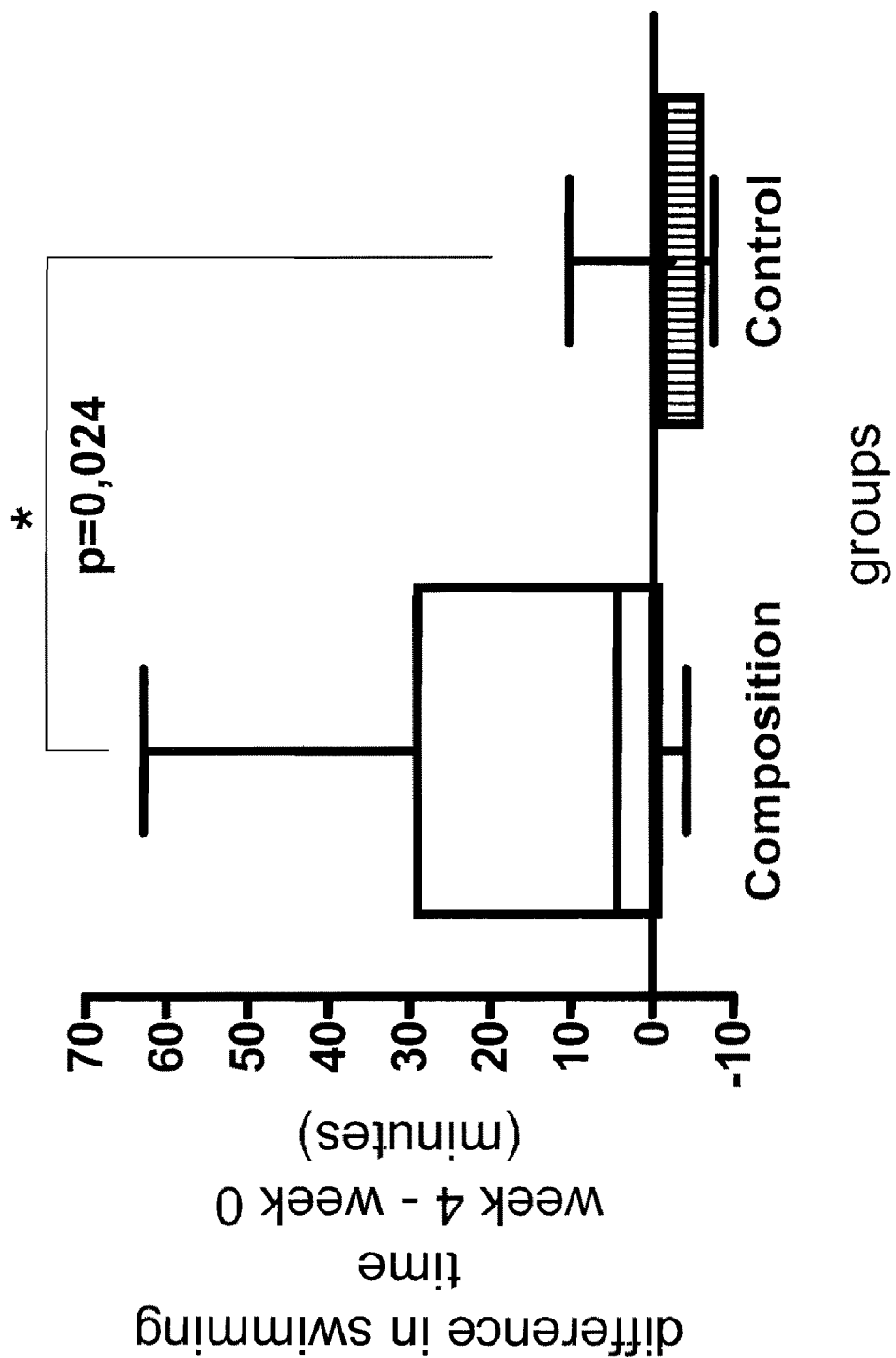
FIG. 10: Forced swimming test in OB/OB mice (with a load weighing 7.5% of their body weight)

Demonstration of the Role of the Composition in Accordance with the Invention in the Increase in Physical Performance and Endurance FIG. 10 shows an increase in the swimming time of OB/OB mice after 1 month of treatment with the composition in accordance with the invention versus the control.

Beginning at 2 months of age, two groups of OB/OB male mice received either the composition in accordance with the invention added to food for the first group, or the placebo also added to food for the second group. The two experimental groups always received the same quantity of food. The mice were forced to swim due to a weight (7.5% of their body weight) attached to their back legs, and the swimming time was recorded under these conditions for each mouse before and after 1 month of treatment. The increase in swimming time is acknowledged as an index of the increase in endurance. Thus, as shown in FIG. 10, we have recorded an increase in the swimming time and thus of endurance in the group of treated mice treated contrary to the control group whose swimming time even decreased according to the natural development of physical performance which decrease with age. Since this increase is significant it enables us to affirm that the composition in accordance with the invention increases endurance and physical performance. The nutritional interest in this composition for the optimization of athletic performance as well as for improvement and maintenance of physical fitness is thus very meaningful.

Example 14

Demonstration of the Role of the Composition in Accordance with the Invention in the Stabilization of Triglyceride Plasma Levels FIG. 11 illustrates stabilization of triglyceride plasma levels in LDLr ko and APOE ko mice induced by the composition in accordance with the invention versus the control.

Stabilization over the long term of triglyceride plasma levels is a major asset in the fight against metabolic syndrome and cardiovascular diseases.

Figure 11A:
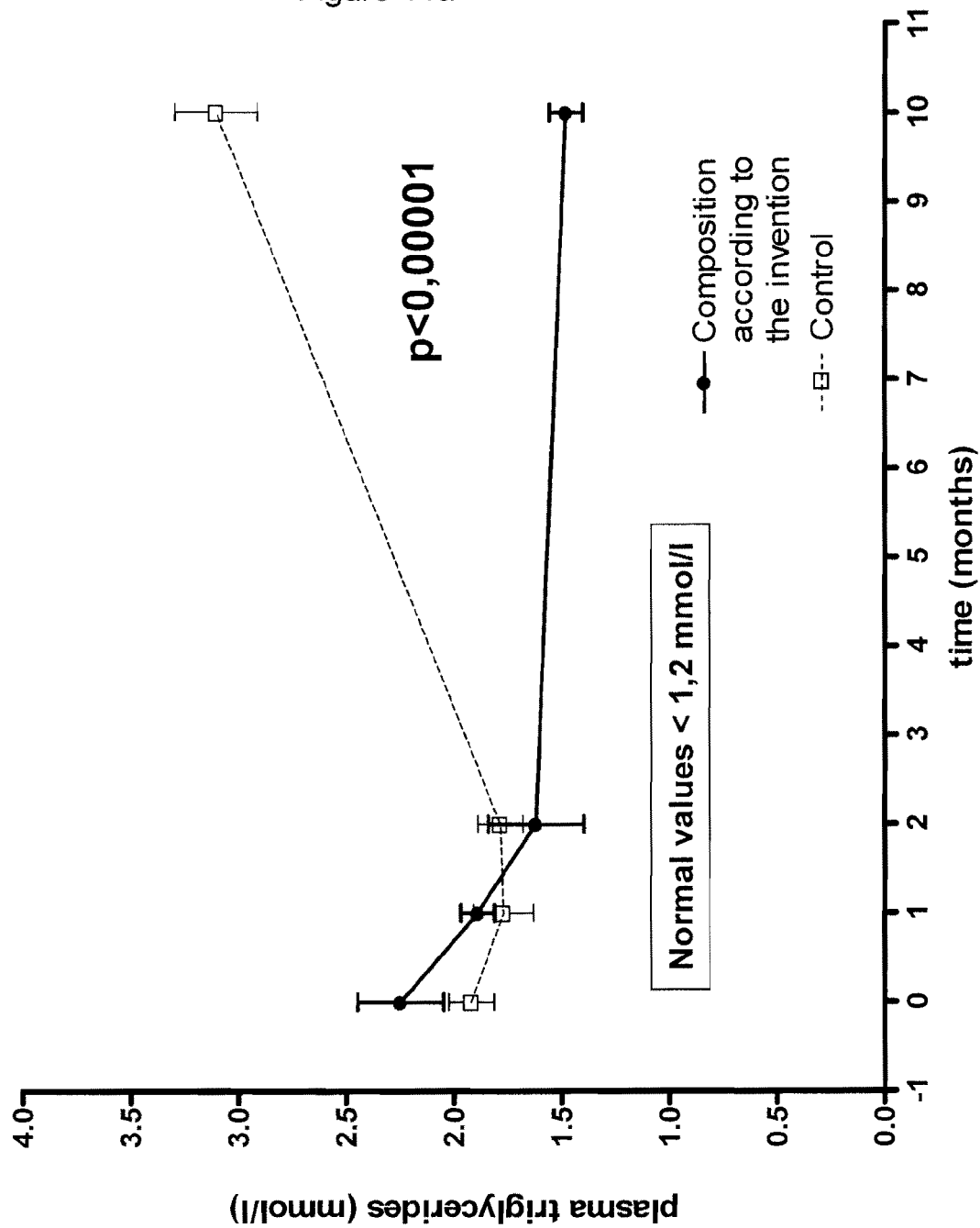
FIG. 11a: Development of plasma triglyceride levels in LDLr ko male mice
Figure 11B:
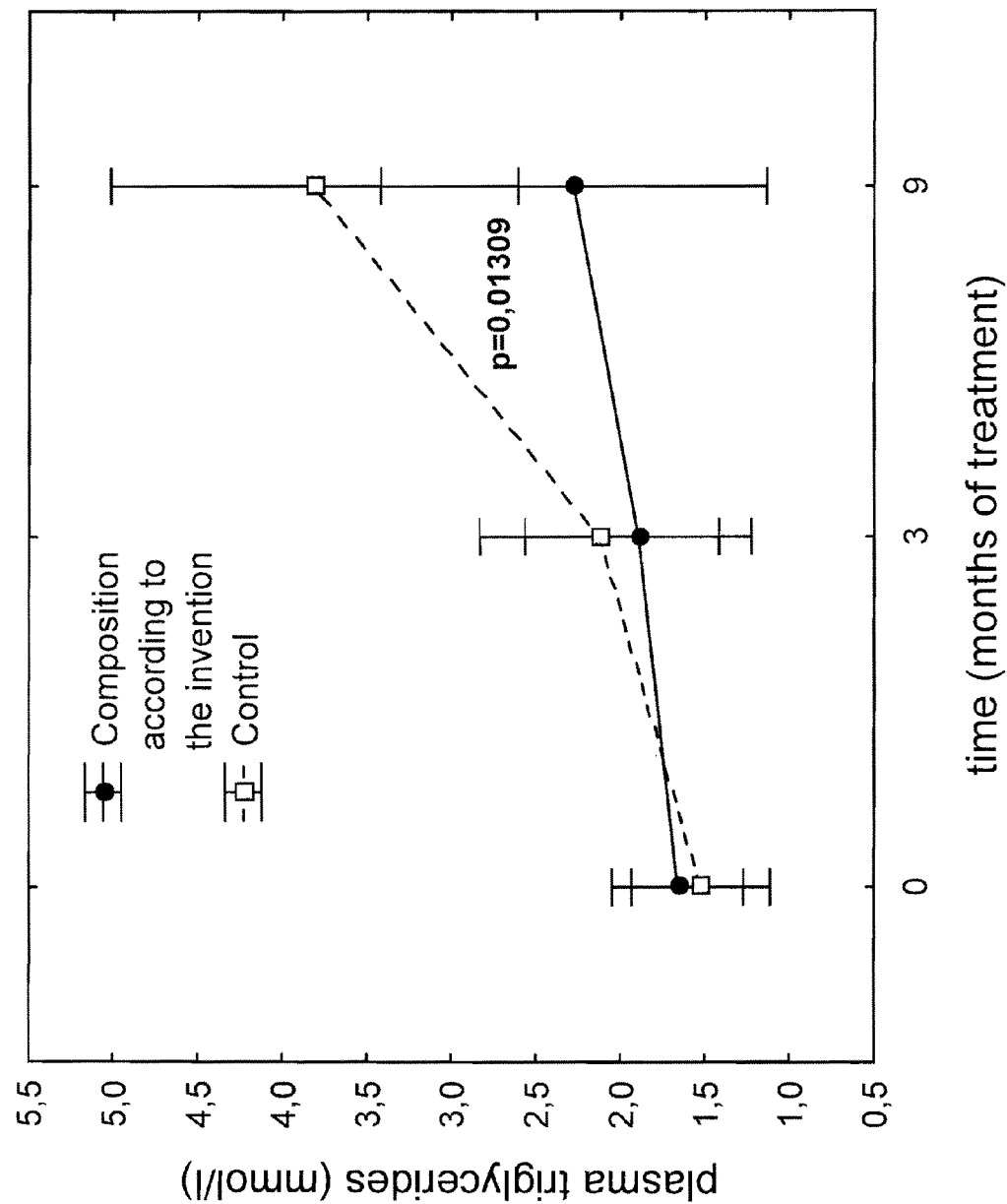
FIG. 11b: Development of triglyceride plasma levels in APOE ko male mice (treatment begun at 10 weeks of age)

Thus, the purpose of the experiments the results of which are shown in FIGS. 11a and 11b was to verify whether the lipid-lowering effect of the composition in accordance with the invention is maintained in the long-term.

Beginning at 2 months of age, two groups of LDLrko male mice received either the composition in accordance with the invention added to food for the first group, or the placebo also added to food for the second group. Idem for the experiment with APOE ko male mice. The two experimental groups for each mouse strain always received the same quantity of food and their blood was taken by retro-orbital puncture before beginning the treatment, then after 1 month, then 2 months, and then 10 months of treatment in the LDLr ko mice (FIG. 11a), and after 3 and 9 months of treatment for APOE ko mice (FIG. 11b). The two FIGS. 11a and 11b show the same effectiveness of the composition in accordance with the invention in maintaining stable triglyceride plasma levels, in the long run, in LDLr ko as well as in the APOE ko mice, whereas these rates irremediably increase in control mice. Since this difference is statistically significant it enables us to affirm the lipid-lowering effectiveness in the long run of the composition in accordance with the invention, and thus its role in the prevention of metabolic syndrome and cardiovascular diseases.

Example 15

Demonstration of the Role of the Composition in Accordance with the Invention in the Maintenance of a Stable Post-Prandial (after Meals) Triglyceride Plasma Level FIG. 12 illustrates the absence of a post-prandial increase in triglyceride plasma levels in LDLr ko mice due to the composition in accordance with the invention versus the control.

One of the lipid-lowering mechanisms is the reduction in intestinal absorption of food triglycerides. Moreover, the post-prandial plasma overload in food triglycerides is a major and well-recognized vascular risk factor.

Thus, by preventing the increase in the post-prandial triglyceride plasma levels, the composition in accordance with the invention not only prevents flooding the body with a lipid overload, but also protects vascular walls, and thus prevents the formation of atheromatous plaques (see Example 7).

Figure 12A:
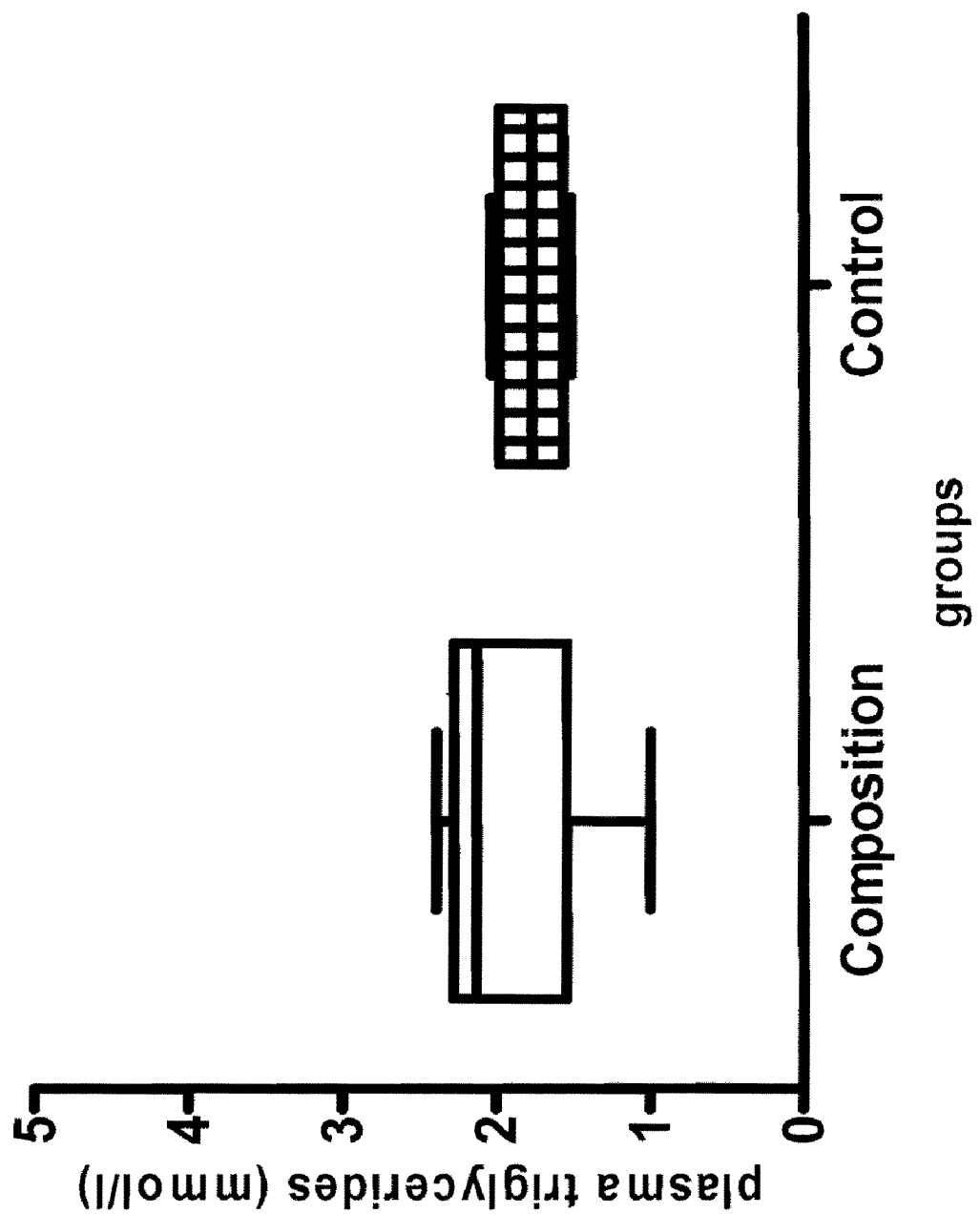
FIG. 12a: Triglyceride plasma levels in LDLr ko male mice on an empty stomach (10 months of treatment)
Figure 12B:
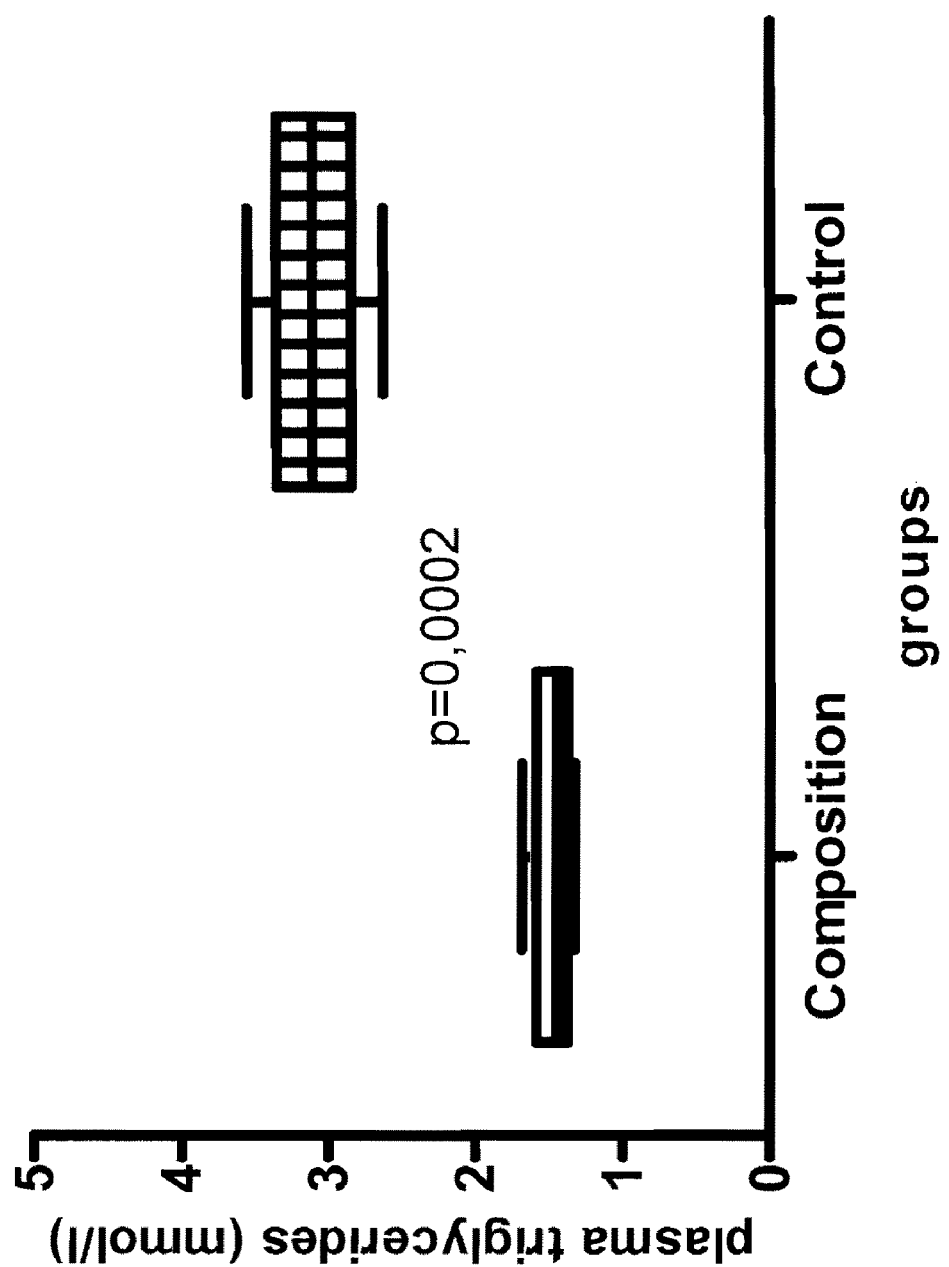
FIG. 12b: Postprandial triglyceride plasma levels in LDLr ko male mice (10 months of treatment)

Thus, the purpose of the experiment the results of which is shown in FIGS. 12a and 12b is to verify whether the lipid-lowering effect of the composition in accordance with the invention goes through a limitation in the intestinal absorption of food lipids.

Beginning at 2 months of age, two groups of LDLrko male mice received either the composition in accordance with the invention added to food for the first group, or the placebo also added to food for the second group. The two experimental groups for each mouse strain always received the same quantity of food and their blood was taken by retro-orbital puncture after 10 months of treatment, after 16 hours of fasting (FIG. 12a), then in a nourished state (FIG. 12b). FIG. 12a shows equivalent triglyceride plasma levels after fasting in the two experimental groups. On the other hand, FIG. 12b shows different triglyceride plasma levels in a nourished state for the two experimental groups, with a significant increase in the control group, which was avoided in the treated group with the composition in accordance with the invention. Since this difference is statistically very significant it enables us to affirm the effectiveness of the composition in accordance with the invention in maintaining a stable post prandial triglyceridemia, and thus its role in the prevention of metabolic syndrome and cardiovascular diseases.

Example 16

Figure 13A:
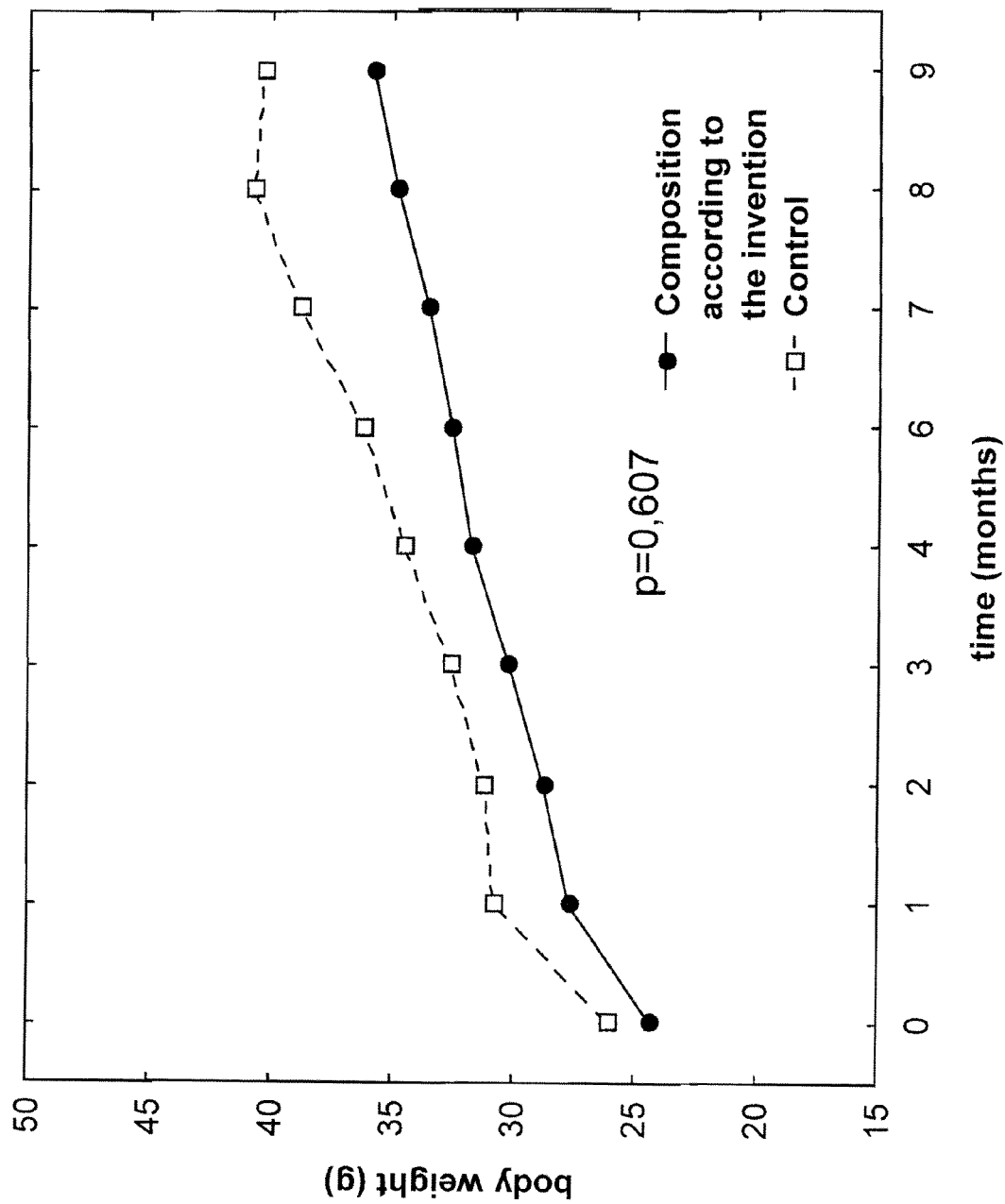
FIG. 13a: Development of body weight in PPARa(ko)LDLr(ko) male mice
Figure 13B:
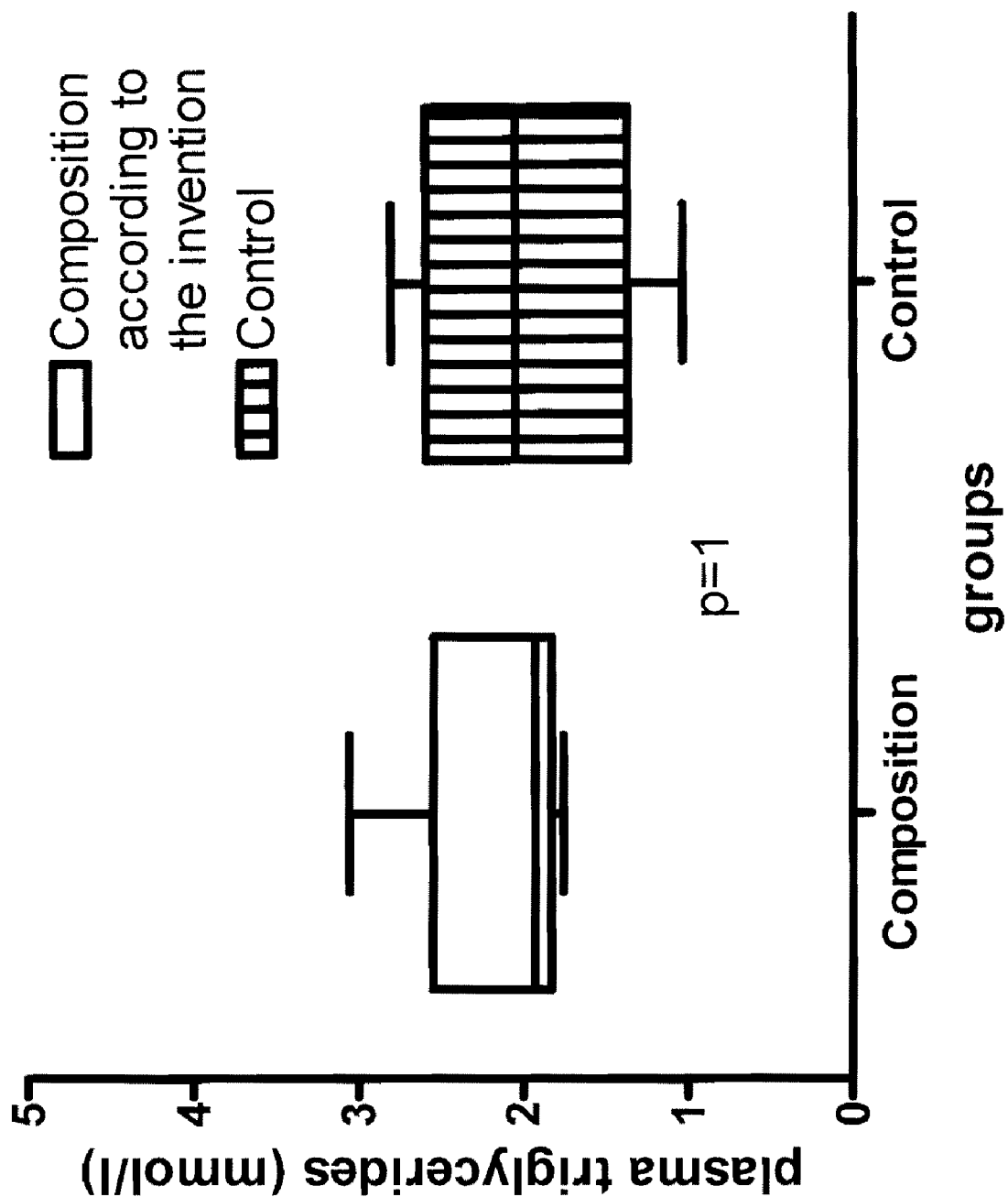
FIG. 13b: Triglyceride plasma levels in LDLrkoPPARako male mice NOT on an empty stomach after 10 months of treatment
Figure 13C:
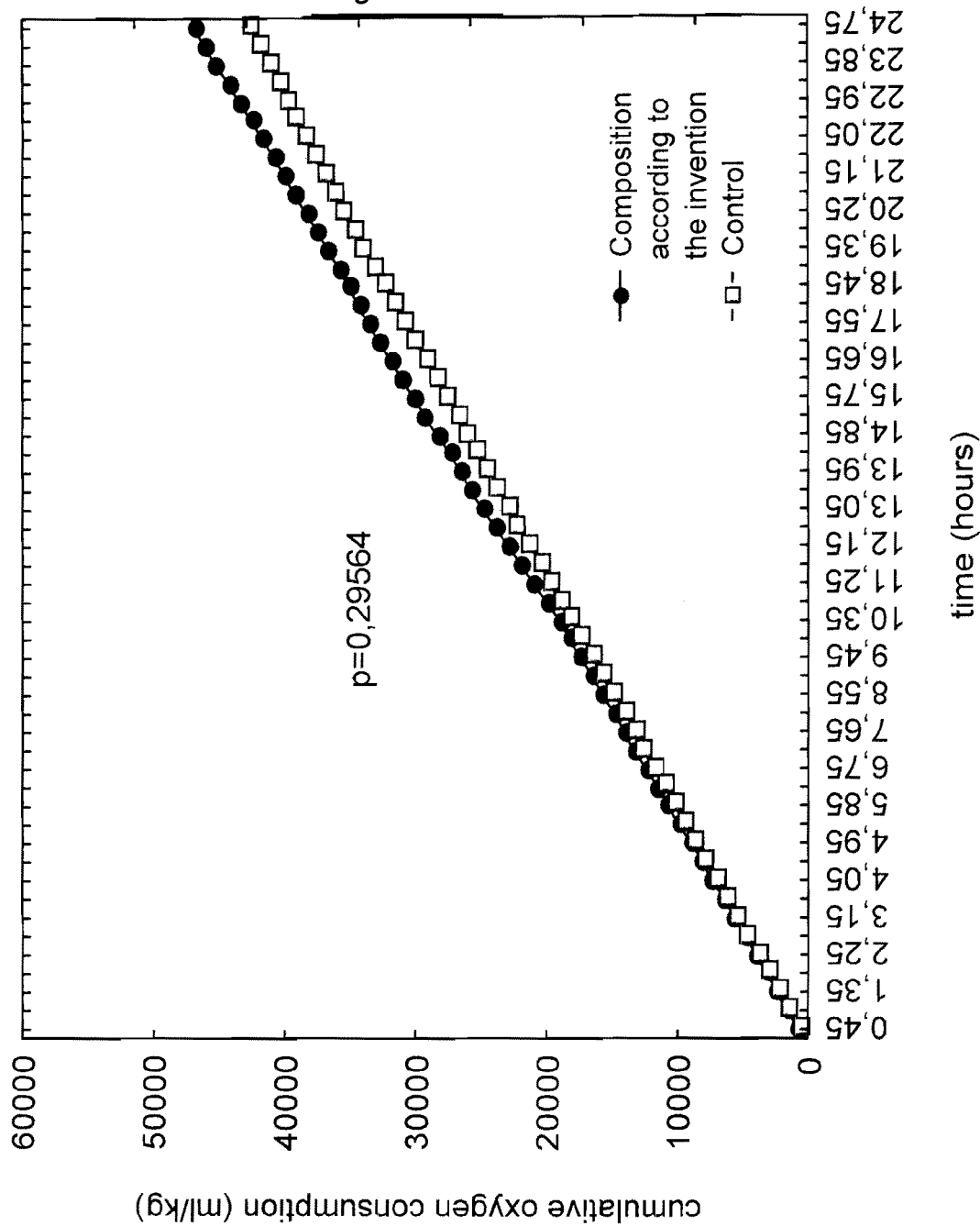
FIG. 13c: 24 hr cumulative oxygen uptake in LDLr(ko) PPARalpha(ko) male mice
Figure 13D:
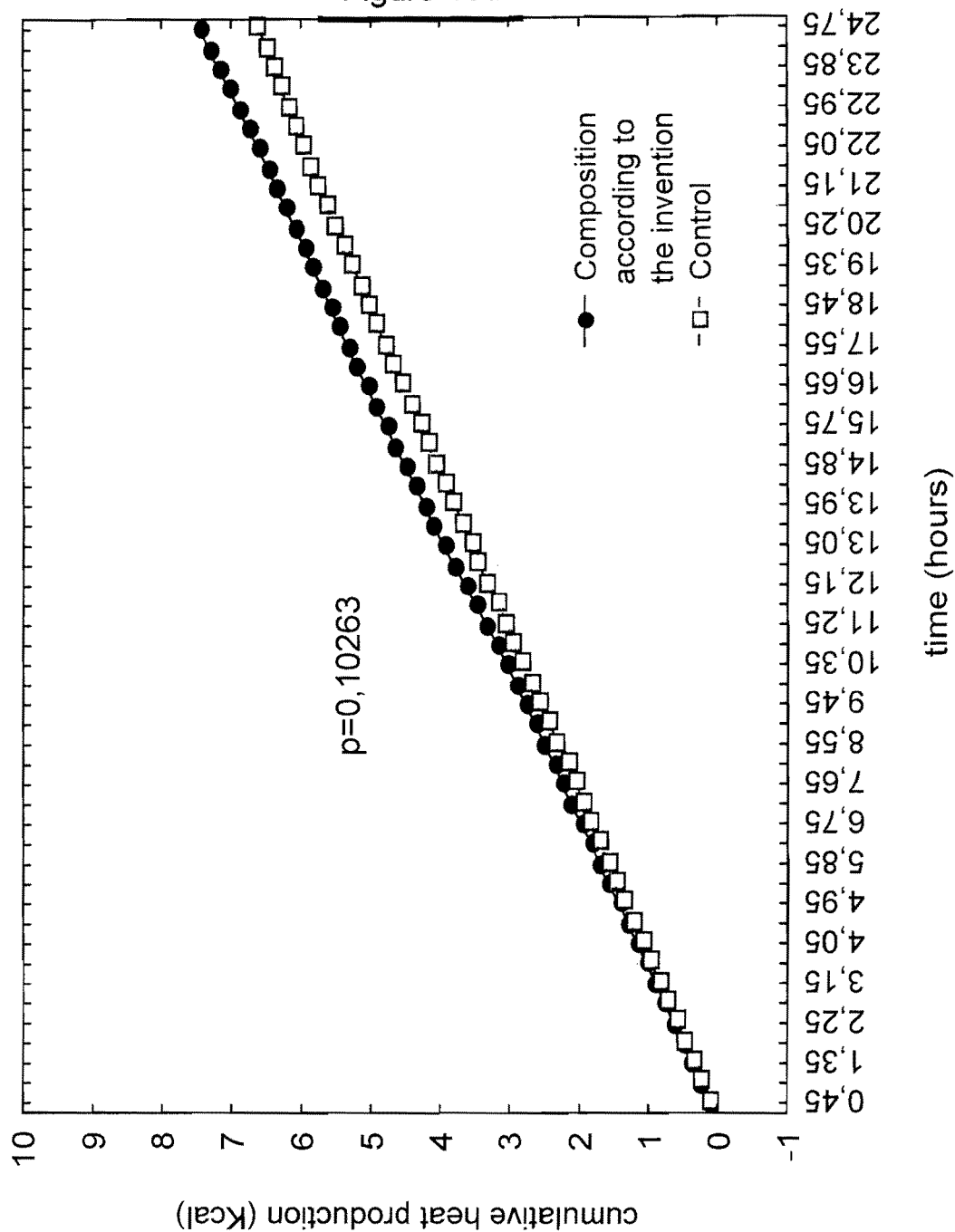
FIG. 13d: 24 hr cumulative heat production in LDLr(ko) PPARalpha(ko) male mice

Demonstration of the Role of the Composition in Accordance with the Invention in the Increase in Lipid Use by Muscles Via Activation of the PPAR-Alpha Receptor, which is the Principal Actor in Oxidative Lipid Catabolism FIG. 13 illustrates the disappearance of the effects of the composition in accordance with the invention in LDLr ko mice, who lack PPAR-alpha, on body weight (FIG. 13a), as well as on triglyceride plasma levels (FIG. 13b), oxygen uptake (FIG. 13c), and heat production (FIG. 13d).

The use of a knock-out (ko) mouse model, i.e., lacking a given gene, is the method of choice for the study of gene function, and its importance in a given control. In the exact case shown in FIG. 13, the use of the ko mouse model for PPAR-alpha permits confirmation of the importance of this receptor as a mediator in metabolic effects of the composition in accordance with the invention.

Indeed, the limitation in weight gain, the stabilization of triglyceride plasma levels as well as the increase in oxidative metabolism (increase in oxygen uptake coupled with an increase in heat production) observed in LDLrko male mice treated for 10 months with the composition in accordance with the invention disappear as soon as the PPAR-alpha gene is disabled in this same mouse strain, made doubly defective for both LDLr and PPAR-alpha.

Thus, the purpose of the experiment the results of which are shown in FIGS. 13a, b, c, and d is to verify if the metabolic effects of the composition in accordance with the invention are dependent on the activation of the PPAR-alpha receptor.

Beginning at the age of 2 months, two groups of LDLr ko-PPARalpha ko mice received either the composition in accordance with the invention added to food for the first group, or the placebo also added to food for the second group. The two experimental groups always received the same quantity of food. They were regularly weighed during the 10-month treatment, their blood was taken by retro-orbital puncture in a nourished state, and they remained in individual calorimetric cages at the end of the treatment. FIG. 13 shows no statistically significant difference between the two treated and control groups of the experiment for mice lacking PPAR-alpha, as well as with regards to body weight development (FIG. 13a), to stabilize the triglyceride plasma levels (FIG. 13b), oxygen uptake (FIG. 13c), and heat production (FIG. 13d). The metabolic effects previously observed in the LDLrko male mice, and which disappeared in the LDLr ko-PPAR-alpha ko male mice, enable us to confirm the paramount importance of PPAR-alpha in the effectiveness of the composition in accordance with the invention, which thus proves to be a natural ligand for this receptor. PPAR-alpha being a principal actor of the oxidative catabolism of lipids, the effects of the composition in accordance with the invention on body weight, triglyceride levels and oxidative metabolism can thus be explained via a direct activation of PPAR-alpha by the composition in accordance with the invention as shown in Experiment 14 (described below).

Figure 14:
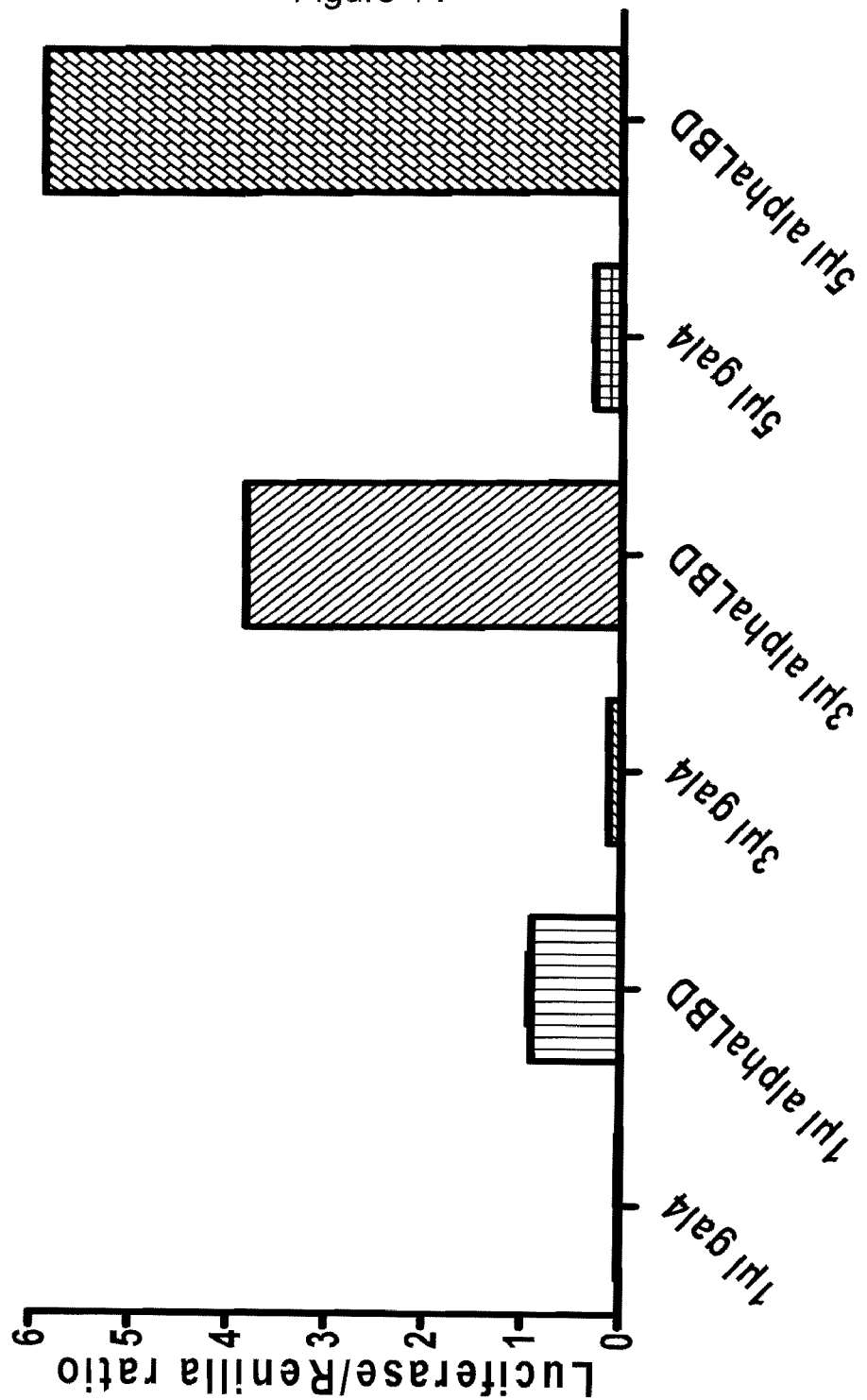
FIG. 14: PPAR-alpha transactivation test by the composition in accordance with the invention in NIH3T3 cells transfected by 5UAS-LUC+Renilla+Gal4 or Gal4-alpha-LBD

FIG. 14 illustrates in cellulo activation of PPAR-alpha by the composition in accordance with the invention with a dose effect which confirms this activation.

A transactivation test is a test which allows certain confirmation of a given substance directly activating a transcription factor. PPAR-alpha is a nuclear receptor which, once activated, controls the transcription of a certain number of genes.

In order to carry out this transactivation test, NIH3T3 cells (usually used for this kind of test) were transfected by a plasmid containing a Luciferase gene under the control of a promoter (5×UAS) which can only be activated by one exogenic transcription factor (GAL4) which is transfected in these same cells, either alone, or together with the binding domain (GAL4-alphaLBD) of PPAR-alpha ligands. In these same cells, one also introduces Renilla as transfection control, and whose expression level allows standardizing that of Luciferase.

Thus, for all cell cultures transfected with Luciferase, Renilla and GAL4, there was almost no activation of transcription of Luciferase after addition of the composition in accordance with the invention in the culture medium, whereas those transfected with Luciferase, Renilla, and GAL4-alphaLBD recorded an expression of Luciferase which increased proportionally with the increase in the amount of the composition in accordance with the invention in the culture medium. Thus, the composition in accordance with the invention directly activates PPAR-alpha while binding to ligand-binding domain, and thus induces the expression of target genes of this nuclear receptor and transcription factor, as shown in FIG. 15 (described below).

FIG. 15 illustrates activation of PPAR-alpha by the composition in accordance with the invention which results in overexpression of all the target genes for which transcription is dependent on this activation.

The overexpression of the target PPAR-alpha genes proves its activation in OB/OB male mice treated by the composition in accordance with the invention during 4 weeks versus the control.

Beginning at 2 months of age, two groups of OB/OB male mice received either the composition in accordance with the invention added to food for the first group, or the placebo also added to food for the second group. The two experimental groups always received the same quantity of food. After one month of treatment, the mice were dissected and some samples of skeletal muscle were taken in order to analyze their genetic expression profiles induced by the composition in accordance with the invention in this tissue.

Among the genes induced by the composition in accordance with the invention in muscles, all those for which the expression is dependent on activation of PPAR alpha are overexpressed (Rakhshandehroo M, Sanderson L M, Matilainen M, Stienstra R, Carlberg C, de Groot P J, Müller M, Kersten S. Comprehensive Analysis of PPARalpha-Dependent Regulation of Hepatic Lipid Metabolism by Expression Profiling. PPAR Res. 2007; 2007:26839.). These genes all are involved in collecting fatty-acids in the muscle and their oxidation, at the mitochondrial as well as the peroxisomal level.

Thus, the composition in accordance with the invention induces catabolism of lipids and their use as an energy substrate in muscle. This increase in the use of lipids by the muscle is in line with the increase in muscular endurance described in Example 8.

Indeed, during endurance exercises, the muscle preferably uses lipids as an energy substrate, and reciprocally, increases the use of lipids by the muscle thus making it stronger. Other possible explanations to this increase in muscular endurance are an increase in muscular trophicity and contractility.

Figure 16:
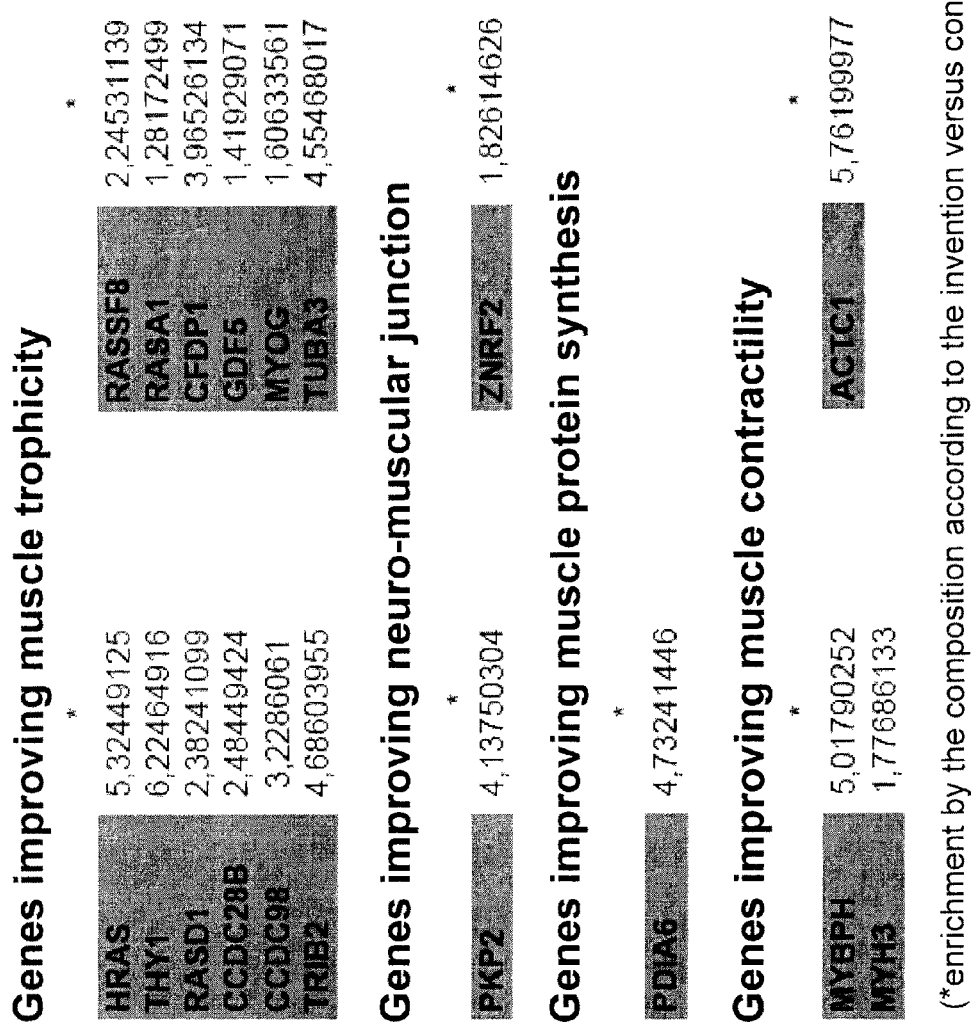
FIG. 16: Overexpressed muscle genes in OB/OB mice after one month of treatment, involved in neuro-muscular transmission, trophicity, protein synthesis, and muscle contractility

FIG. 16 illustrates the increase in the expression of genes controlling trophicity, neuro-muscular junction, and muscular contractility by the composition in accordance with the invention versus the control.

For the experiment the results of which are shown in FIG. 16, beginning at 2 months of age, two groups of OB/OB male mice received either the composition in accordance with the invention added to food for the first group, or the placebo also added to food for the second group. The two experimental groups always received the same quantity of food. After one month of treatment, the mice were dissected and some samples of skeletal muscle were taken in order to analyze their genetic expression profiles induced by the composition in accordance with the invention in this tissue.

The increase in endurance by the composition in accordance with the invention (see example 13) may be explained by better quality muscle fibers due to the enrichment of the gene expression of CCDC28B and CCDC98 which support the formation of a solid fascicle of muscle fibers, which will thus take longer to develop microlesions induced by an strengthening exercises. One of the most essential genes for muscular trophicity is HRAS whose absence is at the origin of the dysmorphic syndrome of Costello, characterized by fine tendons and a muscle cancer risk of 15%. In animals treated with the composition in accordance with the invention, the gene expression of HRAS is enriched more than 5 times versus the control.

The gene PDIA6, whose expression is almost 5 times more enriched in animals which received the composition in accordance with the invention versus the control, contributes to the synthesis of new muscular proteins which will allow an effective and fast repair of the microlesions mentioned above. An increase in endurance also implies good contractile capacity. Thus, the expression of key contractile proteins like ACTC1 and MYBPH is more than 5 times enriched in animals treated by the composition in accordance with the invention versus control. Good contractile capacity depends on good performance of the neuro-muscular junction. It is logical that the expression of genes such as PKP2 and ZNRF2, involved in transmission of the nerve impulse to the muscle, is enriched in treated animals. The composition in accordance with the invention thus positions itself like an auxiliary treatment of muscular dystrophies, and particularly in those due to a decrease in neuromuscular transmission, or quite simply of prolonged immobilization (as in a fracture), by facilitating fast recovery of good muscle performance while performing rehabilitation exercises.

Example 17

Genomic Effects of the Composition in Accordance with the Invention

A. Muscle is the Main Target of the Genomic Action of the Composition in Accordance with the Invention
Course of the Experiment:
Obese Ob/ob mice were fed during 4 weeks with a standard diet containing or not the composition in accordance with the invention. Ribonucleic Acid (RNA) containing the information related to gene expression was extracted from the liver, the gastrocnemius-soleus muscle, and epididymal white adipose tissue. These RNAs were purified, labeled and hybridized on Affymetrix Mouse Genome 430.2.0 chips. The statistical analysis of data was carried out by using the R statistical computer programming language (R Core, 2004, http://www.R-project.org). The data was standardized for each tissue separately by using RMA (Irizarry, R. A., et al., 2003), and genes regulated by the composition in accordance with the invention were identified by linear modeling with the limma program (Smyth, G. K. 2004). 2004).

Figure 17:
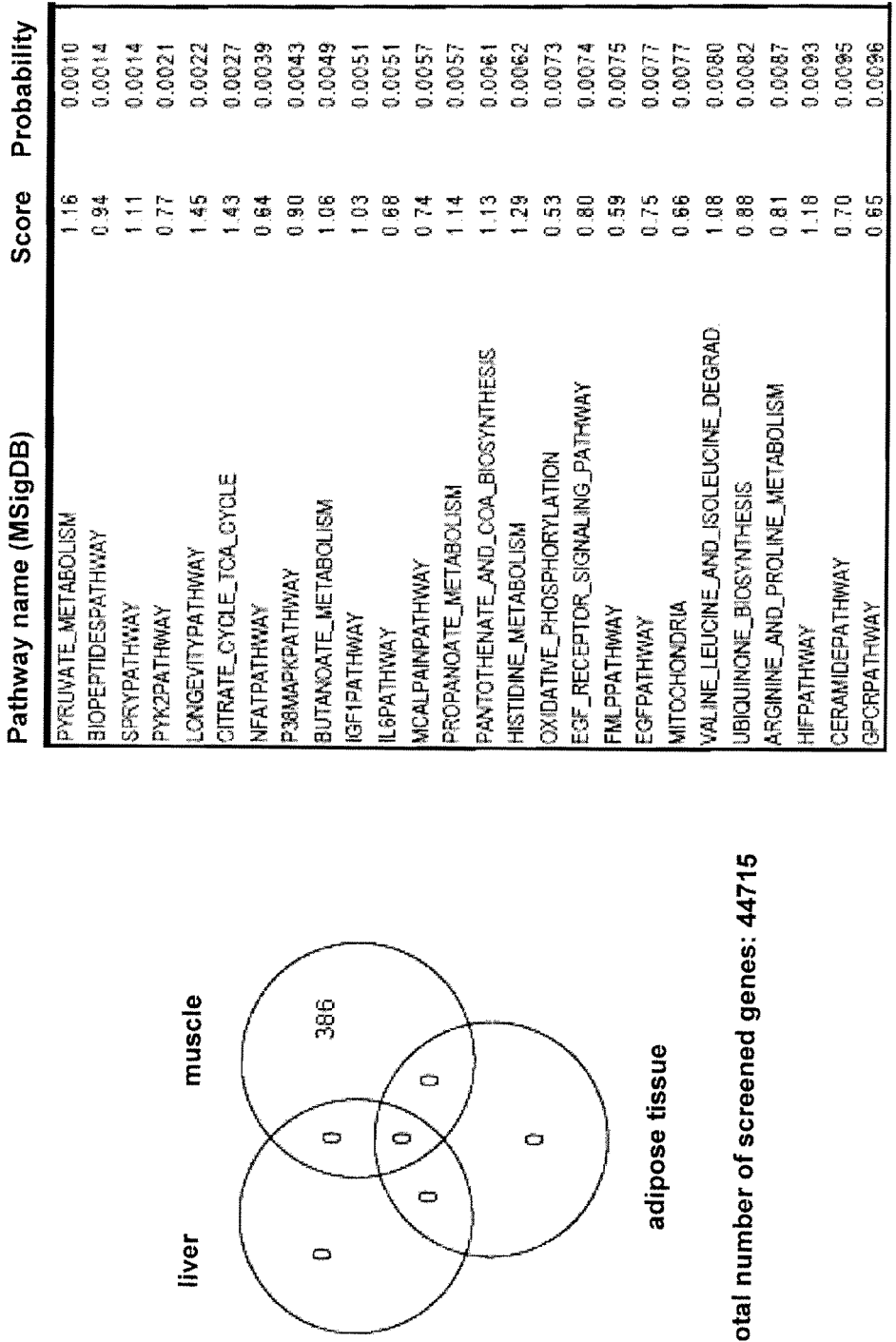
FIG. 17A: Venn's diagram showing the number of genes affected by treatment with the composition in accordance with the invention in the liver, skeletal muscle, and adipose tissue. Comparisons were made between control animals and those treated with the composition in accordance with the invention (n=7 by group). Genes expressed in a differential way have a probability lower than 10% of being false-positive.
FIG. 17B: Analysis by gene group of the effect on skeletal muscle by the composition in accordance with the invention. Gene groups showing the signal transduction and metabolic pathways were compiled by experts and are available in the database "Molecular Signatures Database" (MSigDB). The pathways enriched to a significant degree by the composition in accordance with the invention are indicated in the table (P<0.01, false-positive rate<12%). The name of the gene group as it is named in MsigDB, the enrichment score (positive=enrichment, negative=impoverishment), and the probability values are indicated.

Results:

FIG. 17A shows that the composition in accordance with the invention acts mainly on muscle. The regulated genes were selected in order to get a false-positive rate lower than 10%. 386 genes are differentially expressed in the muscle, but none in the liver or fat tissue. However, this experiment does not allow the exclusion of other target organs not yet tested. Finally, this study cannot rule out that the composition in accordance with the invention induces a structural modification of RNA, or a modification of the protein synthesis or structure in liver or fat tissue, as well as having an effect on the expression of a small number of genes which could have been lacking because of the lack of power in the statistical test.

B. The Composition in Accordance with the Invention Acts on Genes Involved in Muscle Metabolic Activity Course of the Experiment:

A test was performed to determine whether genes belonging to a particular metabolic or signal transduction pathway were systematically over- or under-expressed after treatment with the composition in accordance with the invention. For this, an analysis known as the gene set enrichment analysis ("gene set enrichment analysis"), similar to that proposed by Mootha et al. (2003), was performed. However, a modification was provided in order to be able to calculate enrichment scores beginning with the statistics calculated by the program limma. The significance of the scores was estimated by random permutations of the samples to estimate the null distribution of values. The groups of genes representing the canonical cellular pathways come from the database "Molecular Signatures Database" (MSigDB, www.broad.mit.edu/gsea/msigdb/).

Results:

The enrichment analysis of gene sets indicates that the composition in accordance with the invention causes a significant alteration of 26 canonical pathways. Among these, several metabolic pathways are affected: pyruvate metabolism, Krebs cycle, oxidative phosphorylation, pathways of metabolism of butanoate, propanoate, and pantothenate fatty acids, as well as biosynthesis of acetyl-CoA (FIG. 17B). This shows a general increase of the metabolic capacity of muscular cells under treatment with the composition in accordance with the invention. An increase in the metabolic activity of the mitochondria will produce oxidative stress ("reactive oxygen species", ROS) which will damage the cell. However, in mice treated with the composition in accordance with the invention, one observes an increase in RNA coding for superoxide dismutases 2 and 3, which are the principal regulators of ROS, and which act as a catalyst in their degradation. These enzymes belong to the "longevity pathway". Several intracellular signal transduction pathways are also positively affected by the composition in accordance with the invention (pathways Biopeptides, Spry, Pyk2, Igf-1, Il-6, Egf, fMLP, p38, and GPCR). This is the opposite of what occurs in insulin resistance syndrome, where a defect in these signal transduction pathways is observed.

REFERENCES

Irizarry, R. A., et al. (2003). *Exploration, Normalization, and Summaries of High Density Oligonucleotide Array Probe Level Data. Biostatistics* 4:249-64.

Mootha V K, et al. (2003). PGC-1 alpha-responsive genes involved in oxidative phosphorylation are coordinately downregulated in human diabetes. Nat Genet. 34:267-73.

Smyth, G. K. 2004. Linear models and empirical Bayes methods for assessing differential expression in microarray experiments. *Stat. Appl. Genet. Mol. Biol.* 3: 3.

C) Preliminary Clinical Studies in Humans

These studies were performed in a population of adults who fulfilled the following criteria:

For both men and women, age must range between 18 and 80 years old

After having failed the hygiene-dietetic diet over a 3-month period

People presenting a total cholesterol≧ to 2.30 g/l (6.05 mmol/l), LDL-C≧1.50 g/l (3.9 mmol/l) and/or triglycerides≧1.50 g/l (1.69 mmol/l)

Physical exercise and taking of food supplements must be stable and unchanged for the period of the study Eating food that lowers cholesterol; oat bran, soy proteins higher than 10 g/d must be the same for at least 3 months before starting the study, and must not change during the period of the study.

The following people are excluded from these studies:

Those having a known and severe family hypercholesterolemia.

Those under treatment using a lipid lowering medicament: resins, fibrates, statins, nicotinic acid, a 3-month period is required after ending use of the product.

Taking stanols, selective intestinal cholesterol absorption inhibitor, omega-3s

Pregnant women

Suffering from a cancerous disease or not considered as suitable for sticking to the nutritional intervention Suffering from diabetes 1 (the period of the study is not long enough to obtain control)

Being younger than 18 years of age

Example 18

Lipid Metabolism by Using a Composition of the Invention in Accordance with Example 1

The nutritional intervention is a study carried out over a test period of 4 weeks in a population of 35 adults (13 men and 22 women) with an average age of: 61.1 years, presenting on D0 an average cholesterol level of 2.85 g/l (7.5 mmol/l) and LDL-C of 2.02 g/l (5.25 mmol/l). This population of adults is divided into 2 groups:

Isolated hypercholesterolemia (75 cases)

Mixed hyperlipidemia (29 cases)

During the study period, the patients may not change their former dietary habits.

From the first day of the study, the composition obtained according to Example 1 is taken daily (minimum 2 tablespoons) with each meal, along with tips for its systematic use in all culinary preparations (in dressings and fried foods).

Blood controls are performed on D0, then at 4, 8, and 12 weeks (CT, LDL-C, HDL, TG), as well as a clinical examination (weight, height, BP), and a compliance control. The results obtained are assembled in Table 1 which follows:

TABLE 1

Average decrease in CT - LDL-C - TG
concerning 81% of studied cases

| | |
|---|---|
| Overall population (104 adults) | Average decrease in CT: 19% |
| | Average decrease in LDL-C: 24% |
| Isolated hypercholesterolemia (75 cases) | Average decrease in CT: 18.3% |
| | Average decrease in LDL-C: 24.8% |
| Mixed hyperlipidemia (29 cases) | Average decrease in CT: 19.5% |
| | Average decrease in LDL-C: 23.7% |
| | Average decrease in CT: 35.5% |

19% of low- or no-responds cases prove to have thyroid or diabetic disorders. Nevertheless continuing follow-ups beyond 12 weeks shows a progressive improvement of the CT and LDL-C values in 30% of these cases.

Example 19

Metabolism of Lipids in the Composition of the Invention According to Example 3

The criteria of inclusion and exclusion are identical to the preceding study. The nutritional intervention is a study carried out over a test period of 4 weeks in a population of 35 adults (13 men and 22 women) with an average age of: 61.1 years, presenting on D0 an average cholesterol level of 2.85 g/l (7.5 mmol/l) and LDL-C of 2.02 g/l (5.25 mmol/l). On the first day of the study, the composition obtained according to Example 3 is taken daily each morning and evening separately from meals.

Clinical and biological controls (D0 and 4 weeks) are identical.

The results obtained are assembled in Table 2 which follows:

TABLE 2

Average decrease in CT - LDL-C - TG
concerning 80% of studied cases

| | |
|---|---|
| Overall population (35 adults) | Average decrease in CT: 18.5% |
| | Average decrease in LDL-C: 24% |
| Isolated hypercholesterolemia (15 cases) | Average decrease in CT: 19.6% |
| | Average decrease in LDL-C: 24% |
| Mixed hyperlipidemia (13 cases) | Average decrease in CT: 17.3% |
| | Average decrease in CT: 49% |

20% of low- or no-response cases prove to be suffering from thyroid, cardiovascular, or diabetic disorders. Nevertheless continuing follow-ups beyond 4 weeks shows a progressive improvement of the CT and LDL-C values in 34% of these cases.

The invention claimed is:

1. A composition designed to regulate lipid metabolism in humans and animals comprising, per 100 g or 100 ml, the combination of:
   a) 7 µg to 700 µg of at least two plant oils selected from the group consisting of rapeseed oil, olive oil, grape seed oil, and evening primrose oil;
   b) 10 µg to 1000 µg of positively charged minerals selected from the group consisting of sodium, magnesium, and calcium;
   c) 10 µg to 1000 µg of metals selected from the group consisting of zinc and iron;
   d) 7 µg to 700 µg of yeast or yeast extracts from genus *Saccharomyces*, characterized in that said yeasts or yeast extracts are enriched with selenium;
   e) 7 µg to 700 µg of mycelium or mycelium extracts obtained from Shiitake;
   f) 6 µg to 600 µg of at least two vegetable extracts selected from the group consisting of samphire, garlic, and grapevine;
   g) 8 µg to 800 µg of at least one vitamin selected from the group consisting of vitamins A, B1, B9, C, E, F, and PP;
   h) 7 µg to 700 µg of an animal oil and Copra oil;
   i) 6 µg to 600 µg of at least one alga selected from the group consisting of *Palmaria palmate, Chondrus crispus, Fucus vesiculosus*, and a pharmaceutically and/or nutritionally acceptable excipient.

2. The composition designed to regulate lipid metabolism in humans and animals according to claim 1, wherein the animal oil consists of cold water fish oil.

3. The composition designed regulate lipid metabolism in humans and animals according to claim 1, wherein said composition contains at least two vitamins selected from the group consisting of vitamins A, B1, B9, C, E, F, and PP.

4. The composition according to claim 1, wherein the composition comprises per 100 g or 100 ml, the combination of:
   a) 7 µg to 700 µg of rapeseed oil, olive oil, grape seed oil, and evening primrose oil;
   b) 10 µg to 1000 µg of sodium, magnesium, and calcium;
   c) 10 µg to 1000 µg of zinc and iron;
   d) 7 µg to 700 µg of yeasts or yeast extracts obtained from *Saccharomvces cerevisiae*, enriched with selenium;
   e) 7 µg to 700 µg of mycelium or mycelium extracts obtained from Shiitake,
   f) 6 µg to 600 µg of samphire, garlic, and grapevine;
   g) 8 µg to 800 µg of vitamins A, B1, B9, C, E, F, and PP;
   h) 7 µg to 700 µg of cold water fish oil and Copra oil, and
   i) 6 µg to 600 µg of *Palmaria palmate, Chondrus crispus*, and *Fucus vesiculosus*.

5. The composition according to claim 1, wherein the composition further comprises excipients or additives.

6. The composition according to claim 1, wherein the composition is in the form of a solid, liquid, oil, gel, strip, paste, powder, or gum.

7. The composition according to claim 1, wherein the composition is suitable for oral administration.

8. The composition according to claim 1, wherein the composition is in the form of a food or a drink with the further addition of a supplement or a food additive.

9. The composition according to claim 1, for use as a medicament.

10. The composition according to claim 1, wherein the yeast or yeast extracts are from *Saccharomyces cerevisiae*.

11. A medicament comprising the composition of claim 1.

12. A food additive comprising the composition of claim 1.

13. A nutritional supplement comprising the composition of claim 1.

14. A cosmetic comprising the composition of claim 1.

15. The composition according to claim 5, wherein the additives are selected from the group consisting of sweeteners, stabilizing agents, preservatives, dyes, emulsifiers or gelling agents, flavor enhancers, acidifiers, and flavors.

16. A method of regulating lipid metabolism in humans and animal, said method comprising administering an effective amount of the composition according to claim 1 to a subject in need thereof to reduce one or more of the following:
   plasma cholesterol level, plasma LDL level, or plasma triglyceride level.

17. A method of treating obesity comprising administering an effective amount of the composition according to claim 1 to a subject in need thereof to stimulate lipid consumption.

18. A method of treating obesity comprising administering an effective amount of the composition according to claim 1 to a subject in need thereof to reduce intestinal absorption of food lipid.

19. A method of improving physical endurance, said method comprising administering an effective amount of the composition according to claim 1 to a subject in need thereof to increase oxidative metabolism and oxygen uptake.

20. A method of increasing muscle motility, said method comprising administering an effective amount of the composition according to claim 1 to a subject in need thereof to increase oxidative metabolism and oxygen uptake.

\* \* \* \* \*

UNITED STATES PATENT AND TRADEMARK OFFICE
CERTIFICATE OF CORRECTION

PATENT NO. : 8,361,517 B2
APPLICATION NO. : 12/738116
DATED : January 29, 2013
INVENTOR(S) : Bourgeois-Lugand et al.

It is certified that error appears in the above-identified patent and that said Letters Patent is hereby corrected as shown below:

On the Title page; in Item (75) Inventors:

Fifth inventor should read "Gillies Didier Parisot, Ollon (CH)"

Column 24, line 25: "difference is here is also"

Should read "difference here is also"

Signed and Sealed this
Ninth Day of April, 2013

Teresa Stanek Rea
*Acting Director of the United States Patent and Trademark Office*